(12) United States Patent
Gallippi et al.

(10) Patent No.: US 11,397,227 B2
(45) Date of Patent: Jul. 26, 2022

(54) METHODS, SYSTEMS, AND COMPUTER-READABLE MEDIA FOR NONDESTRUCTIVELY MEASURING PHYSICAL PROPERTIES OF A MATERIAL BY OBSERVING INDUCED DISPLACEMENTS USING DIFFERENT FOCAL CONFIGURATIONS

(71) Applicant: The University of North Carolina at Chapel Hill, Chapel Hill, NC (US)

(72) Inventors: Caterina M. Gallippi, Cary, NC (US); Keita Andrew Yokoyama, Chapel Hill, NC (US); Md Murad Hossain, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 17/150,612

(22) Filed: Jan. 15, 2021

(65) Prior Publication Data
US 2021/0239775 A1   Aug. 5, 2021

Related U.S. Application Data

(60) Provisional application No. 62/961,612, filed on Jan. 15, 2020.

(51) Int. Cl.
*G01R 33/24* (2006.01)
*G01R 33/58* (2006.01)
*G01R 33/36* (2006.01)

(52) U.S. Cl.
CPC ............ *G01R 33/24* (2013.01); *G01R 33/36* (2013.01); *G01R 33/58* (2013.01)

(58) Field of Classification Search
USPC ......................................... 324/301
See application file for complete search history.

(56) References Cited

U.S. PATENT DOCUMENTS

| | | | |
|---|---|---|---|
| 6,418,776 | B1 | 7/2002 | Gitis et al. |
| 7,497,134 | B2 | 3/2009 | Renken et al. |
| | | (Continued) | |

FOREIGN PATENT DOCUMENTS

SU          1392447 A          4/1988

OTHER PUBLICATIONS

Commonly-Assigned, Co-pending U.S. Appl. No. 17/204,919 for "Quantitative Viscoelastic Response (QVisR) Ultrasound," (Unpublished, filed Mar. 17, 2021).

(Continued)

*Primary Examiner* — Rodney E Fuller
(74) *Attorney, Agent, or Firm* — Jenkins, Wilson, Taylor & Hunt, P.A.

(57) ABSTRACT

A method for quantitatively measuring a physical characteristic of a material includes performing one or more interrogations of a material sample, each interrogation using a push focal configuration. The method further includes taking measurements of displacement over time of a material sample caused by the one or more interrogations. Each measurement uses an interrogation focal configuration. The method further includes determining a physical characteristic of the material sample based on the measurements of displacement over time of the material sample. According to the method, at least one of the following is true: a tracking focal configuration used for one of the measurements is different from a tracking focal configuration used for another of the measurements; and a push focal configuration used for one of the interrogations is different from a push focal configuration used for another of the interrogations.

29 Claims, 25 Drawing Sheets

(56) References Cited

U.S. PATENT DOCUMENTS

| | | | |
|---|---|---|---|
| 7,535,217 | B2 | 5/2009 | Quandt et al. |
| 8,753,277 | B2 | 6/2014 | McAleavey |
| 9,211,111 | B2* | 12/2015 | Tamura ................ A61B 8/5207 |
| 9,244,041 | B2 | 1/2016 | Gallippi et al. |
| 10,772,608 | B2 | 9/2020 | Kanayama |
| 2003/0182069 | A1 | 9/2003 | Banes et al. |
| 2007/0008821 | A1 | 4/2007 | Woo et al. |
| 2011/0287948 | A1 | 11/2011 | Suresh et al. |
| 2013/0046175 | A1 | 2/2013 | Sumi |
| 2013/0181722 | A1 | 7/2013 | Pfaff |
| 2014/0046187 | A1 | 2/2014 | Taniguchi et al. |
| 2015/0320394 | A1* | 11/2015 | Amal ...................... A61B 8/485 600/438 |
| 2015/0362564 | A1 | 12/2015 | Wan et al. |
| 2019/0183344 | A1 | 6/2019 | Gallippi et al. |
| 2021/0259657 | A1 | 8/2021 | Gallippi et al. |
| 2021/0293677 | A1* | 9/2021 | Gallippi ................ G01N 3/062 |

OTHER PUBLICATIONS

Hossain et al., "Evaluating Renal Transplant Status Using Viscoelastic Response (VisR) Ultrasound," Ultrasound in Med. & Biol., vol. 44, No. 8, pp. 1573-1584 (2018).

Moore et al., "In Vivo Viscoelastic Response (VisR) Ultrasound for Characterizing Mechanical Anisotrophy in Lower-Limb Skeletal Muscles of Boys with and without Duchenne Muscular Dystrophy," Ultrasound in Med Biol., vol. 44, No. 12, pp. 1-23 (Dec. 2018).

Barr et al., "WFUMB Guidelines and Recommendations for Clinical Use of Ultrasound Elastography: Part 2: Breast," Ultrasound in Med. & Biol., vol. 41, No. 5, pp. 1148-1160 (2015).

Shiina et al., "WFUMB Guidelines and Recommendations for Clinical Use of Ultrasound Elastogrpahy: Part 1: Basic Principles and Terminology," Ultrasound in Med. & Biol., vol. 41, No. 5, pp. 1126-1147 (2015).

Ferraioli et al., "WFUMB Guidelines and Recommendations for Clinical Use of Ultrasound Elastography: Part 3: Liver," Ultrasound in Med & Biol., vol. 41, No. 5, pp. 1161-1179 (2015).

Nightingale, "Acoustic Radiation Force Impulse (ARFI) Imaging: a Review," Curr Med Imaging Rev., vol. 7, No. 4, pp. 1-24 (Nov. 1, 2011).

Pedregosa et al., "Scikit-learn: Machine Learning in Python," Journal of Medicine Learning Research, arXiv:1201.0490v4, vol. 12, pp. 1-6 (2011).

Non-Final Office Action for U.S. Appl. No. 16/301,085 (dated Sep. 24, 2021).

Commonly-assigned, Co-pending U.S. Appl. No. 17/176,772 for "Methods, Systems, and Computer Readable Media for Evaluating Mechanical Anisotropy for Breast Cancer Screening and Monitoring Response to Therapy," (Unpublished, filed Feb. 16, 2021).

Hossain et al., "Viscoelectric Response Ultrasound Derived Relative Elasticity and Relative Viscosity Reflect True Elasticity and Viscosity: In Silico and Experimental Demonstration," IEEE Transactions on Ultrasonics, Ferroelectrics, and Frequency Control, vol. 67, No. 6, pp. 1102-1117 (Jun. 2020).

Zhang et al., "Fluidity and elasticity form a concise set of viscoelastic biomarkers for breast cancer diagnosis based on Kelvin-Voigt fractional derivative modeling," Springer, pp. 1-16 (Apr. 25, 2020).

Hossain et al., "Improvement in Inclusion Contrast-to-Noise Ratio for Low-Displacement Acoustic Radiation Force (ARF) Elasticity Imaging Using a 3D Kernel Blind-Source Separation (BSS) Based Displacement Estimator," 2019 IEEE International Ultrasonics Symposium (IUS), pp. 1395-1398 (Oct. 2019).

Yokoyama et al., "Double-profile intersection (DoPIo) elastography: a new approach to quantifying tissue elasticity," 2019 IEEE International Ultrasonics Symposium (IUS), pp. 1-4 (Oct. 2019).

Torres et al., "Viscoelastic Response (VisR)-Derived Mechanical Anisotropy for Differentiating Malignant from Benign Breast Lesions in Women, in vivo," 2019 IEEE International Ultrasonic Symposium (IUS), pp. 1-3 (2019).

You et al., "Quantitative and Qualitative Evaluation of Breast Cancer Prognosis: A Sonographic Elastography Study," Med Sci Monit, vol. 25, pp. 1-8 (2019).

Sood et al., "Ultrasound for Breast Cancer Detection Globally: A Systematic Review and Meta-Analysis," Journal of Global Oncology, pp. 1-17 (Aug. 27, 2019).

Nabavizadeh et al., "Viscoelastic biomarker for differentiation of benign and malignant breast lesion in ultra-low frequency range," Scientific Reports, vol. 9, No. 5737, pp. 1-12 (2019).

Notification Concerning Transmittal of International Preliminary Report on Patentability for International Application Serial No. PCT/US2017/032745 (dated Nov. 22, 2018).

Chen et al., "Ultrasound shear wave elastography of breast lesions: correlation of anisotropy with clinical and histopathological findings," Cancer Imaging, vol. 18, No. 11, pp. 1-11 (2018).

Zahran et al., "Ultrasound elastography: How can it help in differentiating breast lesions?" The Egyptian Journal of Radiology and Nuclear Medicine, vol. 49, pp. 1-10 (2018).

Youk et al., "Shear-wave elastography in breast ultrasonography: the state of the art," Ultrasonography, vol. 36, No. 4, pp. 300-309 (Oct. 2017).

Notification of Transmittal of the International Search Report and the Written Opinion of the International Searching Authority, or the Declaration for International Application Serial No. PCT/US2017/032745 (dated Aug. 2017).

Hossain et al., "Acoustic Radiation Force Impulse-Induced Peak Displacements Reflect Degree of Anisotrophy in Transversely Isotropic Elastic Materials," IEEE Transactions on Ultrasonics, Ferroelectrics, and Frequency Control, vol. 64, No. 6, pp. 989-1001 (Jun. 2017).

Selzo et al., "On the Quantitative Potential of Viscoelastic Response (VisR) Ultrasound Using the One-Dimensional Mass-Spring-Damper Model," IEEE Trans Ultrason Ferroelectr Freq Control, vol. 63, No. 9, pp. 1-29 (Sep. 2016).

Skerl et al., "Anisotropy of solid breast lesions in 2D shear wave elastography is an indicator of malignancy," Academic Radiology, vol. 23, No. 1, pp. 1-32 (2016).

Giannotti et al., "Shear-wave elastography and greyscale assessment of palpable probably benign masses: is biopsy always required?" Br J Radiol, vol. 89, pp. 1-7 (2016).

Kuzmiak, "Breast Cancer Survivors: Does the Screening MRI Debate Continue?" Acad Radiol, vol. 22, pp. 1329-1330 (2015).

Barr et al., "Shear-Wave Elastography of the Breast: Value of a Quality Measure and Comparison with Strain Elastography," Radiology, vol. 000, No. 0, pp. 1-9 (2015).

Grajo et al., "Strain Elastography for Prediction of Breast Cancer Tumor Grades," J Ultrasound Med, vol. 33, pp. 129-134 (2014).

Selzo et al., "Viscoelastic Response (VisR) Imaging for Assessment of Viscoelasticity in Voigt Materials," IEEE Trans Ultrason Ferroelectr Freq Control, vol. 60, No. 12, pp. 1-23 (Dec. 2013).

Rouze et al., "Finite Element Modeling of Impulsive Excitation and Shear Wave Propagation in an Incompressible, Traversely Isotropic Medium," J Biomech, vol. 46, No. 16, pp. 1-18 (Nov. 15, 2013).

Wang et al., "Imaging Transverse Isotropic Properties of Muscle by Monitoring Acoustic Radiation Force Induced Shear Waves Using a 2-D Matrix Ultrasound Array," IEEE Transactions on Medical Imaging, vol. 32, No. 9, pp. 1671-1684 (Sep. 2013).

Czernuszewicz et al., "Experimental Validation of Displacement Underestimation in ARFI Ultrasound," Ultrason Imaging, vol. 35, No. 3, pp. 1-24 (Jul. 2013).

Dhanaliwala et al, "Assessing and improving acoustic radiation force image quality using a 1.5D transducer design," IEEE Trans Ultrason Ferroelectr Freq Control, vol. 59, No. 7, pp. 1-16 (Jul. 2012).

Cole et al., "Assessing the Standalone Sensitivity of Computer-aided Detection (CADe) with Cancer Cases from the Digital Mammographic Imaging Screening Trial (DMIST)," AJR Am J Roentgenol., vol. 199, No. 3, pp. 1-20 (2012).

Berg et al., "Detection of Breast Cancer with Addition of Annual Screening Ultrasound or a Single Screening MRI to Mammography in Women with Elevated Breast Cancer Risk," JAMA, vol. 307, No. 13, pp. 1-18 (Apr. 4, 2012).

(56) References Cited

OTHER PUBLICATIONS

Qiu et al., "Ultrasonic Viscoelasticity Imaging of Nonpalpable Breast Tumors: Preliminary Results," Acad Radiol, vol. 15, No. 12, pp. 1-17 (Dec. 2008).

Ostrovsky et al., "Radiation force and shear motions in inhomogeneous media," The Journal of Acoustical Society of America, vol. 121, No. 1324 pp. 1-9 (2007).

Palmeri et al., "Ultrasonic Tracking of Acoustic Radiation Force-Induced Displacements in Homogeneous Media," IEEE Trans Ultrason Ferroelectr Freq Control, vol. 53, No. 7, pp. 1-24 (Jul. 2006).

Pinton et al., "Rapid Tracking of Small Displacements with Ultrasound," IEEE Transactions on Ultrasonics, Ferroelectrics, and Frequency Control, vol. 53 No. 6, pp. 1103-1117 (Jun. 2006).

Palmeri et al., "A Finite-Element Method Model of Soft Tissue Response to Impulsive Acoustic Radiation Force," IEEE Transactions on Ultrasonics, Ferroelectrics, and Frequency Control, vol. 52, No. 10, pp. 1699-1712 (Oct. 2005).

Sinkus et al., "Imaging Anisotropic and Viscous Properties of Breast Tissue by Magnetic Resonance-Elastography," Magnetic Resonance in Medicine, vol. 53, pp. 372-387 (2005).

Jensen et al., "Simulation of advanced ultrasound systems using Field II," In IEEE International Symposium on Biomedical Engineering, pp. 1-5 (2004).

Chen et al., "Quantifying elasticity and viscosity from measurement of shear wave speed dispersion," J. Acoust. Soc. Am., vol. 115, No. 6, pp. 2781-2785 (Jun. 2004).

Nightingale et al., "Sheav-wave Generation Using Acoustic Radiation Force: In Vivo and Ex Vivo Results," Ultrasound in Med. & Biol., vol. 29, No. 12, pp. 1-9 (2003).

Sandrin et al., "Transient Elastography: A New Noninvasive Method for Assessment of Hepatic Fibrosis," Ultrasound in Med. & Biol., vol. 29, No. 12, pp. 1-9 (2003).

McAleavey et al., "Estimates of Echo Correlation and Measurement Bias in Acoustic Radiation Force Impulse Imaging," IEEE Transactions on Ultrasonics, Ferroelectrics, and Frequency Control, vol. 50, No. 6, pp. 631-641 (Jun. 2003).

Nightingale et al., "Acoustic Radiation Force Impulse Imaging: In Vivo Demonstration of Clinical Feasibility," Ultrasound in Medicine and Biology, pp. 1-21 (Oct. 24, 2001).

Chan et al., "Active Contours Without Edges," IEEE Transactions on Image Processing, vol. 10, No. 2, pp. 266-277 (Feb. 2001).

Torr, "MLESAC: A New Robust Estimator with Application to Estimating Image Geometry," Computer Vision and Image Understanding, vol. 78, pp. 138-156 (2000).

Sarvazyan et al., "Shear Wave Elasticity Imaging: A New Ultrasonic Technology of Medical Diagnostics," Ultrasound in Med. & Biol., vol. 24, No. 9, pp. 1419-1435 (1998).

Walker et al., "A Fundamental Limit on Delay Estimation Using Partially Correlated Speckle Signals," IEEE Transactions on Ultrasonics, Ferroelectrics, and Frequency Control., vol. 42, No. 2, pp. 301-308 (Mar. 1995).

Ponnekanti et al., "Fundamental Mechanical Limitations on the Visualization of Elasticity Contrast in Elastography," Ultrasound in Med. & Biol., vol. 21, No. 4, pp. 533-543 (1995).

Jensen et al., "Calculation of Pressure Fields from Arbitrarily Shaped, Apodized, and Excited Ultrasound Transducers," IEEE Transactions on Ultrasonics, Ferroelectrics, and Frequency Control, vol. 39, No. 2, pp. 1-7 (1992).

Smith et al., "Properties of Acoustical Speckle in the Presence of Phase Aberration Part II: Correlation Lengths," Ultrasonic Imaging, pp. 29-51 (1988).

Trahey et al., "Properties of Acoustical Speckle in the Presence of Phase Aberration Part I: First Order Statistics," Ultrasonic Imaging, pp. 12-28 (1988).

Wagner et al., "Statistics of Speckle in Ultrasound B-Scans," IEEE Transactions on Sonics and Ultrasonics, vol. 30, No. 3, pp. 156-163 (May 1983).

Fritsch et al., "Monotone Piecewise Cubic Interpolation," Siam J. Numer. Anal., vol. 17, No. 2, pp. 238-246 (Apr. 1980).

Graustein, "Homogeneous Cartesian Coordinates, Linear Dependence of Points and Lines," Introduction to Higher Geometry, Chapter III, pp. 1-22 (1930).

Notice of Allowance for U.S. Appl. No. 16/301,085 (dated May 11, 2022).

Notice of Allowance for U.S. Appl. No. 16/301,085 (dated Jan. 28, 2022).

\* cited by examiner

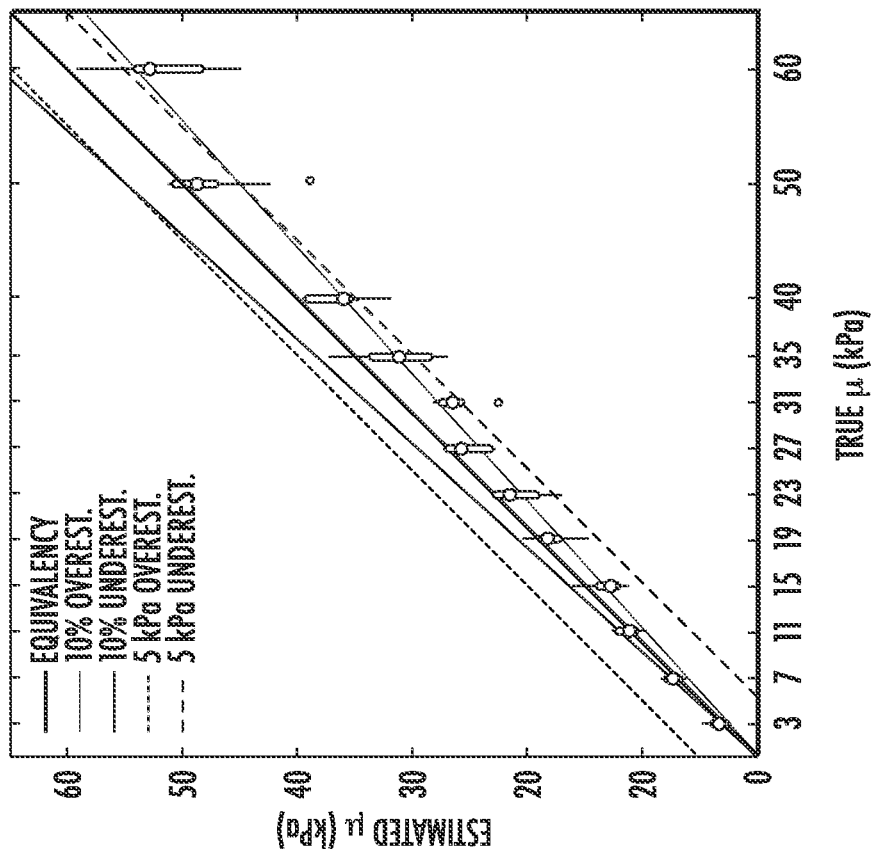
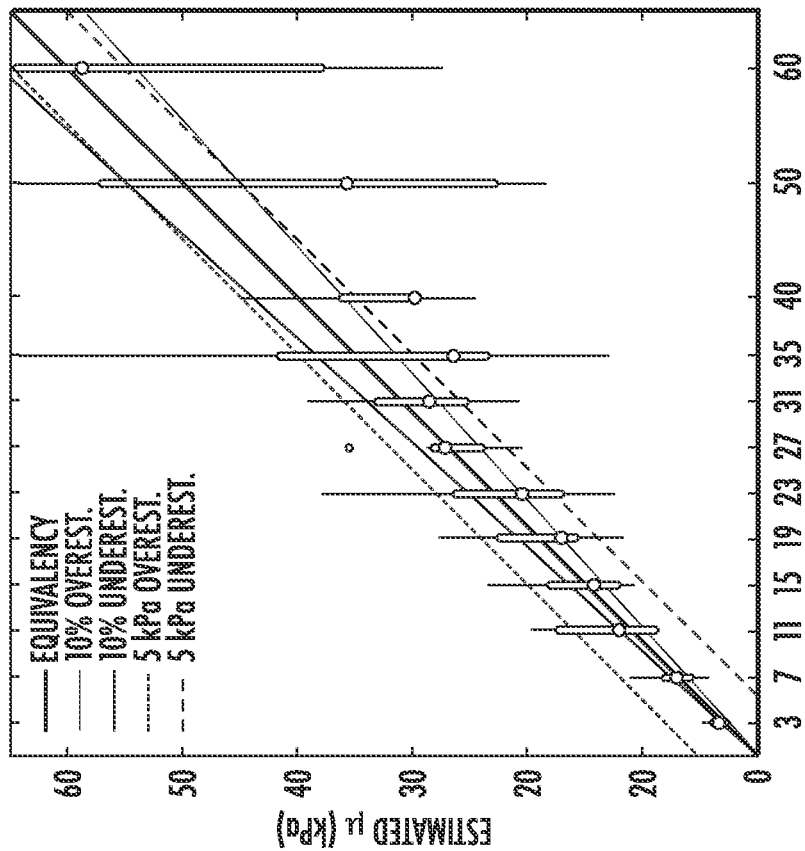
FIG. 21B
FIG. 21A

METHODS, SYSTEMS, AND COMPUTER-READABLE MEDIA FOR NONDESTRUCTIVELY MEASURING PHYSICAL PROPERTIES OF A MATERIAL BY OBSERVING INDUCED DISPLACEMENTS USING DIFFERENT FOCAL CONFIGURATIONS

PRIORITY CLAIM

This application claims the priority benefit of U.S. Provisional patent Application Ser. No. 62/961,612, filed Jan. 15, 2020, the disclosure of which is incorporated herein by reference in its entirety.

GOVERNMENT INTEREST

This invention was made with government support under Grant Nos. DK107740, HL092944, and NS074057 awarded by the National Institutes of Health. The government has certain rights in the invention.

BACKGROUND

Palpation is one of the few simple strategies for medical diagnosis that have remained a powerful tool in the modern age. In applications such as identification of cysts, or self-examination in the breast and testes, the viscoelastic nature of human tissue has long been exploited as a method to identify signs for formalized medical examinations. However, traditional palpation is limited to superficial organs with abnormalities that can be easily detected through centimeters of skin and subcutaneous fat layers and is highly subjective. There is a need for a deep-tissue and objective counterpart to palpation to noninvasively measure stiffness. This is the purpose of elastography, which is gaining clinical acceptance as a method to characterize tissue based on its mechanical properties.

In one approach to ultrasound elastography, the mechanical properties of tissue are measured by interrogating it with a brief pulse of Acoustic Radiation Force (ARF) using a transducer. Tissue displaces and relaxes in response, and the axial displacements of acoustic scatterers are then tracked over time, with averaging of individual, sub-resolution scatterer displacements over the tracking resolution volume. These tracked displacements profiles can represent submicron displacements using algorithms such as normalized cross-correlation, and be processed to extract parameters of interest that may or may not be rendered into parametric images.

The most mainstream paradigms of ARF-based ultrasonic elastography are ARF Impulse (ARFI) imaging, in which ARF-induced tissue displacements are displayed as a color map, and Shear-Wave Elasticity Imaging (SWEI), in which ARF-induced shear wave propagations are tracked to determine the shear modulus of a region of tissue. Unfortunately, ARFI only allows stiffness to be compared within a single image qualitatively, not quantitatively, and SWEI produces a numerical measurement by averaging multiple measures over several millimeters and assuming that tissue is homogeneous (i.e., tissue stiffness does not change) across that range.

It is important to consider that the ARFI excitation produced by an ultrasound transducer does not have uniform magnitude over space. This unequal distribution of force results in unequal scatterer displacements that are averaged under the tracking resolution volume, causing an underestimation of the true peak displacements.

While these elastography methods can still be useful in certain situations such as delineating tumors in soft tissue, characterizing carotid plaque structure and composition, or tracking dystrophic muscle degeneration, conventional ARF-based techniques can be unreliable due to factors, such as error from displacement underestimation or signal corruption from shear wave reflections.

Therefore, there is a need for improved methods and systems for quantitatively and qualitatively assessing characteristics of materials, such as tissue elasticity, viscosity, and anisotropy.

SUMMARY

Methods, systems, and computer-readable media for nondestructively quantitatively measuring physical properties of a material by observing induced displacements using different focal configurations are disclosed.

One embodiment, which is referred to herein as double-profile intersection (DoPlo) elastography, is an acoustic radiation force (ARF)-based ultrasonic imaging method that exploits scatterer shearing in the ultrasonic tracking of acoustic radiation force responses to allow for the noninvasive, pointwise, and quantitative or qualitative assessment of tissue shear modulus. DoPlo monitors the displacement response of tissue to a focused acoustic radiation force (ARF) using two different aperture configurations. The two displacement profiles resulting from the two aperture configurations are compared to identify a common timepoint that is unique to a given distance from an ARF excitation, tracking focal configuration combination, and shear modulus. This time of intersection (TI) can be passed through an empirically-derived model to infer a shear modulus of within individual resolution cells.

According to one aspect of the present disclosure, a method for quantitatively measuring a physical characteristic of a material comprises: performing one or more interrogations of a material sample, each interrogation using a push focal configuration. The method further includes taking a plurality of measurements of displacement over time of a material sample caused by the one or more interrogations, each measurement using an interrogation focal configuration. In one example, the plural measurements of displacement can be obtained from a single signal capture by a multi-element receiving transducer array and applying post-processing of the captured signal to use measurements from different elements of the receiving transducer array to achieve different tracking focal configurations. The method further includes determining a physical characteristic of the material sample based on the plurality of measurements of displacement over time of the material sample, wherein at least one of: a tracking focal configuration used for one of the plurality of measurements is different from a tracking focal configuration used for another of the plurality of measurements; and/or a plurality of interrogations is performed, wherein a push focal configuration used for one of the plurality of interrogations is different from a push focal configuration used for another of the plurality of interrogations.

In some embodiments, performing one or more interrogations of a material sample comprises: applying, to a spatial position of a material sample, an interrogation having a push focal configuration and causing a displacement over time of the material sample; and taking a plurality of measurements of displacement over time of a material sample caused by the one or more interrogations comprises: taking, using a first tracking focal configuration, a first measurement of displacement over time of the material sample; and taking, using a second tracking focal configuration different from the first tracking focal configuration, a second measurement of displacement over time of the material sample.

In some embodiments, the first and second measurements of displacement over time are taken contemporaneously. For example, as described above, post-processing of the received ultrasound signal can be used to obtain measurements with different tracking focal configurations.

In some embodiments, the first and second measurements of displacement over time are taken sequentially. Even though the methodology is described herein using "first and second measurements" as an example, obtaining more than two measurements is intended to be within the scope of the subject matter described herein.

In some embodiments, performing one or more interrogations of a material sample and taking a plurality of measurements of displacement over time of a material sample caused by the one or more interrogations comprises: applying, to a spatial position of a material sample, an interrogation having a first push focal configuration and causing a first displacement over time of the material sample; taking, using a first tracking focal configuration, a measurement of the first displacement over time of the material sample; and applying, to a spatial position of a material sample, and a second interrogation having the first push focal configuration and causing a second displacement over time of the material sample; taking, using a second tracking focal configuration different from the first tracking focal configuration, a measurement of a second displacement over time of the material sample. As indicated above, it is not necessary to use two different pushes or interrogations of a material sample to obtain two measurements with different tracking focal configurations. A single push or interrogation and a single reception (with different tracking focal configurations) may be used, and post-processing of the received signal may be performed to achieve the different tracking focal configurations. For example, the post-processing may consider signals from different elements of a multi-element ultrasound transducer array to yield the different tracking focal configurations. If two pushes or more than two pushes are used, the multiple pushes are preferably administered at different times so that the resulting response to each push can be individually characterized.

In some embodiments, performing one or more interrogations of a material sample and taking a plurality of measurements of displacement over time of a material sample caused by the one or more interrogations comprises: applying, to a spatial position of a material sample, an interrogation having a first push focal configuration and causing a first displacement over time of the material sample; taking, using a first tracking focal configuration, a measurement of the first displacement over time of the material sample; and applying, to a spatial position of a material sample, an interrogation having a second push focal configuration different from the first push focal configuration and causing a second displacement over time of the material sample; taking, using the first tracking focal configuration, a measurement of a second displacement over time of the material sample.

In some embodiments, performing one or more interrogations of a material sample and taking a plurality of measurements of displacement over time of a material sample caused by the one or more interrogations comprises: applying, to a spatial position of a material sample, an interrogation having a first push focal configuration and causing a first displacement over time of the material sample; taking, using a first tracking focal configuration, a measurement of the first displacement over time of the material sample; and applying, to a spatial position of a material sample, an interrogation having a second push focal configuration different from the first push focal configuration and causing a second displacement over time of the material sample; taking, using a second tracking focal configuration different from the first tracking focal configuration, a measurement of a second displacement over time of the material sample.

In some embodiments, the physical characteristic of the material sample comprises elasticity of the material sample, viscosity of the material sample, or anisotropy of the material sample.

In some embodiments, the material sample comprises a tissue sample.

In some embodiments, a tracking focal configuration used for one of the plurality of measurements is narrower than a tracking focal configuration used for another of the plurality of measurements.

In some embodiments, a push focal configuration used for one of the plurality of interrogations is narrower than a push focal configuration used for another of the plurality of interrogations.

In some embodiments, performing at least one interrogation comprises applying an Acoustic Radiation Force (ARF) to the material sample.

In some embodiments, at least one of the displacements over time of the material sample is measured using ultrasound.

In some embodiments, at least one of the displacements over time of the material sample is measured using an optical method.

In some embodiments, at least one of the displacements over time of the material sample is measured using an optical microscope.

In some embodiments, the optical method comprises Optical Coherence Tomography (OCT).

In some embodiments, at least one of the displacements over time of the material sample is measured using Magnetic Resonance Imaging (MRI).

In some embodiments, determining the physical characteristic of the material sample based on the first and second displacements over time of the material sample comprises calculating the physical characteristic according to an algorithm that uses the first and second displacements over time of the material sample as inputs to calculate a value of the physical characteristic.

In some embodiments, the algorithm also uses the first tracking focal configuration and the second tracking focal configuration to calculate the physical characteristics.

In some embodiments, the algorithm also uses the focal depth and/or the lateral offset from the region of excitation to calculate the physical characteristics.

In some embodiments, the algorithm comprises the steps of: superimposing the first displacement over time of the material sample and the second displacement over time of the material sample; identifying or inferring features that are common to both displacements over time of the material sample; and determining the physical characteristic based on the identified or inferred common features.

In some embodiments, the common features comprise at least one of: a first time at which a graph of the first displacement over time of the material sample intersects with a graph of the second displacement over time of the material sample; a second time at which the graph of the first displacement over time of the material sample intersects with the graph of the second displacement over time of the material sample; and a time at which the graph of the first or second displacement over time of the material sample indicates a particular rate of recovery.

In some embodiments, the algorithm comprises a machine learning algorithm.

In some embodiments, the machine learning algorithm comprises a bagged tree model.

In some embodiments, the machine learning algorithm comprises a Gaussian process regression model.

According to one aspect of the present disclosure, a system for measuring a physical characteristic of a material comprises processing circuitry configured to: perform one or more interrogations of a material sample, each interrogation using a push focal configuration; take a plurality of measurements of displacement over time of a material sample caused by the one or more interrogations, each measurement using an interrogation focal configuration; and quantitatively or qualitatively assess a physical characteristic of the material sample based on the plurality of measurements of displacement over time of the material sample, wherein at least one of: a tracking focal configuration used for one of the plurality of measurements is different from a tracking focal configuration used for another of the plurality of measurements; and/or a plurality of interrogations is performed, wherein a push focal configuration used for one of the plurality of interrogations is different from a push focal configuration used for another of the plurality of interrogations.

In some embodiments, the circuitry is configured to carry out any of the methods disclosed herein.

According to one aspect of the present disclosure, a system for measuring a physical characteristic of a material comprises one or more processors and memory storing instructions executable by the one or more processors, whereby the system is operable to: perform one or more interrogations of a material sample, each interrogation using a push focal configuration; take a plurality of measurements of displacement over time of a material sample caused by the one or more interrogations, each measurement using an interrogation focal configuration; and quantitatively or qualitatively assess a physical characteristic of the material sample based on the plurality of measurements of displacement over time of the material sample, wherein at least one of: a tracking focal configuration used for one of the plurality of measurements is different from a tracking focal configuration used for another of the plurality of measurements; and/or a plurality of interrogations is performed, wherein a push focal configuration used for one of the plurality of interrogations is different from a push focal configuration used for another of the plurality of interrogations.

In some embodiments, quantitatively or qualitatively assessing the physical characteristic includes quantitatively assessing the physical characteristic by relating the measurements to a corresponding quantity of the physical characteristic using a model that relates quantities of the physical characteristic to displacements over time, and more particularly that relates quantities of the physical characteristic to the time that displacement versus time curves for the different focal configurations intersect.

In some embodiments, quantitatively or qualitatively assessing the physical characteristic includes qualitatively assessing the physical characteristic by using the measurements to assess a relative quality or amount of the physical characteristic in the material sample when compared to other material samples or to results from interrogations of the same material sample at different times.

In some embodiments, via execution of the instructions by the one or more processors, the system is operable to carry out any of the methods disclosed herein.

According to one aspect of the present disclosure, a system for measuring a physical characteristic of a material comprises one or more modules configured to: perform one or more interrogations of a material sample, each interrogation using a push focal configuration; take a plurality of measurements of displacement over time of a material sample caused by the one or more interrogations, each measurement using an interrogation focal configuration; and quantitatively or qualitatively assess a physical characteristic of the material sample based on the plurality of measurements of displacement over time of the material sample, wherein at least one of: a tracking focal configuration used for one of the plurality of measurements is different from a tracking focal configuration used for another of the plurality of measurements; and/or a plurality of interrogations is performed, wherein a push focal configuration used for one of the plurality of interrogations is different from a push focal configuration used for another of the plurality of interrogations.

In some embodiments, the one or more modules are configured to carry out any of the methods disclosed herein.

According to one aspect of the present disclosure, a non-transitory computer readable medium storing software instructions that when executed by one or more processors of a system for measuring a physical characteristic of a material, cause the system to: perform one or more interrogations of a material sample, each interrogation using a push focal configuration; take a plurality of measurements of displacement over time of a material sample caused by the one or more interrogations, each measurement using an interrogation focal configuration; and quantitatively or qualitatively assess a physical characteristic of the material sample based on the plurality of measurements of displacement over time of the material sample, wherein at least one of: a tracking focal configuration used for one of the plurality of measurements is different from a tracking focal configuration used for another of the plurality of measurements; and/or a plurality of interrogations is performed, wherein a push focal configuration used for one of the plurality of interrogations is different from a push focal configuration used for another of the plurality of interrogations.

In some embodiments, the instructions executed by the one or more processors cause the system to carry out any of the methods disclosed herein.

According to one aspect of the present disclosure, a computer program comprises instructions which, when executed by at least one processor, cause the at least one processor to carry out any of the methods disclosed herein.

Those skilled in the art will appreciate the scope of the present subject matter described herein and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the subject matter described herein, and together with the description serve to explain the principles of the subject matter described herein.

In FIGS. 20A-20D, time-intersect distributions are shown across various push-track separations (FIG. 20A) and at the focal depth throughout axial depth for displacements tracked at the RoE (FIG. 20B). The inverse-squared versions of these values (i.e. values used to create empirical model) are depicted in (FIG. 20C) and (FIG. 20D), respectively. All error bars denote the median, 25th and 75th percentiles, and 95% confidence intervals for times-intersect based on 20 scatterer realizations of F-numbers 1.5 and 3.0. Error bars are shaded from 1 kPa (lighter) in 4 kPa increments up to 37 kPa (darker) according to the shear modulus of the ARF-interrogated material;

FIGS. 21A and 21B illustrate shear modulus estimates in homogeneous materials using the derived linear relationship, with displacements tracked at the focal depth using tFc 1.5 and 3.0. FIG. 21A depicts modulus estimates taken at region of excitation (RoE), whereas FIG. 21B corresponds to those at 3.0 mm from the RoE. Descriptive statistics across 10 scatterer realizations of stiffness measurements are depicted as box plots with boxes denoting the median and interquartile ranges, and whiskers denoting the 95% confidence interval;

FIG. 22A depicts modulus estimates for a homogeneous 20 kPa material at the focal depth of 25.00 mm across various push-track separations. FIG. 22B depicts modulus estimates for the same material, but at multiple axial positions given a 2.0 mm push-track separation. Error bars denote mean and standard deviation;

FIG. 23A shows the true stiffness, where the square with side length of 2.5 mm has a shear elastic modulus of 5 kPa whereas the background measures 10 kPa. FIG. 23B depicts the average DoPlo estimate out of 10 scatterer realizations for tFc 1.5 and 3 tracked 2.0 mm from RoE. FIG. 23C is the average of 10 scatterer fields for MTL-SWEI measured with a 2 mm lateral tracking kernel;

FIG. 24A depicts a representative sample of a spherical phantom with a radius of 10 mm centered on the right side of the image at a depth of 30 mm. FIGS. 24B-24F depict DoPlo modulus estimates at increasing ARF push powers; displacements were tracked on-axis to ARF excitations using F-numbers of 1.5 and 3.0 with push focuses at 25 mm. FIGS. 24G and 24H depict modulus estimates in and above the inclusion using NCC and BSS trackers, respectively, and FIGS. 24I and 24J denotes the same for a background region of the phantom.

FIG. 25A shows the average shear modulus map of 10 scatterer realizations of a stiff inclusion in a soft background. using NCC-based DoPlo tracked 2.0 mm from the RoE; FIG. 25B shows a representative example out of the 10 realizations. FIGS. 25C and 25D also follow the same format using the same seeds, but for blind source separation (BSS)-based tracking on-axis to the ARF excitation. The patches of dark colors that are especially noticeable around the inclusion in FIGS. 25B and 25D are assigned NaN values, as times-intersect in those regions could not be detected.

DETAILED DESCRIPTION

Figure 1:
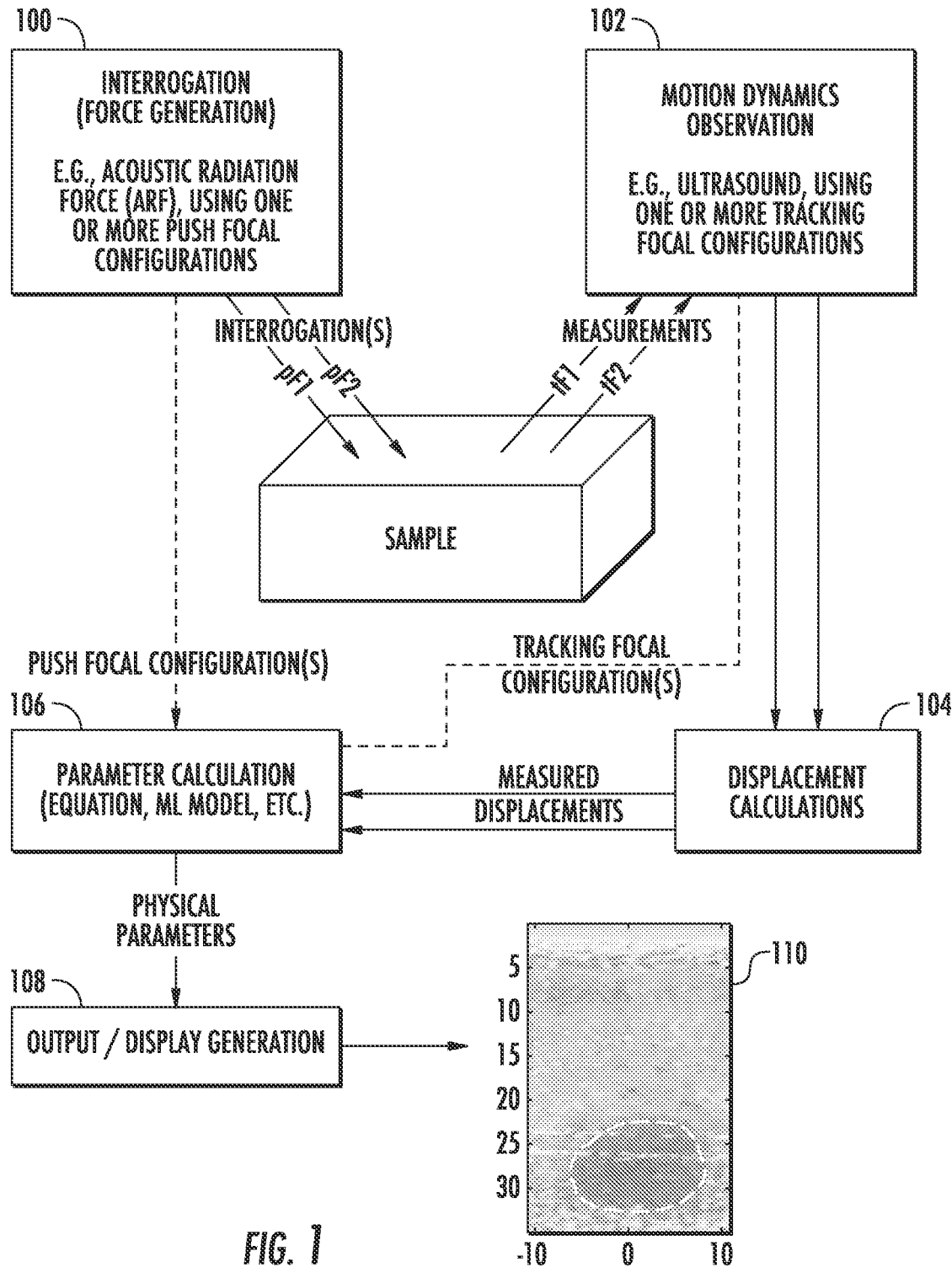
FIG. 1 is block diagram illustrating a system for nondestructively measuring physical properties of samples by observing induced displacements using different focal configurations according to an embodiment of the subject matter described herein.

The embodiments set forth below represent the necessary information to enable those skilled in the art to practice the subject matter described herein and illustrate the best mode of practicing the subject matter described herein. Upon reading the following description in light of the accompanying drawing figures, those skilled in the art will understand the concepts of the subject matter described herein and will recognize applications of these concepts not particularly addressed herein. It should be understood that these concepts and applications fall within the scope of the disclosure and the accompanying embodiments.

Methods, systems, and computer-readable media for applying a force, such as an Acoustic Radiation Force (ARF), for example, to nondestructively measure physical properties of samples by observing induced displacements using different focal configurations are disclosed.

One embodiment, which is referred to herein as double-profile intersection (DoPlo) elastography, is an acoustic radiation force (ARF)-based ultrasonic imaging method that exploits the phenomenon of displacement underestimation in the ultrasonic tracking of acoustic radiation force responses to allow for the noninvasive, pointwise, and quantitative or qualitative measurement of tissue shear modulus.

DoPlo measures the displacement response of tissue due to a focused acoustic radiation force (ARF) and superposes displacement profiles made with two different aperture configurations. By superposing the displacement profiles with varying degrees of displacement underestimation, a time-point can be found that is characteristic of a given distance from an ARF excitation, tracking focal combination, and shear modulus. This time of intersection (TI) can be passed through an empirically-derived model to infer a shear modulus of individual resolution cells. Comparing the shear modulus of homogeneous, isotropic, and elastic material using finite-element simulations as well as commercially available and custom-made gelatin phantoms, comparable shear modulus estimates were measured, with an average estimate error of roughly 10% in silico. DoPlo is a novel technique to measure tissue elasticity with improved lateral resolutions compared to existing methods.

DoPlo interrogates the mechanical property of tissue within a resolution cell, the portion of the Point-Spread Function (PSF) with the dominant amount of signal energy. Following an ARFI excitation, the tissue's viscoelastic response is observed using more than one transducer focal configuration. While the ideal displacement measurement for a point of space in ARFI-excited tissue would reflect the true displacement of that point, this does not occur in practice; the resolution cell of a "point" of measurement covers a finite range of space: the resolution cell. As a result, two identical displacements of the same small area of tissue can be recorded as having "different" displacements by taking measurements using two different F-numbers.

The converse also holds true. The interrogation of an identical, small region of tissue using ultrasonic displacement tracking through different apertures encode information on the tissue's mechanical properties, and this difference in displacement underestimation for two different F-numbers encodes information on the mechanical properties of tissue within the resolution cells of the two measurements.

FIG. 1 is block diagram illustrating a system for nondestructively measuring physical properties of samples by observing induced displacements using different focal configurations, according to some embodiments of the subject matter described herein. In the embodiment illustrated in FIG. 1, the system includes a subsystem for interrogation (force generation) 100, a subsystem for motion dynamics observation 102, a subsystem for displacement calculation 104, a subsystem for implementing a parameter calculation 106, and a subsystem for producing and/or displaying the output 108.

The interrogation subsystem 100 may use ARF, a magnetic field, a mechanical indentation, and/or other means to cause a displacement within the material sample. In the embodiment illustrated in FIG. 1, the interrogation subsystem 100 produces a sequence of one or more forces directed towards a material sample according to an interrogation profile that defines a focal configuration.

As used herein, the term "focal configuration" refers to the ratio of the focal depth (z) over the transmitting aperture size (D). It can be defined in the lateral or in the elevational dimension. The term is used to indicate the size of the transmitted beam at the focal depth in the lateral or elevational dimension independent of the transmitted center wavelength. The overall size of the transmitted beam at the focal depth is lambda*z/D, where lambda is the center wavelength, z if the focal depth, and D is the size of the aperture in the lateral (or elevational) dimension. The focal configuration is z/D. A focal configuration used to provide a force (e.g., via ARF) is referred to as a "push focal configuration", and the interrogation itself may be referred to herein as "a push." A focal configuration used to observe a displacement (e.g., via ultrasound) is referred to as a "tracking focal configuration" and the observation itself may be referred to herein as "an observation."

In some embodiments, the interrogation profile may include other information about the force, including but not limited to, an amount, direction, and/or focal depth of each force in the sequence of forces, as well as the timing, duration, spacing, relaxation time, recovery time, etc., of each force in the sequence of forces.

The motion dynamics observation subsystem 102 may make measurements based on ultrasound, magnetic resonance imagery, optical input (such as but not limited to pictures, videos, etc., including from high-speed cameras), optical coherence tomography, using a mechanical means, such as but not limited to a micrometer, and/or other means to observe the displacement caused by the interrogation of the sample. It should be noted that the angles of the forces and measurements with respect to the sample as shown in FIG. 1 were chosen for illustration purposes only and are not intended to convey any particular orientation.

The displacement calculation subsystem 104 receives data produced by the motion dynamics observation subsystem 102 and calculates displacement of the sample. In the embodiment illustrated in FIG. 1, the displacement calculation subsystem 104 receives data from each measurement and calculates an observed displacement of the sample for each measurement. The measured displacements are then sent to the parameter calculation subsystem 106.

The parameter calculation subsystem 106 receives displacement information (e.g., the measured displacements) from the displacement calculation subsystem 104, and may optionally receive information about the push focal configuration(s) and the tracking focal configuration(s). and uses all or a portion of that information as inputs into an equation, Machine Learning (ML) model, etc., to calculate or predict certain parameters or material properties/material characteristics, such as elasticity and viscosity of the sample. The parameter calculation subsystem 106 produces as output values of the physical parameters of the material sample, such as the elasticity/viscosity of the material sample. In the embodiment illustrated in FIG. 1, the result(s) of the parameter calculation is provided to the output subsystem 108.

The output/display subsystem 108 presents the results of the parameter calculation to the user. In the embodiment illustrated in FIG. 1, the output/display subsystem 108 produces a "heat map" 110 showing the values of the measured parameter at different locations (depth, lateral distance from centerline) of the measured sample. The output/display subsystem 108 may present the physical parameter data in other forms, such as text, tables, graphs, 3D plots, histograms, and so on.

Each of the systems, subsystems, or modules described herein may comprise processing circuitry. Processing circuitry may comprise a combination of one or more of a microprocessor, a controller, a microcontroller, a Central Processing Unit (CPU), a Digital Signal Processor (DSP), an Application Specific Integrated Circuit (ASIC), a Field Programmable Gate Array (FPGA), or any other suitable computing device, resource, or combination of hardware, software, and/or encoded logic operable to provide, either alone or in conjunction with other components, such as the device readable medium 1080, system functionality. For example, the processing circuitry may execute instructions stored in a device readable medium or in memory within and/or coupled to the processing circuitry. Such functionality may include providing any of the various features, functions, or benefits discussed herein. In some embodiments, the processing circuitry may include a System on a Chip (SOC).

Figure 2:
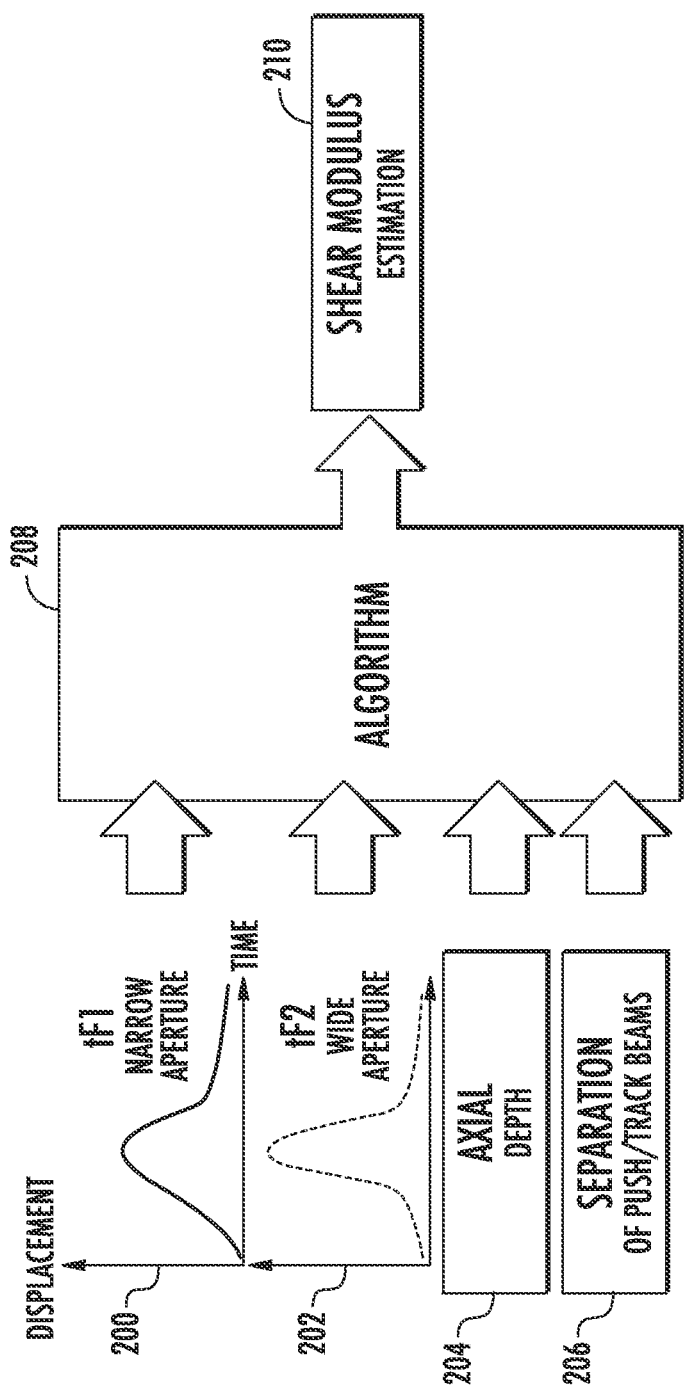
FIG. 2 illustrates a method for nondestructively measuring physical properties of samples by observing induced displacements using different focal configurations according to some embodiments of the present disclosure.

FIG. 2 illustrates a method for nondestructively measuring physical properties of samples by observing induced displacements using different focal configurations according to some embodiments of the present disclosure. In the embodiment illustrated in FIG. 2, the method includes interrogating a material sample using a single push focal configuration and recording a set of two or more displacement profiles 200 and 202, each being measured with different tracking focal configurations tF1 and tF2, respectively.

The displacement profiles contain information about displacement of portions of the interrogated sample over time, e.g., in response to the interrogation by ARF or other means. Although displacement profiles contain information about displacement of various sub-volumes within the larger volume of material being interrogated, for simplicity of description, displacement profiles are shown in the instant application as simple graphs of displacement over time, such as the displacement measurements 200 and 202 in FIG. 2.

In the embodiment illustrated in FIG. 2, the displacement profiles 200 and 202, as well as information about interrogation, such as axial depth 204, separation of the push and track beams 206, or other information from the push configuration, are provided to an algorithm 208. The algorithm 208 calculates an output 210, which in the embodiment illustrated in FIG. 2 is a physical parameter of the interrogated material, such as, but not limited to, a shear modulus. In this manner, a physical characteristic of the material sample is determined based on a comparison of the first and second displacements over time of the material sample.

Thus, in some embodiments, DoPlo involves the detection of displacement profiles at identical spatial positions following a displacement using an identical push/tracking configuration but with different tracking F-numbers, the resultant displacement being at some distance away from the region of excitation (RoE). The two profiles are superposed onto each other, and common features that are inferred from the two profiles are programmatically detected by an algorithm. These features, in turn, are converted into a shear modulus estimate for that point of space. The shear modulus values for all points may then be assembled into a single elastography image.

Examples of push techniques include, but are not limited to, use of ARF, magnetic fields, and mechanical indenter.

Examples of tracking techniques include, but are not limited to, use of ultrasound, MRI, mechanical micrometer, and optical methods such as using an optical microscope and Optical Coherence Tomography (OCT). In the embodiments where different tracking focal configurations are used, MRI can be used, even though MRI does not use apertures per se, because the region over which the displacement measured could be larger or smaller, so MRI can be used for tracking regardless of whether two different push focal configurations are used or not.

Basic Method

Figure 3:
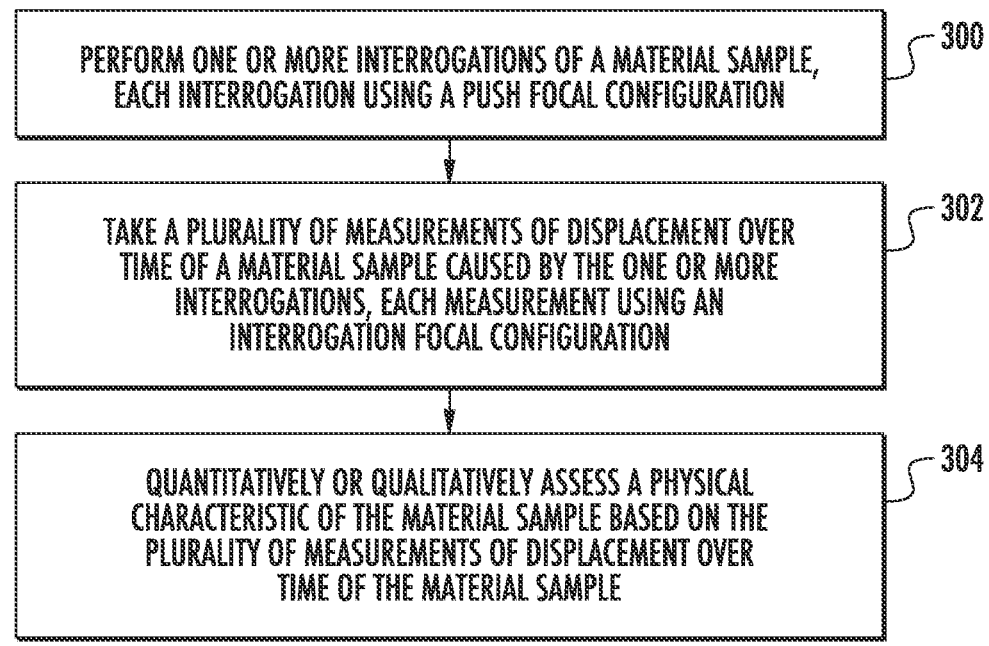
FIG. 3 illustrates a method for measuring a physical characteristic of a material according to some embodiments of the present disclosure, in which the displacement profiles are measurements taken after a single interrogation.

FIG. 3 illustrates a method for measuring a physical characteristic of a material according to some embodiments of the present disclosure, in which the displacement profiles are measurements taken after a single interrogation. In the embodiment illustrated in FIG. 3, the process includes the following steps:

Step 300: Perform one or more interrogations of a material sample, each interrogation using a push focal configuration. In embodiments where there is one interrogation, one push focal configuration will be used. Where there are multiple interrogations, in some embodiments the multiple interrogations will use the same push focal configuration, and in other embodiments at least one of the multiple interrogations may use a different push focal configuration from another of the multiple interrogations.

Step 302: Take a plurality of measurements of displacement over time of the material sample caused by the one or more interrogations, each measurement using an interrogation focal configuration. In some embodiments the multiple measurements will use the same interrogation focal configuration, and in other embodiments at least one of the multiple measurements may use a different interrogation focal configuration from another of the multiple measurements.

For example, in one embodiment, a single push is followed by multiple measurements using different interrogation focal configurations. In another embodiment, a push-measure operation is performed multiple times, each time using a different push focal configuration, a different interrogation focal configuration, or both. These examples are illustrative and not limiting.

Step 304: Quantitatively or qualitatively assess a physical characteristic of the material sample based on the plurality of measurements of displacement over time of the material sample. Specifics about how the plurality of measurements of displacement over time may be used to quantitatively or qualitatively assess a physical characteristic of a material sample will be described in more detail in sections below.

One Push, Multiple Observations (Different Tracking Configurations)

Figure 4:
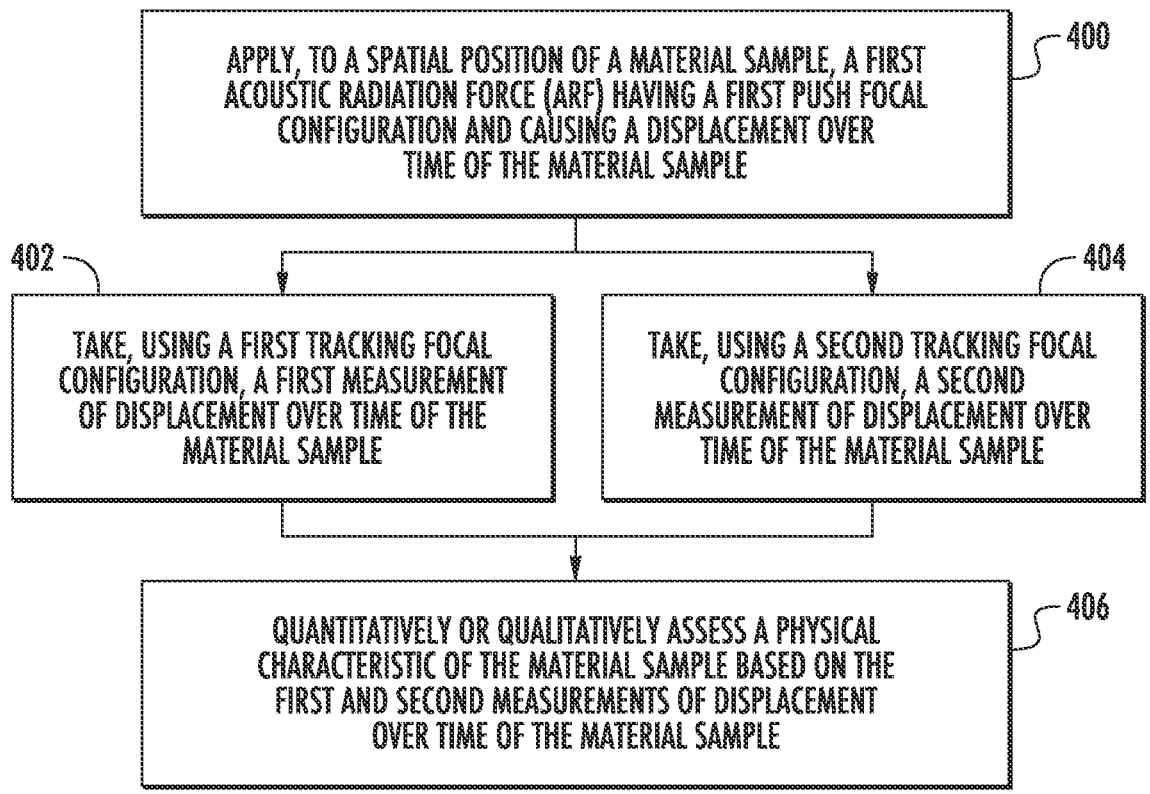
FIG. 4 illustrates a method for measuring a physical characteristic of a material according to some embodiments of the present disclosure, in which the displacement profiles are measurements taken after a single interrogation.

FIG. 4 illustrates a method for measuring a physical characteristic of a material according to some embodiments of the present disclosure, in which the displacement profiles are measurements taken after a single interrogation. In the embodiment illustrated in FIG. 4, the process includes the following steps:

Step 400: Apply, to a spatial position of a material sample, a first ARF having a push focal configuration and causing a displacement over time of the material sample.

Step 402: Take, using a first tracking focal configuration, a first measurement of displacement over time of the material sample.

Step 404: Take, using a second tracking focal configuration, a second measurement of displacement over time of the material sample.

Step 406: Quantitatively or qualitatively assess a physical characteristic of the material sample based on the first and second measurements of the displacement over time of the material sample.

In some embodiments, the measurements in steps 402 and 404 may be taken simultaneously or essentially simultaneously, e.g., using more than one confocal imaging probes, or by using plane wave image methods such that all tracking data are acquired using a single transducer at the same time, and then the channel data is used to beamform two different tracking focal configurations. Alternatively, the measurements in steps 402 and 404 may be taken sequentially in any order.

In alternative embodiments, the displacement profiles are measurements, each taken after its own separate interrogation.

Multiple Pushes (Same Push Configuration),
Multiple Observations (Different Tracking Configurations)

In some embodiments, a push using a push focal configuration is performed, followed by a first measurement using a first tracking focal configuration. A second push using the same push focal configuration is performed, followed by a second measurement using a second tracking focal configuration.

Figure 5:
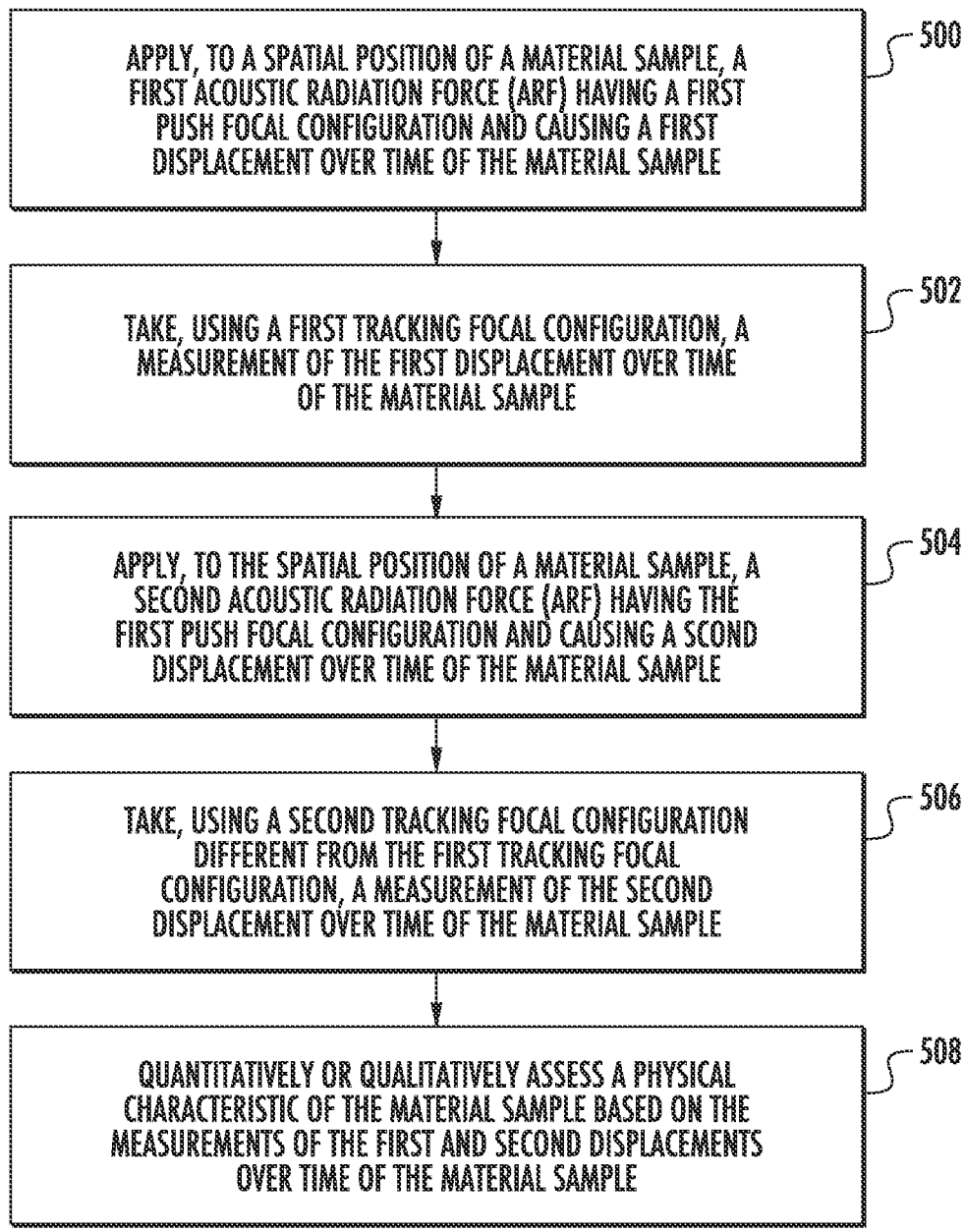
FIG. 5 illustrates a method for measuring a physical characteristic of a material according to some embodiments of the present disclosure, in which each displacement profile is a measurement taken after a corresponding one of a series of interrogations.

FIG. 5 illustrates a method for measuring a physical characteristic of a material according to some embodiments of the present disclosure, in which each displacement profile is a measurement taken after a corresponding one of a series of interrogations. In the embodiment illustrated in FIG. 5, the process includes the following steps:

Step 500. Apply, to a spatial position of a material sample, a first ARF having a first push focal configuration and causing a first displacement over time of the material sample.

Step 502. Take, using a first tracking focal configuration, a measurement of the first displacement over time of the material sample.

Step 504. Apply, to the spatial position of a material sample, a second ARF having the first push focal configuration and causing a second displacement over time of the material sample.

Step 506. Take, using a second tracking focal configuration, a measurement of the second displacement over time of the material sample.

Step 508. Quantitatively or qualitatively assess a physical characteristic of the material sample based on the measurements of the first and second displacements over time of the material sample.

Multiple Pushes (Different Push Configurations),
Multiple Observations (Same Tracking Configurations)

In some embodiments, a push using a first push focal configuration is performed, followed by a first measurement using a tracking focal configuration. A second push using a second push focal configuration is performed, followed by a second measurement using the same tracking focal configuration.

Figure 6:
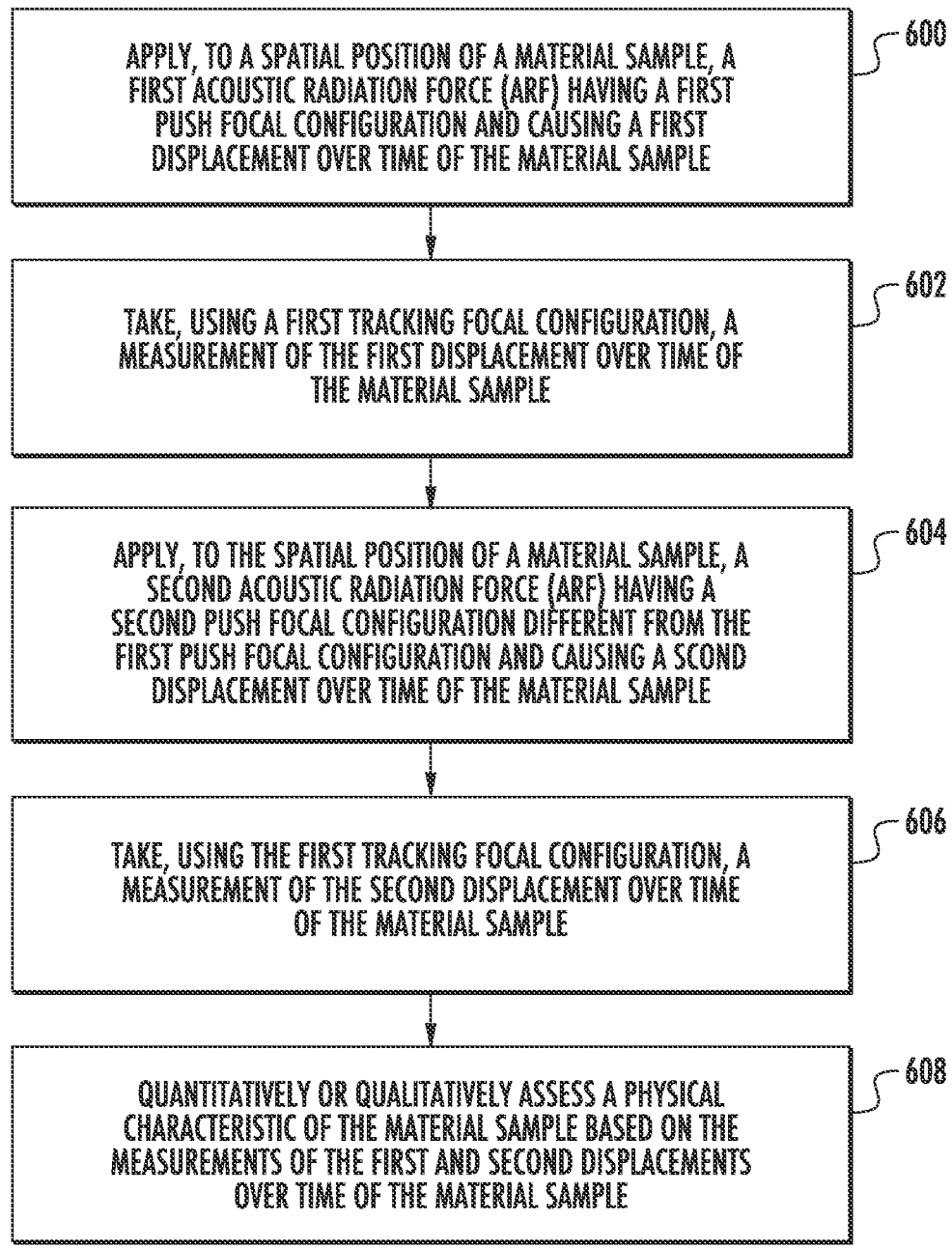
FIG. 6 illustrates a method for measuring a physical characteristic of a material according to some embodiments of the present disclosure, in which each displacement profile is a measurement taken after a corresponding one of a series of interrogations.

FIG. 6 illustrates a method for measuring a physical characteristic of a material according to some embodiments of the present disclosure, in which each displacement profile is a measurement taken after a corresponding one of a series of interrogations. In the embodiment illustrated in FIG. 6, the process includes the following steps:

Step 600. Apply, to a spatial position of a material sample, a first ARF having a first push focal configuration and causing a first displacement over time of the material sample.

Step 602. Take, using a first tracking focal configuration, a measurement of the first displacement over time of the material sample.

Step 604. Apply, to the spatial position of a material sample, a second ARF having a second push focal configuration different from the first push focal configuration and causing a second displacement over time of the material sample.

Step 606. Take, using the first tracking focal configuration, a measurement of the second displacement over time of the material sample.

Step 608. Quantitatively or qualitatively assess a physical characteristic of the material sample based on the measurements of the first and second displacements over time of the material sample. This step is essentially identical to step 508 in FIG. 5.

Multiple Pushes (Different Push Configurations),
Multiple Observations (Different Tracking Configurations)

In some embodiments, a push using a first push focal configuration is performed, followed by a first measurement using a first tracking focal configuration. A second push using a second push focal configuration is performed, followed by a second measurement using a second tracking focal configuration.

Figure 7:
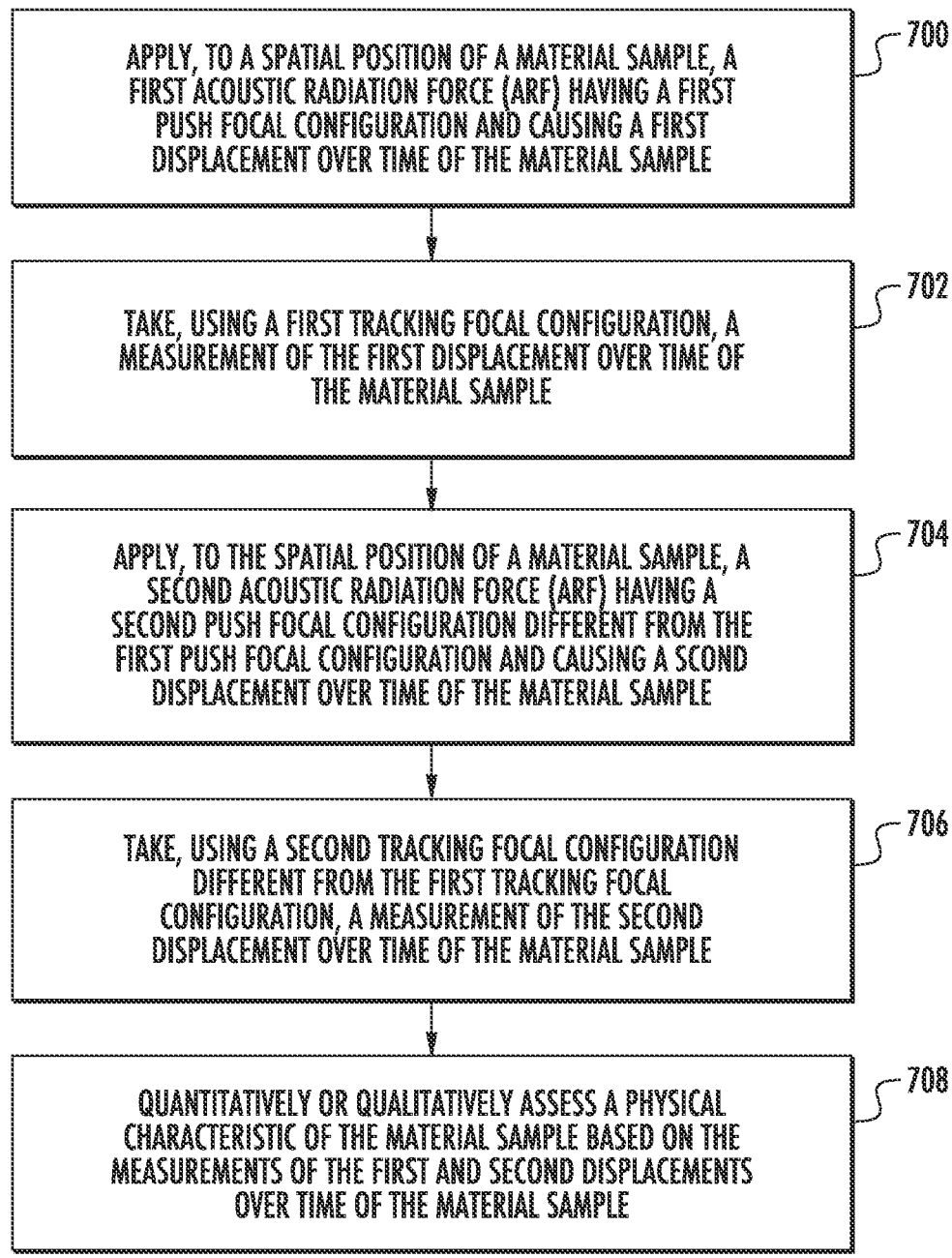
FIG. 7 illustrates a method for measuring a physical characteristic of a material according to some embodiments of the present disclosure, in which each displacement profile is a measurement taken after a corresponding one of a series of interrogations.

FIG. 7 illustrates a method for measuring a physical characteristic of a material according to some embodiments of the present disclosure, in which each displacement profile is a measurement taken after a corresponding one of a series of interrogations. In the embodiment illustrated in FIG. 7, the process includes the following steps:

Step 700. Apply, to a spatial position of a material sample, a first ARF having a first push focal configuration and causing a first displacement over time of the material sample.

Step 702. Take, using a first tracking focal configuration, a measurement of the first displacement over time of the material sample.

Step 704. Apply, to the spatial position of a material sample, a second ARF having a second push focal configuration different from the first push focal configuration and causing a second displacement over time of the material sample.

Step 706. Take, using a second tracking focal configuration different from the first tracking focal configuration, a measurement of the second displacement over time of the material sample.

Step 708. Quantitatively or qualitatively assess a physical characteristic of the material sample based on the measurements of the first and second displacements over time of the material sample. This step is essentially identical to step 508 in FIG. 5.

Experimental Methods—in Silico Model

Using the Finite-Element Modeling (FEM) software LS-DYNA, MATLAB, and an acoustic intensity map generated by the linear ultrasound simulator Field-II, a batch of simulations were conducted where a focused ARFI pulse pressed against a block of Homogeneous, Isotropic, and Elastic (HIE) tissue and caused displacement responses to be produced. The cell and node spacing, simulation timesteps, and non-mechanical material properties were predefined. A field of sub-resolution-cell particles made of acoustically scattering media, or "scatterers", were superposed onto each node in the dynamics calculations' output with a density of 21 scatterers per resolution cell. The positions of those scatterers were periodically tracked using a 25 kHz Pulse-Repetition Frequency (PRF) using Field-II. A normalized cross-correlation operation was applied to 3.5 ms (22 frames) of Radio-Frequency (RF) data with respect to a pre-displacement reference RF line, and the peak correlation in each axial depth within a 80 um search window for a 2-lambda kernel was transcribed as the displacement at each PRF timepoint. The aforementioned steps were taken using a virtual transducer replicating the Siemens Acuson VF 7-3 model.

Once the RF data were collated into displacements, the displacement profiles for two different F-numbers (i.e., the tracking F-number combination, or tFc) were upsampled by a factor of 10 using a piecewise cubic Hermite interpolating polynomial function, and superposed onto each other. The intersection of the two profiles, as determined by projecting them onto a homogeneous coordinate system, were found and inputted into a lookup table of coefficients for a linear fit function based on intersection times in HIE materials. A visual summary of the model-building process is outlined in FIG. 7.

Figure 8:
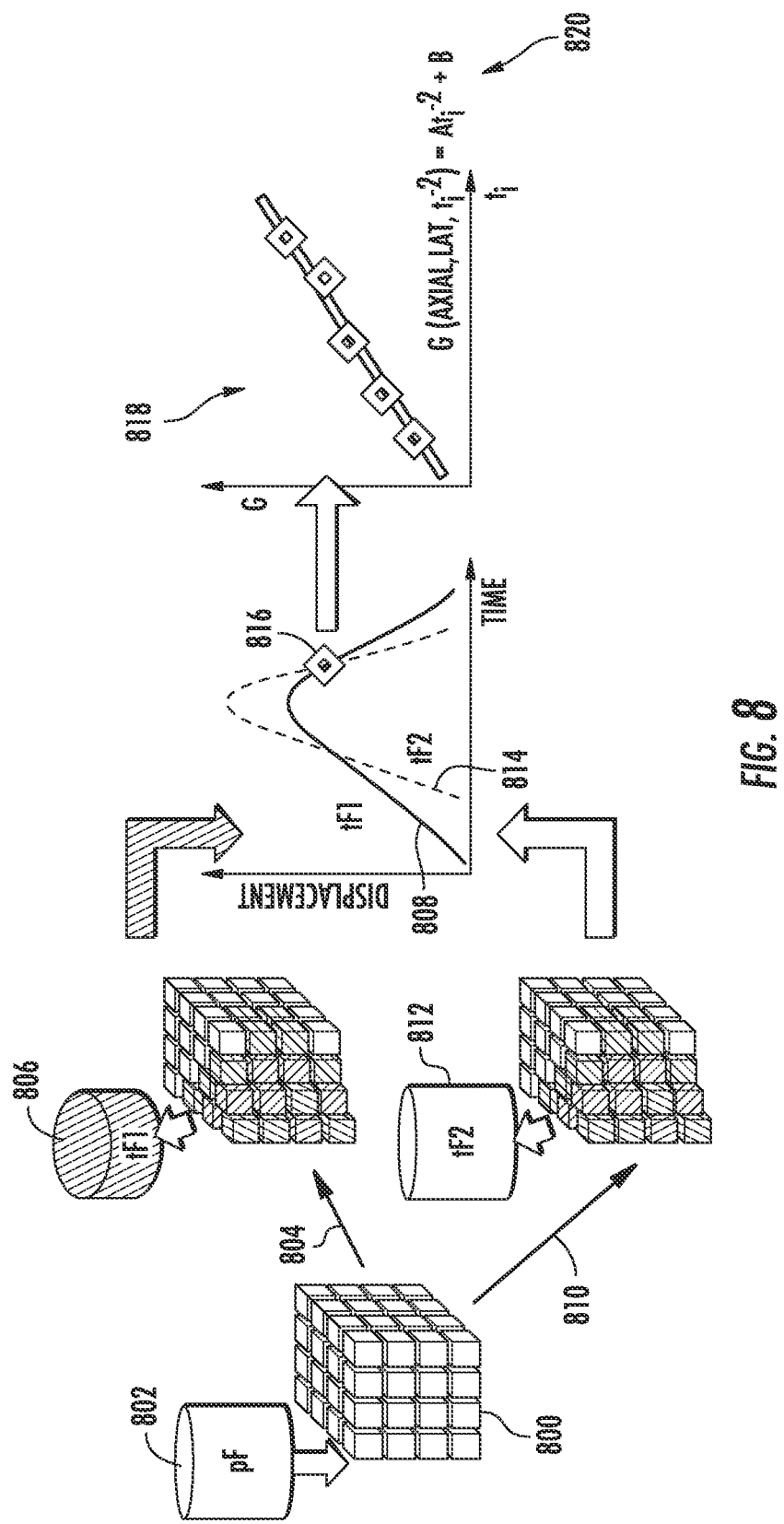
FIG. 8 visually illustrates a process for developing a Look-Up Table (LUT) for shear modulus estimation according to some embodiments of the present disclosure.

FIG. 8 visually illustrates a process for developing a Look-Up Table (LUT) for shear modulus estimation according to some embodiments of the present disclosure. In the embodiment illustrated in FIG. 8, the model is generated by using LS-DYNA and Field II to simulate ARF excitation in a HIE material 800 with a known shear modulus. The excitation 802 is performed multiple times, each time using a push F-number (pF) of 1.5, but tracked using different tracking F-numbers (tFs). In the embodiment illustrated in FIG. 8, the first excitation 804 is tracked 806 using tF1 to create a first Displacement Profile (DP) 808. The second excitation 810 is tracked 812 using tF2 to create a second DP 814. DoPlo is performed on the generated DP for all possible tFc to generate an intersection time 816 for each spatial position, shear modulus, and tFc. For each tFc, the intersection times ($t_{int}$) 818 at each position are compiled for each shear modulus simulated, and a polynomial fit model 820 is generated; this process is repeated for each simulated position and tFc. In some embodiments, the linear fit function converts $t_{int}$ to shear modulus as a function of tFc, $t_{int}$, axial depth, and push/track separation. The fit models generated in are compiled into a LUT to allow for the conversion of any arbitrary intersection value in a given spatial position to a modulus estimate.

Results

Figure 9:
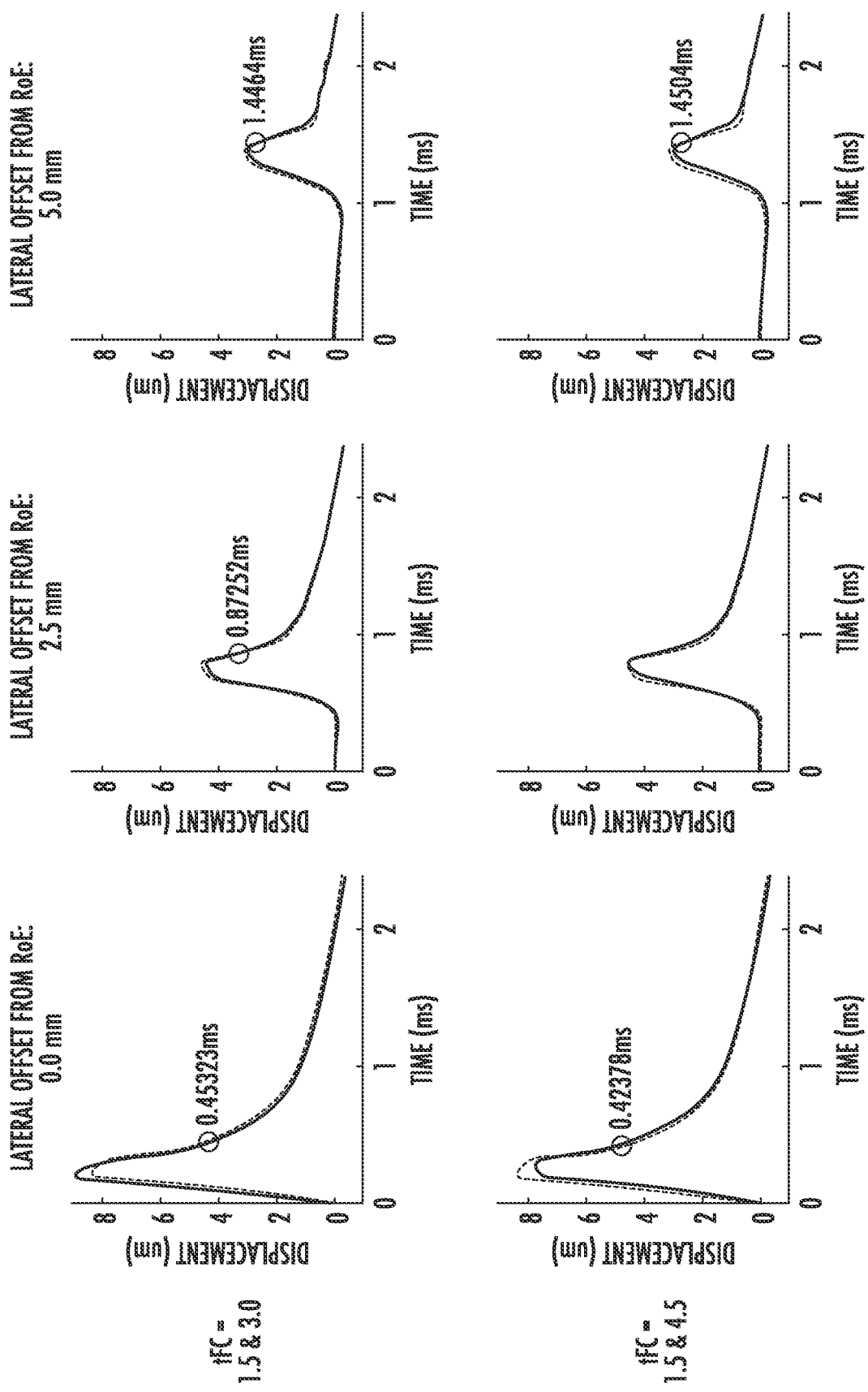
FIG. 9 depicts representative examples of simulated DoPlo profiles, or the superposition of two ARFI-induced displacement profiles with different focal configurations, at various aperture combinations and lateral distances from the Region of Excitation (RoE) according to some embodiments of the subject matter described herein.

FIG. 9 depicts representative examples of simulated DoPlo profiles, or the superposition of two ARFI-induced displacement profiles with different focal configurations, at various aperture combinations and lateral distances from the Region of Excitation (RoE). The corresponding time where the profiles intersect are also annotated, as well as the original FEM displacement from which the ultrasonic tracking is based. The top row shows results using tFc values of 1.5 and 3.0, and the bottom row shows results using tFc values of 1.5 and 4.5. The left column shows results measured at the same lateral position as the RoE, the middle column shows results measured at a 2.5 mm lateral offset from the position of the RoE, and the right column shows results measured at a 5.0 mm lateral offset from the position of the RoE. All displacements were measured at the focal depth of 25 mm in a FEM simulation of a HIE material with shear modulus of 17 kPa, based off of a pF # of 1.5.

Figure 10C:
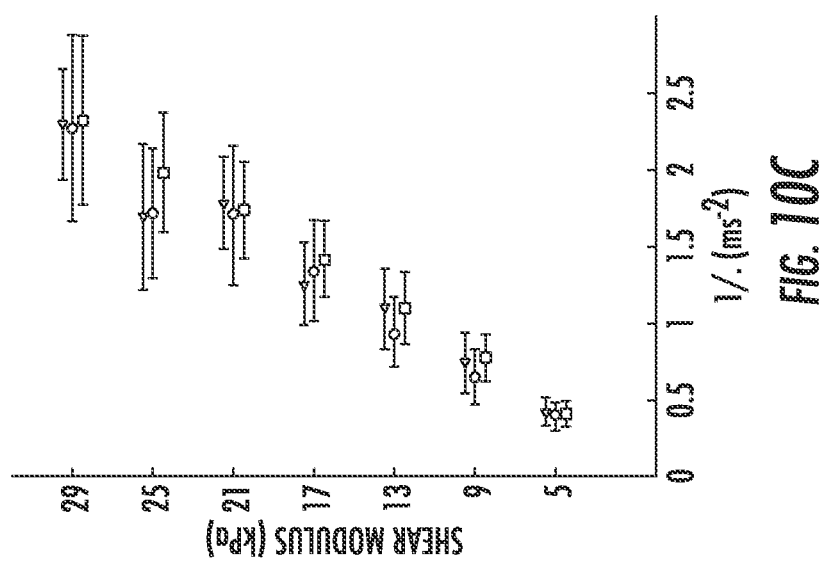
FIGS. 10A-10C illustrate Intersection time values that were generated in silico at various spatial positions and shear modulus according to some embodiments of the subject matter described herein.
Figure 10A:
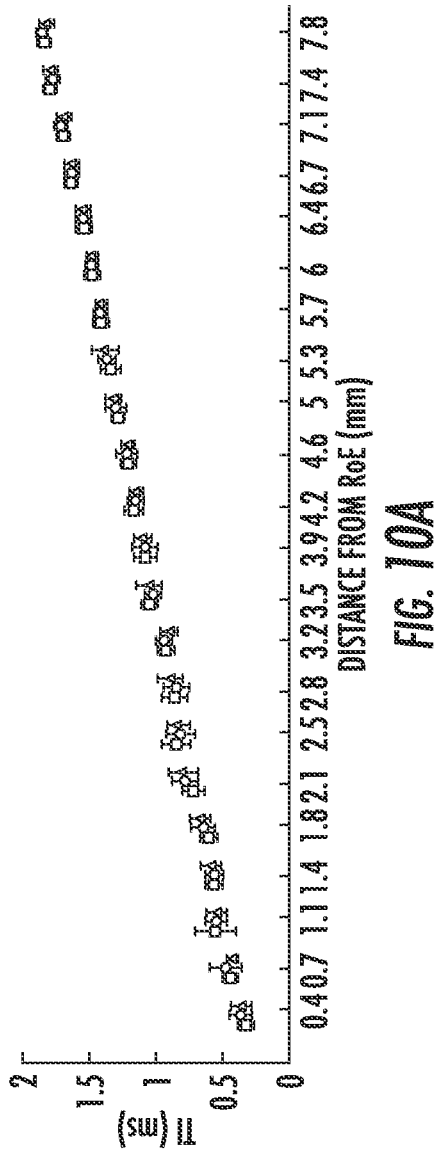
Figure 10B:
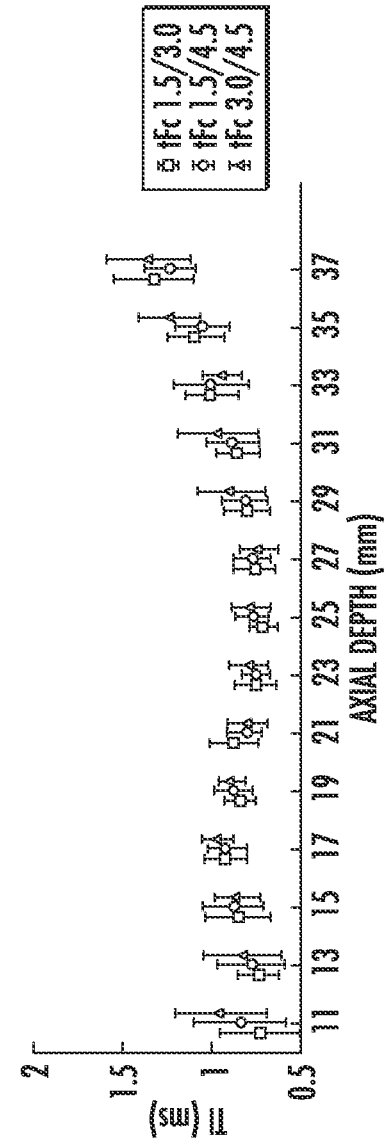
Figure 11A:
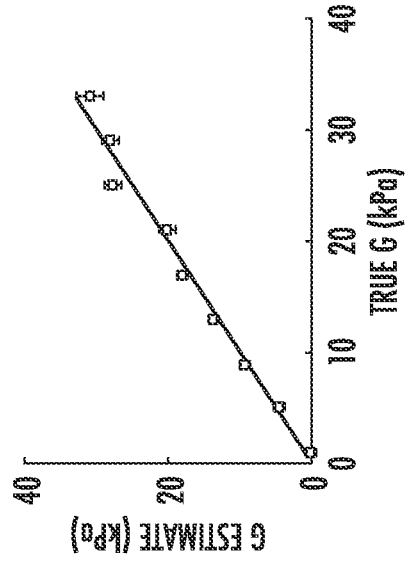
FIGS. 11A-11F illustrate graphs comparing true versus DoPlo-estimated shear modulus in simulated Homogeneous, Isotropic, and Elastic (HIE) material according to some embodiments of the subject matter described herein.
Figure 11C:
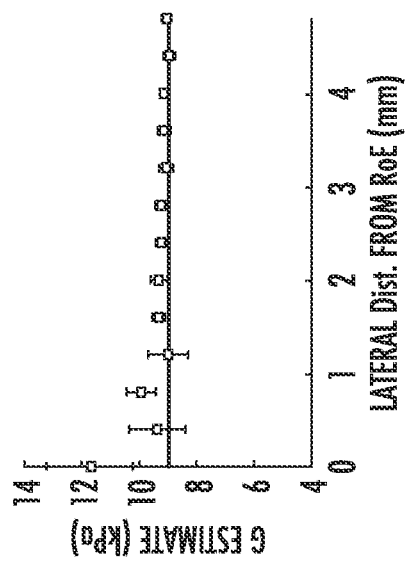
Figure 11E:
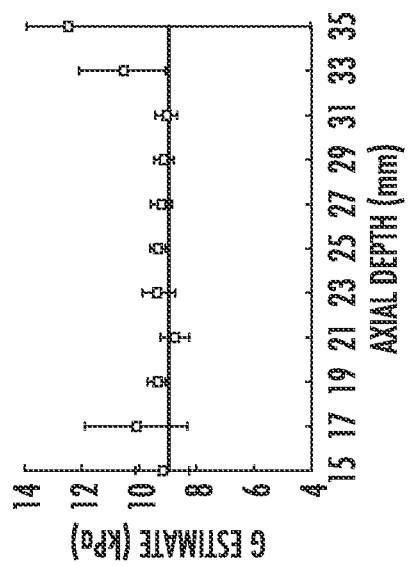
Figure 11B:
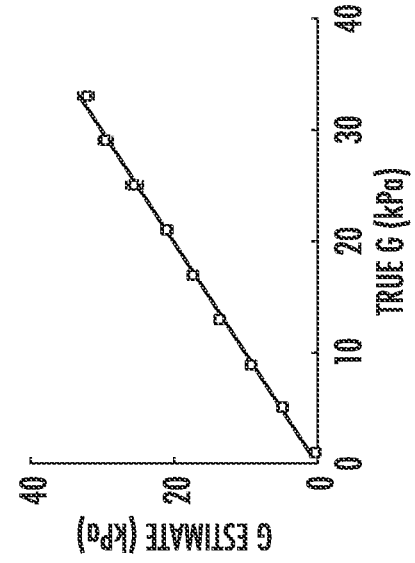
Figure 11D:
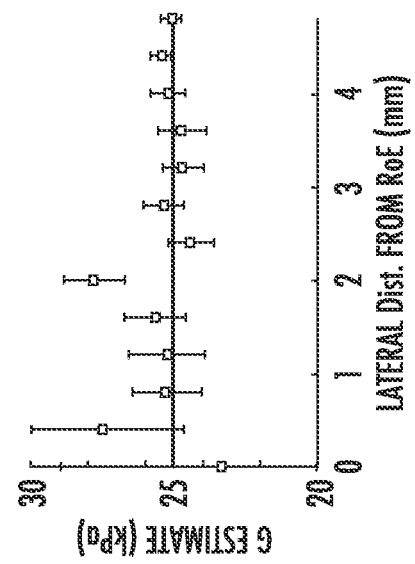
Figure 11F:
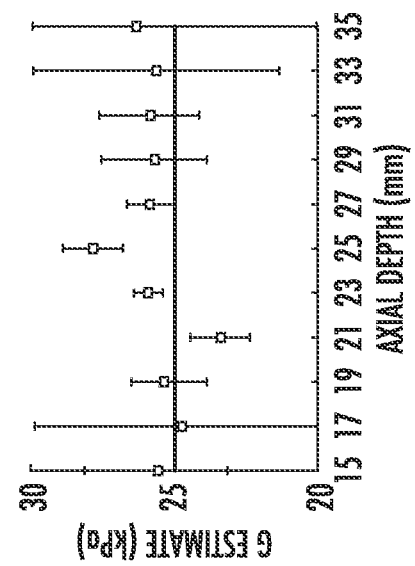

FIGS. 10A-10C illustrate Intersection time values that were generated in silico at various spatial positions and shear modulus, example distributions based off of the mean and standard deviation of 10 speckle realizations at 31 scatterers per resolution cell. FIGS. 10A-10C show distribution of intersection times (TI) measured across (FIG. 10A) various lateral positions at the focal depth and (FIG. 10B) various axial positions at a lateral position of 2.0 mm. All measurements used a pF# of 1.5. Measurements variously used a tFc of 1.5 and 3 (squares), 1.5 and 4.5 (circles), and 3 and 4.5 (triangles). The simulated acquisitions were from HIE material, and were measured at a focal depth of 25 mm with a shear modulus of 25 kPa. Using this and other simulated materials of varying shear moduli, (FIG. 10C) the inverse-square of the intersection time was related to the intended shear modulus, and a linear fit was applied; the coefficients from this fit model was used to relate the intersection times to the shear modulus of the HIE material for the specific position, at the focal depth and 2.0 mm away from the RoE.

The simulation-derived intersection times for three different tFc were converted into a linear fit model at a lateral range from 0 mm to 5 mm from the RoE, as well as 15 mm to 35 mm in the axial direction. The resulting estimated shear modulus was compared for multiple spatial positions and stiffnesses; the results are shown in FIGS. 11A-11F.

FIGS. 11A-11F illustrate graphs comparing true versus DoPlo-estimated shear modulus in simulated HIE material (FIG. 11A) 2.0 mm laterally from the RoE at the focal depth of 25 mm, and (FIG. 11B) 5.0 mm laterally from the RoE at a depth of 20 mm. The (FIGS. 11C and 11D) lateral and (FIGS. 11E and 11F) axial distributions of shear modulus estimates are also displayed for a simulated material with true shear modulus of (FIGS. 11C and 11E) 9 kPa and (FIGS. 11D and 11F) 25 kPa.

Figure 12:
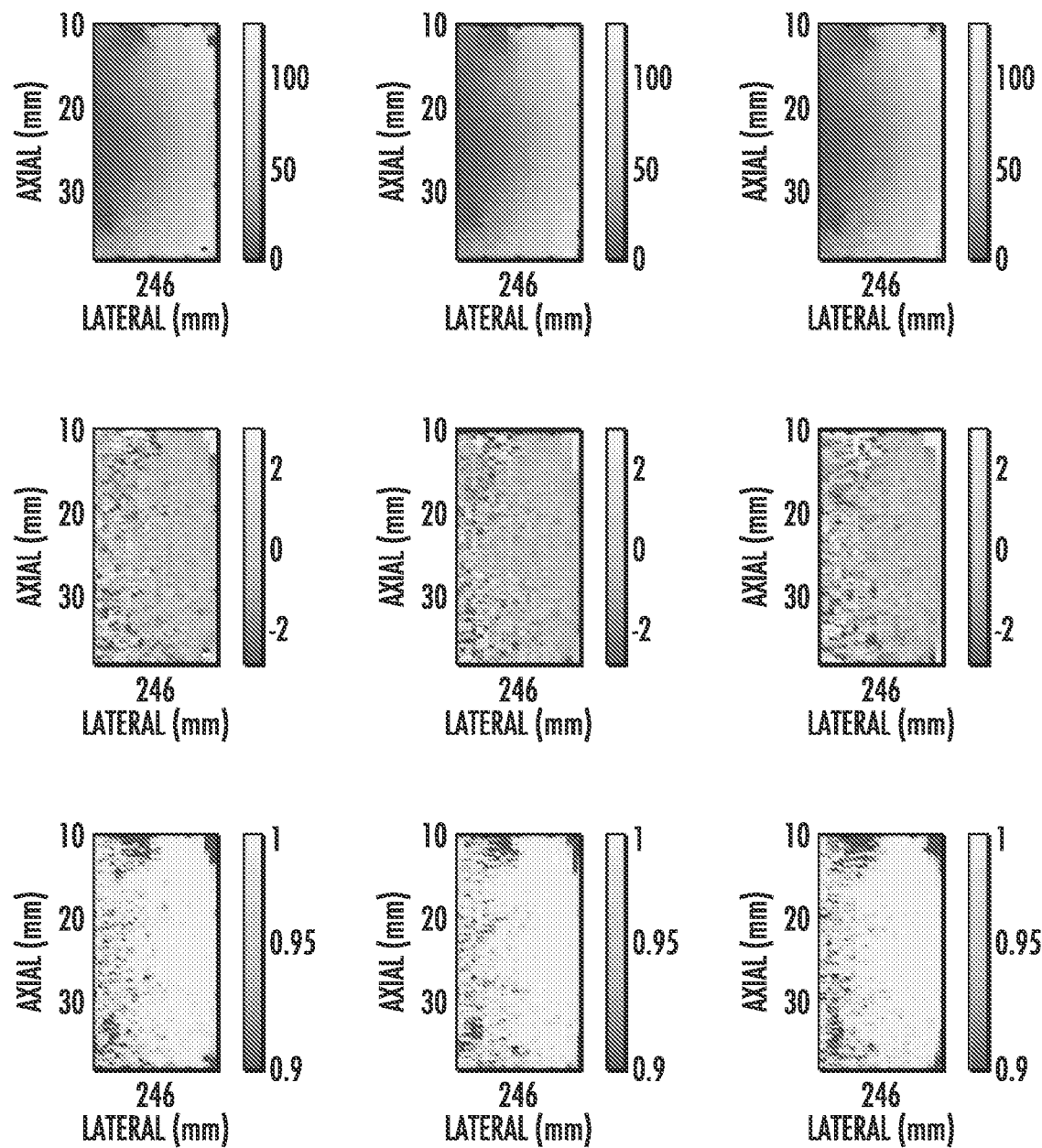
FIG. 12 illustrates the distribution of coefficients demonstrated in FIGS. 10A-10C for all positions.

FIG. 12 illustrates the distribution of coefficients demonstrated in FIGS. 10A-10C for all positions. FIG. 12 shows the distribution of the slope (row 1), intersect coefficients (row 2) and R2 value (row 3) from a linear fit of the FEM-based shear modulus of HIE materials as a function of the inverse-square of simulated intersection times, as measured using tFc of 1.5 and 3 (column a), 1.5 and 4.5 (column b), and 3 and 4.5 (column c).

Using this calibration model, shear modulus estimates were generated in a custom-made elasticity phantom with a background Young's modulus of 24 kPa and an inclusion with Young's modulus of 9 kPa (i.e., shear modulus of 8 kPa and 3 kPa, respectively). The resultant DoPlo images, compared against ARFI peak displacements, and Shear-Wave Elasticity Imaging (SWEI), are depicted and analyzed in FIGS. 13A-13D.

Figure 13:
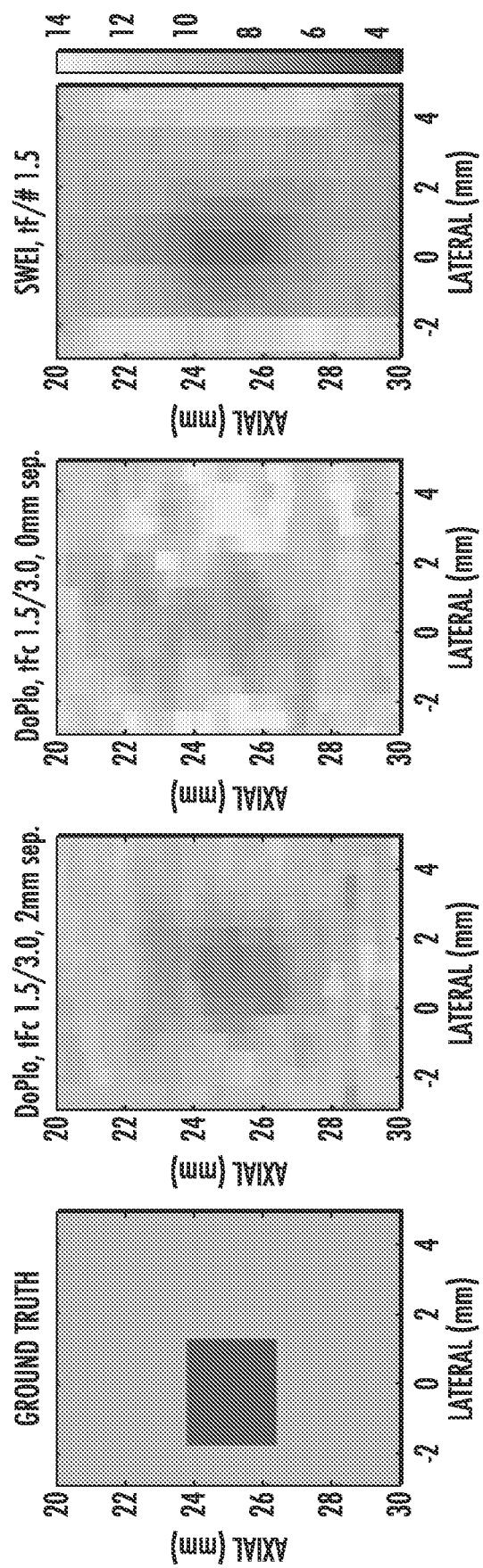
FIGS. 13A-13D illustrate a comparison of images of a simulated elasticity phantom using multiple imaging modalities.

FIGS. 13A-13D illustrate a comparison of images of a simulated elasticity phantom using multiple imaging modalities. The phantom comprises of a background material with a shear modulus of 10 kPa and a very long bar with a 2.50 mm square cross-section inclusion with a shear modulus of 5 kPa; the intended layout is depicted in (FIG. 13A). Images were acquired using (FIG. 13B) DoPlo with times-intersect measured from the time of ARF excitation at 2.0 mm away from the push beam, (FIG. 13C) likewise but on-axis to the push beam with the time-intersect defined with respect to the time point of the later peak displacement out of the two displacement profile graphs, and (FIG. 13D) SWEI.

Anisotropy

The techniques described above for observing induced displacements using different focal configurations may be also used to quantitatively determine material anisotropy.

Figure 14:
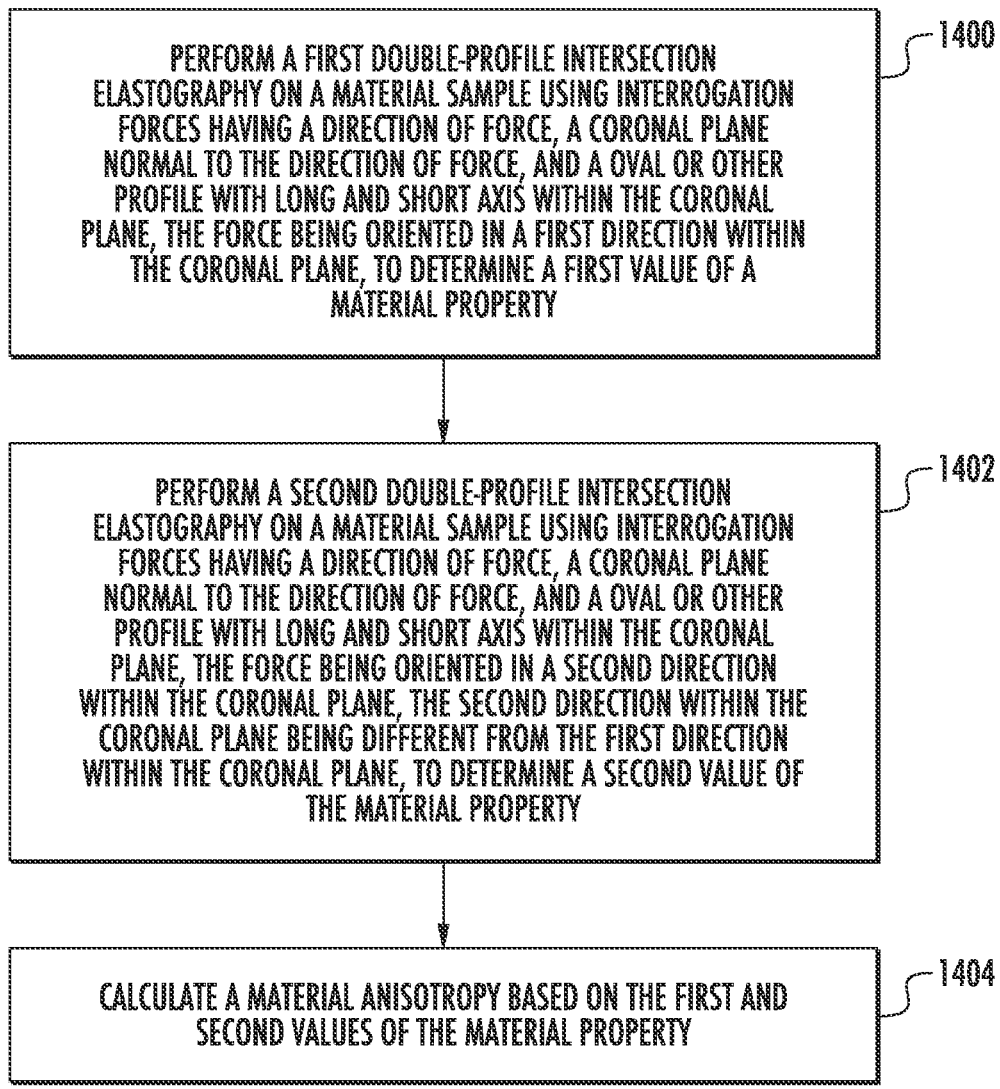
FIG. 14 illustrates a method for determining material anisotropy according to some embodiments of the present disclosure.

FIG. 14 illustrates a method for determining material anisotropy according to some embodiments of the present disclosure. In the embodiment illustrated in FIG. 14, the method includes performing multiple double-profile intersection elastographies on a material sample, where for each performance, the force(s) being applied have a direction (e.g., into the material sample), have a coronal plane normal to the direction of the first force, and have an oval or other profile with long and short axes within the coronal plane. The difference, if any, between the calculated material property value in the first direction and the calculated material property value in the second direction is an indication of the anisotropy of the material.

In the embodiment illustrated in FIG. 14, the method includes the following steps:

Step 1400: perform a first double-profile intersection elastography on a material sample, with the long axis of the force being oriented in a first direction within the coronal plane, to determine a first value for the material property being measured (e.g., viscosity, elasticity, etc.).

Step 1402: perform a second double-profile intersection elastography on the material sample, with the long axis of the force being oriented in a second direction within the coronal plane different from the first direction, to determine a second value for the material property being measured. In some embodiments, the first direction and the second direction may be presumed to be 90 degrees apart, but the same technique works for any arbitrary angle, such as when physical or environmental constraints make it difficult or impossible to get two readings that are 90 degrees apart in orientation.

Step 1404: calculate a material anisotropy of the material property being measured based on the determined first and second values. In some embodiments, the angles of orientation may also be part of the calculation. The quantitative anisotropy can be calculated based on the calculated material property value in the first direction and the calculated material property value in the second direction.

The double-profile intersection elastographies performed above may be performed according to any of the methods described herein and/or illustrated in FIGS. 3-7.

In some embodiments, for example, a method for measuring anisotropy would involve measuring elasticity (and/or viscosity) in one direction and the rotating the pushing and tracking beams to measure the elasticity (and viscosity) in a different direction. The method of rotation could be physical or electronic, depending on the type of transducer that is implemented. The degree of rotation could be 90, or smaller, or larger.

Results

It was demonstrated that DoPlo is capable of differentiating the shear modulus of elastic materials. Using an FEM-derived lookup table, the intersection of displacement profiles using two known focal configurations for a known axial position and push/track beam separation were converted into shear modulus estimates.

As DoPlo takes advantage of shear wave propagation far away from the RoE, detecting intersections of displacement profiles are only useful when displacement measurements are not overwhelmed by phenomena such as electronic noise, motion artifacts, jitter, and, most importantly, shear wave dispersion and attenuation. As SWEI shear wave velocity measurements are equally dependent on robustness against those factors, the useful lateral range from the RoE for DoPlo is comparable to that of SWEI. However, it is critical to recall that SWV reconstruction requires that the assumption that the entire region where the shear wave is being tracked is homogeneous. While this may be suitable for observing the bulk effects of tissue within the PSF of a single tracking beam, assuming that an area of tissue is homogeneous across a lateral span of millimeters leads to failure in resolving finer features. As such, the capability to take pointwise measurements of tissue stiffness that eliminates the need for spatial sampling may be diagnostically relevant.

Each of the systems, subsystems, or modules described herein may comprise processing circuitry. Processing circuitry may comprise a combination of one or more of a microprocessor, a controller, a microcontroller, a Central Processing Unit (CPU), a Digital Signal Processor (DSP), an Application Specific Integrated Circuit (ASIC), a Field Programmable Gate Array (FPGA), or any other suitable computing device, resource, or combination of hardware, software, and/or encoded logic operable to provide, either alone or in conjunction with other components, such as the device readable medium 1080, system functionality. For example, the processing circuitry may execute instructions stored in a device readable medium or in memory within and/or coupled to the processing circuitry. Such functionality may include providing any of the various features, functions, or benefits discussed herein. In some embodiments, the processing circuitry may include a System on a Chip (SOC).

Additional Embodiments

Figure 15:
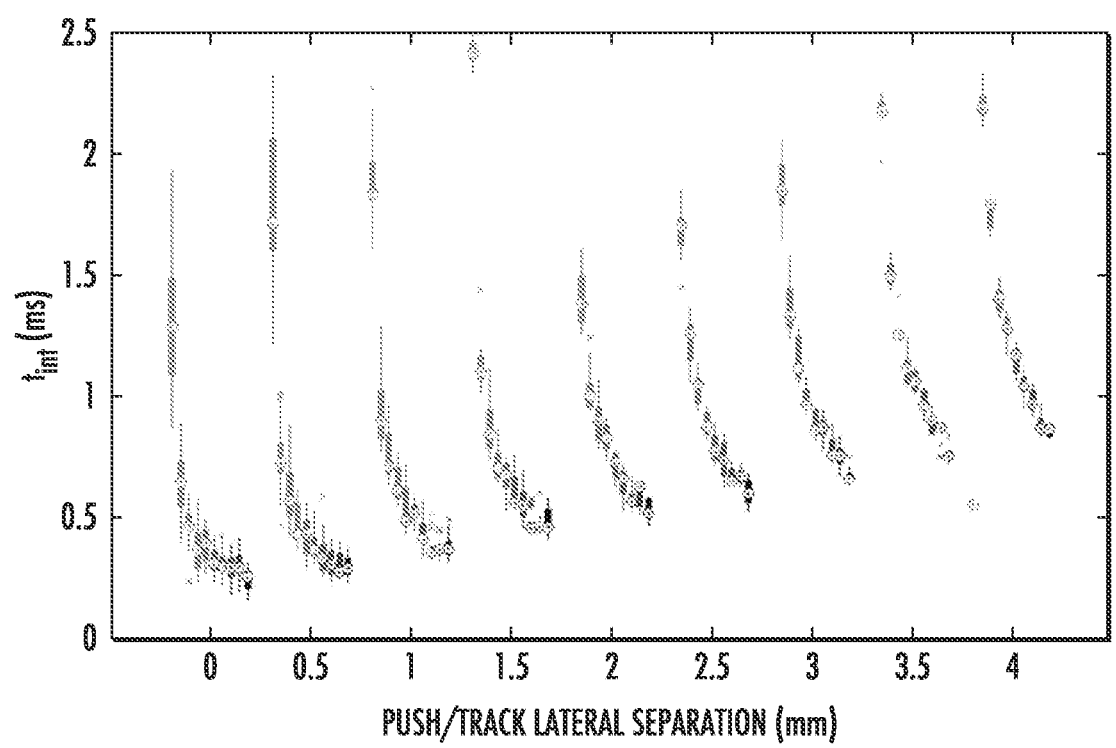
FIG. 15 illustrates box-whisker plots of times-intersect of different materials denoting the mean, interquartile range, and 95% confidence interval across 10 scatterer realizations, where the plots are ordered from those measured in a material with shear moduli of 1 kPa (pink; left) to 37 kPa (black; right) in 4 kPa increments.

In some of the examples described above, double-profile intersection elastography is used to quantitively assess a characteristic of a material by relating displacement measurements obtained with different transducer focal configurations to quantified models of material characteristics, such as elastic modulus. In an alternate embodiment of the subject matter described herein, measurements obtained with different transducer focal configurations (push focal configurations and/or tracking focal configurations) may be used to qualitatively assess differences in material characteristics. FIG. 15 depicts the potential of qualitatively differentiating softer from stiffer materials based on the magnitude of times-intersect measured from two displacement profiles at an axial depth of 25 mm (i.e. focal depth of the ARF excitation and tracking beams). For each push-track separation, times-intersect, depicted as box-whisker plots denoting the mean, interquartile range, and 95% confidence interval across 10 scatterer realizations, are ordered from those measured in a material with shear moduli of 1 kPa (pink; left) to 37 kPa (black; right) in 4 kPa increments. In each push-track separation, it can be seen that times-intersect measured in softer materials have a higher value compared to stiffer ones, and a nonlinear trend is visible.

Thus, in addition to quantitatively assessing a characteristic of a sample by relating displacement measurements obtained with different transducer focal configurations to numeric measurements of the physical characteristic using a model that relates material displacements over time to quantities of the physical characteristic, the subject matter described herein can be used to qualitatively assess relative amounts or qualities of the physical characteristic from displacement measurements obtained from different samples or from the same sample at different times.

Figure 16:
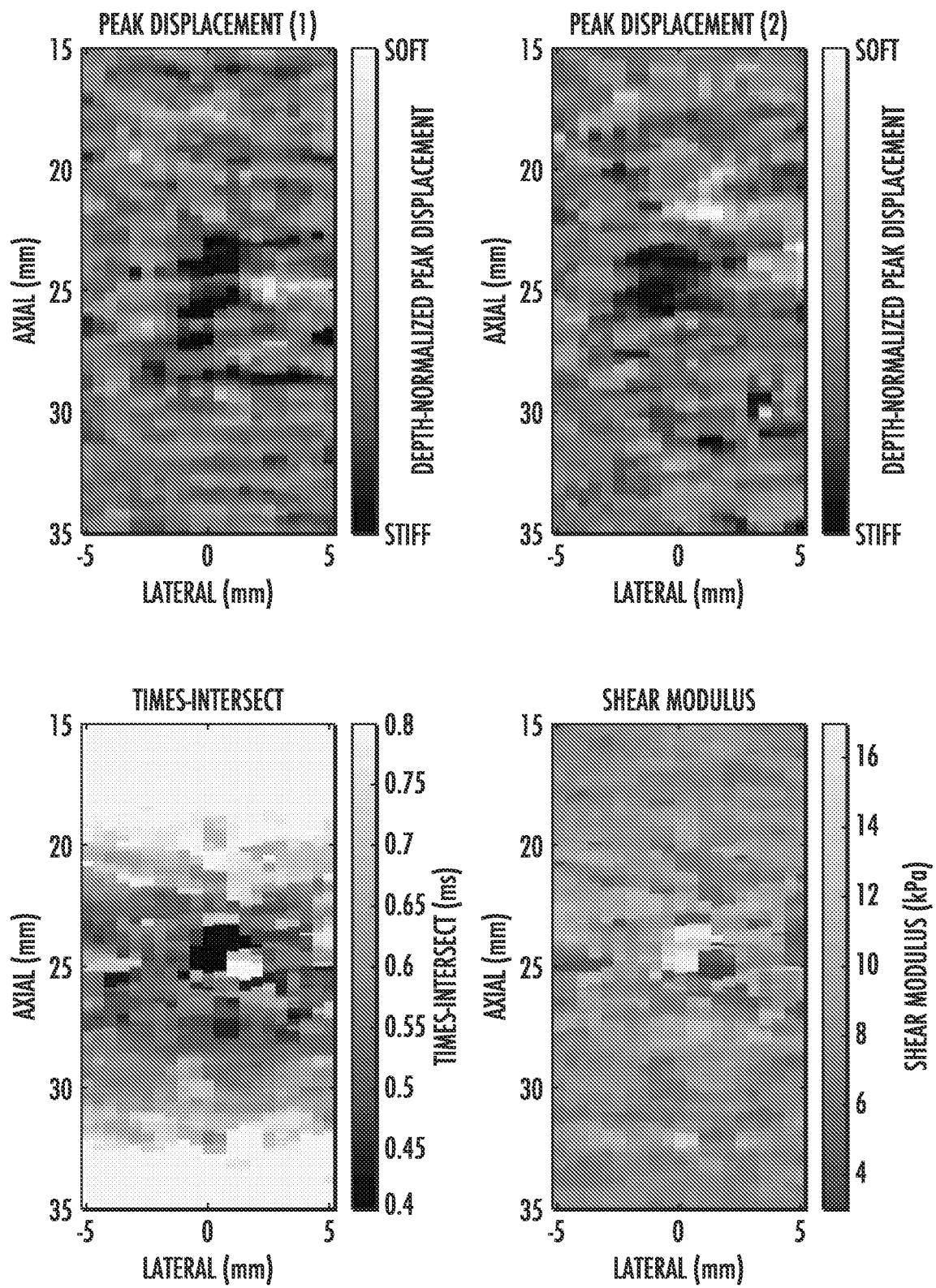
FIG. 16 illustrates depth-normalized peak displacement measured using a (top left) narrower and (top right) wider tracking beam, (bottom left) times-intersect between those two profiles for a given location, and (bottom right) estimated shear modulus of 8 kPa and a square inclusion in the middle with a modulus of 12 kPa for a single combination of scatterer realizations.

FIG. 16 depicts the depth-normalized peak displacement measured using a (top left) narrower and (top right) wider tracking beam, (bottom left) times-intersect between those two profiles for a given location, and (bottom right) estimated shear modulus for a simulated material with a background shear modulus of 8 kPa and a square inclusion in the middle with a modulus of 12 kPa for a single combination of scatterer realizations. The lower-left panel reveals a darker-colored region in the middle, signifying a lower time-intersect, which spatially corresponds to the stiffer inclusion depicted in the lower-right panel.

Figure 17:
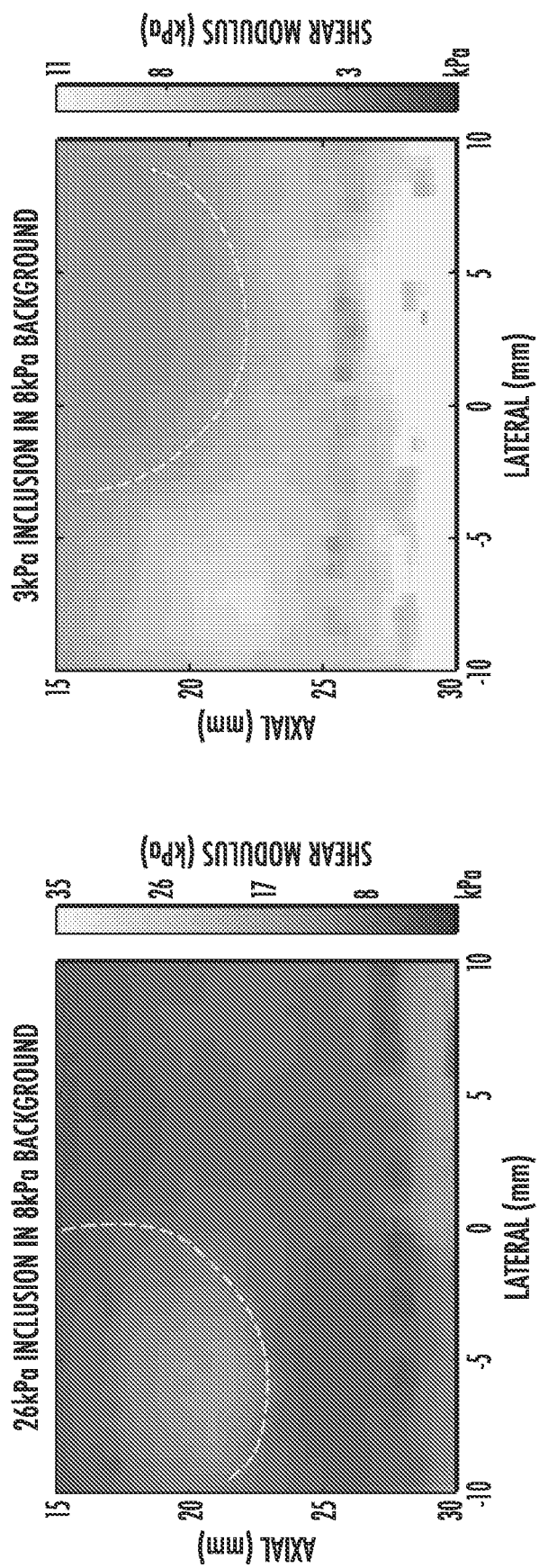
FIG. 17 illustrates estimated shear moduli estimated through a support vector machine in a commercially manufactured tissue-mimicking phantom with a background shear modulus of 8 kPa and a spherical inclusion with a shear modulus of 3 kPa.

FIG. 17 depicts estimated shear moduli estimated through a support vector machine in a commercially manufactured tissue-mimicking phantom with a background shear modulus of 8 kPa and a spherical inclusion with a shear modulus of 3 kPa. The shear modulus was estimated using displacement profiles measured from a clinical scanner. An approximate position of the spherical inclusion is outlined in both panels in yellow dotted lines. The support vector machine was trained on displacement profiles of simulated materials with homogeneous elasticity measured using the same transducer.

The following sections describe additional development of the embodiments described herein, including, but not limited to details about how an empirical relationship between times intersect and elastic modulus was derived, comparisons of Doplo to SWEI imaging, an experimental reduction to practice of Doplo imaging, and experimental results that suggest that Doplo is not force magnitude dependent.

I—Introduction

The elasticity of tissue has been utilized as a pathological biomarker since antiquity through palpation, as well as through several modern, noninvasive imaging methods. While ultrasonic elastography is being applied for a limited range of body regions and disease states, its widespread adoption has been limited, in part, by the fidelity of information in output images. Although resolution and quantifiable measurements are both desirable for noninvasive alternatives to biopsies, traditional clinically relevant techniques in transient elastography require one of them to be sacrificed.

Several established methods such as strain imaging and acoustic radiation force impulse (ARFI) imaging offer pointwise measurements of tissue deformation, but in a purely qualitative manner [1], [2]. In these methods, an unknown magnitude of compressive force is externally applied to some region of tissue, and the resulting displacements in tissue are tracked over time. Ultrasound has been applied to enable pointwise measurements of tissue mechanical properties using speckle-tracking, spectral, and model-fitting methods [3]. However, since the magnitude of the applied external force is unknown, the force applied onto each pixel on an imaging plane is also unknown. This implies that a quantitative stress-strain relationship cannot be assessed, limiting analyses to qualitative comparisons of elastic responses. In other words, in ARFI or strain images, relative stiffness may be compared within regions of the same image, but comparisons between images or global standard values are not feasible on a pixel-by-pixel basis. Furthermore, strain imaging based on compression applied onto a patient using an imaging transducer is operator-dependent and difficult to reproduce. Thus, even though it is capable of making pixel-by-pixel representations of tissue stiffness, the scope of available information and practical considerations fundamentally limit the utility of qualitative elastography techniques.

Quantitative methods of ultrasonic elastography, however, exist and are capable of addressing such shortcomings by design. These methods often involve the tracking of shear waves induced by an externally applied force; the force may be applied through an external vibrator [4] or, more commonly, an acoustic radiation force (ARF) with a duration on the order of 100 µs [2]. The speed of these shear waves correlate to the shear elastic modulus within a homogeneous volume of tissue, and the resulting elasticity predictions can be used as quantitative biomarkers. Existing techniques such as shear wave elasticity imaging (SWEI) and shear wave dispersion ultrasonic vibrometry (SDUV) rely on measuring induced displacements at multiple lateral positions relative to the center of an ARF excitation [2], [5], [6]. Shear waves are tracked across this range of different distances between ARF pushes and displacement-tracking beams, or a "push-track separation", and an average shear wave speed is estimated for this lateral tracking kernel. It must be emphasized that this shear wave velocity measurement is spatially averaged across multiple positions along the direction of a propagating shear wave. While the distinction of an "average" shear wave speed is superfluous in homogeneous tissue such as the liver or the pancreas, biological tissue can be very mechanically heterogeneous on the millimeter scale. Employing shear wave tracking kernels sized at a similar scale to such mechanical features may obscure, or "average out", elasticity differences that could be clinically relevant.

Diseased animal tissue, including those of humans, exhibit structural abnormalities such as inflammation, fibrosis, necrosis, and deposits of unexpected substances like proteins or calcium. To characterize such tissues, biopsies are often performed by extracting a small sample of potentially diseased tissue using specialized needles or through surgery. Trained specialists then perform histopathological analyses ex vivo on the tissue samples at a microscopic scale with the aid of a diverse library of staining solutions. The resulting analyses consider multiple collections of cells at micrometer levels, combines those observations in a tissue-wide context, and applies that information into an emergent understanding of a disease state. The converse of this statement, then, describes the principles required for an elastography method to truly act as a noninvasive analogue to histology: to understand the progression of disease on a macroscopic scale, it is useful to understand the biomechanics of tissue at a sub-millimeter scale. Therefore, we suspect the need for noninvasive methods of "virtual biopsy" which are based on commercially available and commonplace medical devices, conduct quantitative measurements, produce repeatable results, and are immune to the impacts of spatial averaging.

While we believe ultrasound elastography possesses a plurality of the ideal characteristics for noninvasive biopsy-like analyses, existing techniques must sacrifice a selection of these desirable features. We herein propose Double-Profile Intersection (DoPlo) elastography as an alternative technique where such trade-offs are unnecessary. In DoPlo, as in ARFI, an ARF excitation is applied onto soft tissue and resulting displacements are tracked at a single position in space through an ensemble of tracking ultrasonic pulses. However, the velocity of shear waves are still measured using displacement measurements like in SWEI and other quantitative elastography methods. Rather than detecting the arrival of shear wave fronts at multiple positions in space, DoPlo uses the displacement profiles measured at a single position following an ARF push to infer modulus. In this work, we demonstrate that DoPlo can consistently and noninvasively estimate the shear elastic modulus of soft solids in a pointwise manner using a commercially available imaging system. Section II outlines the motivation and overall workflow of DoPlo elastography, as introduced in [7], and argues for an intuitive interpretation of DoPlo as a hybrid between ARFI and SWEI. Section III describes the specific methods used to demonstrate the feasibility of DoPlo using a commercially available scanner and transducer in silico as well as in a calibrated phantom. The results of these procedures are presented in Section IV and discussed in Section V.

II—Double-Profile Intersection Elastography

A. ARFI Displacement Underestimation

Tissue can be displaced by ARF pushes up to several millimeters away from the region of excitation (RoE) due to the propagation of induced shear waves. These displacements are detected by periodically transmitting short ultrasonic pulses and measuring phase changes in reflections from acoustic scatterers. However, ARF excitations are volumetric body forces created through an aperture of a finite size rather than perfectly focused point loads. Thus, even if a volume of mechanically homogeneous tissue is excited with a focused ARF push, the scatterers in the region of that volume will shear at different times proportionally to the magnitude of the force, which spatially varies, and the underlying material property [3], [8]. Since displacement-tracking ultrasound beams also use apertures with finite dimensions, every backscatter signal is the sum of signals from many scatterers, each shearing under a beam's point-spread function (PSF). Demonstrated experimentally in [9], this phenomenon manifests as underestimations in ARFI displacement measurements when conventional displacement tracking methods are used.

A displacement profile for some region of ARF-interrogated tissue is constructed by periodically emitting pulse-echo sequences, then measuring phase shifts that maximize the correlation of each backscatter signal to that of some reference timepoint. This measurement scheme was modeled by Walker and Trahey [10] as an unbiased estimator of a scatterer's true displacement for pushing and tracking beams modeled as separate two-dimensional Gaussian surfaces normal to the direction of sound propagation. The estimated mean of this estimator, as initially described by McAleavey et al. [3] and amended by Dhanaliwala et al. [11] to consider mechanical coupling effects, is:

$$\mu_z = \frac{2L_x L_y z(t)}{\sqrt{(1 + 2L_x^2)(1 + 2L_y^2)}} \quad (1)$$

Here, $z(t)$ is the maximum scatterer displacement within the PSF at some time t following a brief ARF excitation. L is the ratio of pushing and tracking beam widths in the x (lateral) and y (elevational) directions, respectively. In other words, for a push beam with a lateral width of $P_x$ and a tracking beam with elevational width of $T_y$, $$L_x = \frac{P_x}{T_x}, L_y = \frac{P_y}{T_y} \quad (2)$$

In linear transducer arrays where an imaging system cannot electronically modify the elevational beam width of either beams (i.e. $L_y$ is fixed), Eq. (1) suggests that $z(t)$ will be underestimated to different degrees based on different values of $L_x$. This is true as long as the true $z(t)$ remains unchanged between the two beams. Even if that is not the case, a useful relationship can still arise when $\mu_z$ is equal between two measurements taken using different values of $L_x$. Denoting the different lateral beam width ratios as $L_{x1}$ and $L_{x2}$ with corresponding maximum scatterer displacements $z_1(t)$ and $z_2(t)$, the two realizations of Eq. (1) can be combined so that $$\frac{2L_{x1}L_y z_1(t)}{\sqrt{(1 + 2L_{x1}^2)(1 + 2L_y^2)}} = \frac{2L_{x2}L_y z_1(t)}{\sqrt{(1 + 2L_{x2}^2)(1 + 2L_y^2)}}$$

and, through the removal of common terms, $$\frac{L_{x1} z_1(t)}{\sqrt{1 + 2L_{x1}^2}} = \frac{L_{x2} z_2(t)}{\sqrt{1 + 2L_{x2}^2}} \quad (3)$$

If the medium where the scatterers under the two beams' PSFs are mechanically homogeneous, then $z_1$ and $z_2$ can be described by the same equation of motion. Therefore, when displacement profiles with varying $L_x$ values result in the equal displacement estimates, there is an implicit relationship between the estimated displacement and the constitutive equation governing the motion of a scatterer interrogated by an ARF excitation.

B. DoPlo Empirical Model

The motion of this scatterer, presumed to undergo a purely elastic recovery, is governed by the medium's shear modulus $\mu$ and density $\rho$. The shear wave propagating through that material has a shear wave velocity, $v_s$, which may be sampled by measuring the time of flight $\Delta t$ needed to propagate some distance $\Delta x$. In other words, $$v_s = \sqrt{\frac{\mu}{\rho}} \approx \frac{\Delta x}{\Delta t}$$

Figure 18:
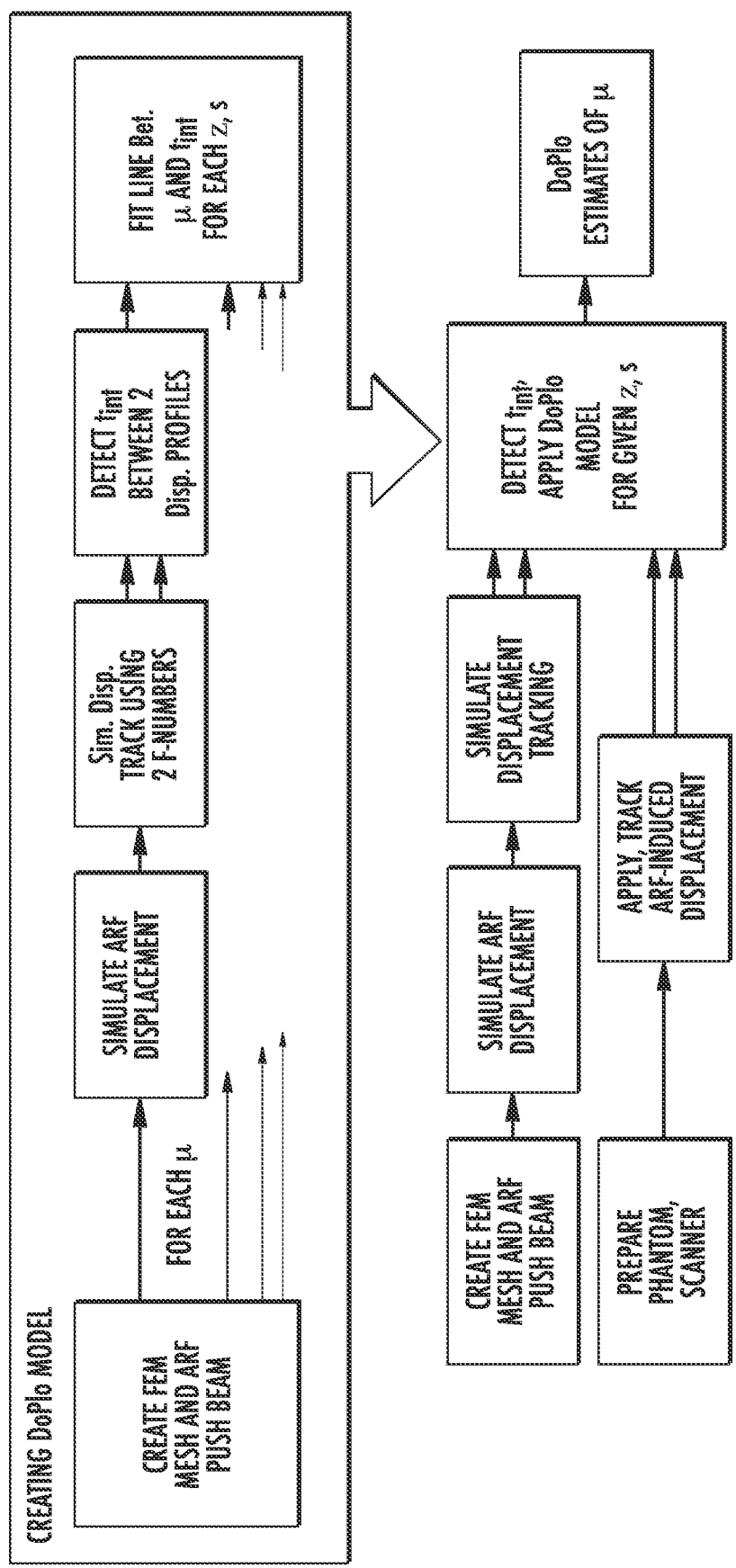
FIG. 18 is an infographic illustrating the major steps of creating an empirical model for DoPlo elastography to estimate the shear modulus of tissue, $\mu$, based on the time-intersect, $t_{int}$, for displacement profiles measuring the same ARF displacement response at axial depth z and push-track separation s.

As mentioned in the introduction, conventional SWEI methods sample the propagation of shear waves across some tracking kernel. However, in introducing DoPlo, we hypothesize that the shear wave velocity under the PSF of a tracking beam can be found by using two different focal configurations while tracking ARF-induced displacements. A conceptual overview of the proposed postprocessing method is depicted in FIG. 18.

The propagation speed of an ARF-induced shear wave, therefore also the rate at which scatterers recover from the induced displacement, is modulated by its stiffness. Since this displacement resolves faster in stiffer materials, we posit that that the rate of change in displacement underestimation encodes information about the stiffness of tissue under a tracking PSF. We suggest that the different degrees of displacement underestimation from two different displacement-tracking F-numbers can be used to infer the stiffness of tissue that is responding to an ARF excitation over time. Information that is common between the two displacement profiles, such as the time where they intersect, may be extracted and converted into an elasticity measurement. As the forces experienced by each scatterer during the ARF response is unknown, we propose an empirically derived model may be employed to convert this time-intersect (plural: times-intersect) into a shear modulus prediction. Through this approach, DoPlo exploits the effect of F-number-dependent changes in scatterer shearing that typically poses the limitation of displacement underestimation in quantitative transient elastography techniques.

DoPlo takes advantage of differences in the shearing of scatterers within different PSFs. While this stands in contrast to SWEI, which tracks the phase velocity of a shear wave traveling across space, both methods ultimately assess mechanical responses to a propagating shear wave. Therefore, the feature that allows for a shear modulus to be extracted from DoPlo should also exhibit a relationship similar to Equation (4), the process used to infer a SWEI shear modulus estimate $\mu$ based on a shear wave speed $v_s$ traveling across a medium with density $\rho$.

$$\mu = v_s^2 \rho \propto \frac{1}{\Delta t^2} \tag{4}$$

Asserting that the density of human tissue is roughly homogeneous and the time-intersect is inversely proportional to the velocity of a shear wave traversing through a tracking position, (4) can be reformulated into a linear function. This results in an inverse-square relationship between the time-intersect of two displacement profiles from an identical ARF and tissue position and the shear elastic modulus of tissue:

$$\mu(z, s, t_{int}) = A(z, s)\frac{1}{t_{int}^2} + B(z, s) \tag{5}$$

Here, the polynomial coefficients for this model were empirically derived in simulation as a function of axial depth z and push-track separation s, given some combination of tracking F-numbers and a fixed focal depth for ARF push and track beams. This inverse-square relationship was used to empirically develop a model that can quantify tissue elasticity like SWEI but in an ARFI-like manner where displacement tracking across multiple spatial positions is unnecessary.

III—Methods

Figure 19:
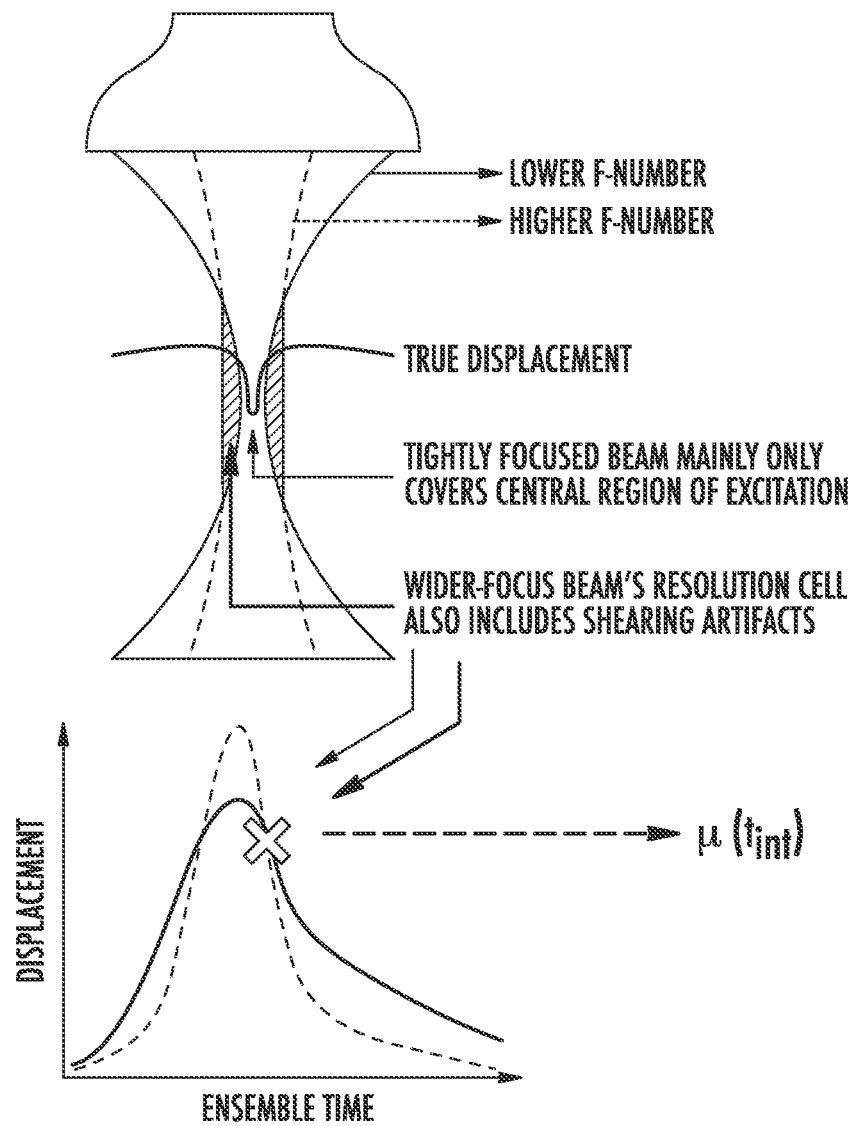
FIG. 19 is an infographic illustrating that the two tracking focal configurations capture different degrees of ARF-induced scatterer shearing, as well as the exploitation thereof for estimating a shear elastic modulus using an empirically-derived model.

The primary focus of this report is to establish the DoPlo imaging workflow, demonstrate its use in idealized conditions, and characterize its performance. In the first subsection, the parameters for ultrasonic simulations and the process of detecting times-intersect are defined. The next subsection concerns the creation of the empirical model that generates shear modulus estimates for each ARF displacement measurement, followed by an evaluation of DoPlo measurement performances in various additional in silico environments. Finally, an in vitro implementation of DoPlo is demonstrated using a clinical scanner system. The contexts of these procedures are illustrated in FIG. 19.

A. Ultrasonic Imaging Simulation

An ARFI push excitation with a center frequency of 4.21 MHz was simulated using the specifications of the Acuson VF7-3 (Siemens Healthineers, Issaquah, Wash., USA), a linear array with a physical lens elevationally focused at 36 mm, electronically focused at a depth of 25.0 mm. To do so, following the procedures introduced by Palmeri et al. [12], [13] and using the linear ultrasound simulator Field-II [14], an ARF push beam with an F-number of 1.5 was simulated by creating a spatial map of the beam intensity using a 50-cycle transmit pulse. This volumetric intensity field was normalized around the focal depth, scaled at an $I_{SPPA}$ of 5000 W/m², and converted into body forces in the axial direction (i.e. z, the direction of acoustic wave propagation) using Equation (6):

$$F_z = \frac{2\alpha I}{c} \tag{6}$$

In this case, an acoustic medium was set to have a constant sound speed of 1540 m/s and acoustic attenuation coefficient $\alpha$ is in nepers based on 0.5 dB/cm/MHz measured in reference to the transmit frequency. A hexahedral grid of nodes was created with nodes uniformly spaced 0.250 mm apart 42.0 mm axially, 20.0 mm laterally, and 12.0 mm elevationally; this created a mesh with element volumes of about 0.0156 mm³. Eq. (6) was evaluated at each nodal position, and point loads were defined on this mesh by dividing the calculated body force by the element volume for the mesh. This force was applied onto the mesh for 80 μs, corresponding to 300 cycles given the transmit frequency, and the resulting displacement response was solved using the multiphysics FEA simulator LS-DYNA (ANSYS, Canonsburg, Pa., USA) at timesteps of 1 μs. The resulting field of displacements were saved at every 0.1 ms until 3.5 ms after the ARF excitation. Elements were defined as linearly elastic materials, the values and distributions varying depending on the experiment described in the following subsections. To prevent boundary reflections at the edges of the simulation, the outer six elements of the mesh in all directions were replaced with the |*PML_ELASTIC| material of identical elasticity. Except for operations involving LS-DYNA, all post-processing steps, as well as interfaces with Field-II, were performed through MATLAB (MathWorks Inc., Natick, Mass., USA).

A randomly-generated list of numbers were used to define the position and amplitude of scatterers so that, defining a resolution cell as the volume for the full-width-half-max region of the PSF of an acoustic beam, the average scatterer density in a tracking PSF equals 25 scatterers per resolution cell. The positions of these scatterers were mapped onto the displacement field generated by the LS-DYNA simulation by linear interpolation, and pulse-echo sequences were applied in Field-II with the aforementioned transducer [14], [15]. The tracking pulse-echo responses were simulated for F/#1.5, 3.0, and 4.5, a 6.15 MHz transmit focused at 25.0 mm, and dynamic receive focusing at fundamental frequency. Pulse-echo sequences were repetitively emitted at a 10 kHz PRF, and the resulting array of RF data was used to track tissue displacements. For most cases, normalized cross-correlation (NCC) was performed using a 2-wavelength (500 μm) tracking kernel and a 0.3-wavelength (80 μm) search window [16]. For each ARFI push, displacements were tracked in an axial range spanning from the transducer surface to 40.00 mm in depth, as well at lateral positions spanning from the center of excitation (i.e. identical to the lateral position of the ARF focus) to 6.00 mm on the right side in 0.50 mm increments.

For a given scatterer realization, axial depth, and push-track separation, displacement profiles made using two tracking F-numbers (i.e. one track F-number combination, or tFc) were selected. Each profile was upsampled tenfold using piecewise-cubic interpolation over time [17]. This interpolation function was intentionally chosen over a spline-based method to prevent stiffer materials from being represented by artificially high-amplitude displacement profiles. Since the spline interpolation function in MATLAB can result in values that deviate from reference values to ensure smooth solutions, the profiles of stiffer materials, when acquired through a lower PRF, can resemble those of softer materials due to diminished differences in peak displacements. The piecewise-polynomial choice, therefore, was chosen as a compromise between increased sensitivity for detecting times-intersect and minimizing the potential distortion of mechanically-relevant information. Following interpolation, the displacement profiles were transformed onto a homogeneous coordinate system in the interest of computational efficiency [18].

B. Developing the Empirical Model

To generate a library of times-intersect for materials of different shear moduli, ten LS-DYNA meshes were generated. Elements in each mesh were homogeneously assigned one of 10 shear modulus values ranging from 1 kPa in 4 kPa increments up to 37 kPa. Following the simulated ARFI excitation previously described, displacement responses were interpolated onto 20 different random distributions of scatterers for each elasticity. The resulting displacements were converted into lists of scatterers translated over time, and the scatterers' displacements were tracked and intersected.

For all phantoms, times-intersect were calculated for displacements tracked between depths of 15.00 mm and 35.00 mm (i.e. 10 mm above and below the focal depth). Displacements were tracked at the RoE as well as push-track separation of up to 6.0 mm. Times-intersect at each axial depth, push-track separation, and modulus were inverse-squared to reflect the shear modulus' inverse-square dependency to a time derivative in (4). For each spatial position, a linear regression was performed between the times-intersect and shear moduli using the maximum likelihood estimation sample and consensus (MLESAC) method [19]. Without any a priori knowledge of coefficient magnitudes or appropriate weights on times-intersect, MLESAC was performed with a 10 ms$^{-2}$ hard limit, 95% confidence interval acceptance boundary, and sums of squared differences for distance metrics; line-fitting for each axial depth, push-track separation, and tFc was terminated after 10,000 iterations. This results in a map of polynomial coefficients distributed across different axial positions and push-track separations. These coefficients can be used to convert a time-intersect into a shear modulus estimate μ through (5).

(5) holds true for a given tFc and ARF excitations and tracking pulses at a given focal depth. For this study, 25.00 mm was used to balance between realistic applications for superficial abdominal imaging and to ensure that displacement magnitudes were above the Cramer-Rao lower bound. Furthermore, for each tFc, the slope and intercept of this linear fit for all depths and push-track separations were used to fit a two-dimensional surface parameterized by the axial depth and push-track separation. This formulation allows for the conversion of a time-intersect at an arbitrary point in space with respect to an ARFI excitation given that the ARF push and track sequences are also performed.

C. In Silico Performance Evaluation

To evaluate the shear modulus prediction model created in the previous subsection, additional LS-DYNA-based simulations of ARF displacements were performed in three additional in silico environments. All experiments described herein only concern tFc of 1.5 and 3.0.

First, the performance of the model was validated using 13 additional LS-DYNA simulations of homogeneously elastic materials. 10 scatterer distributions were generated for each material, and displacements were tracked using the previously described simulation, imaging, and tracking parameters. Similar to the reference simulations, times-intersect were calculated for all available push-track separations and depths within 10 mm of the focal depth. However, the polynomial model to estimate shear moduli from times-intersect was evaluated at the detected times-intersect, imparting estimates of shear moduli for each pair of distinct displacement profiles.

Additionally, measurements were generated for two different heterogeneous phantoms. The heterogeneous FEM meshes both consisted of a thin inclusion with a 2.50 mm-wide square cross section centered 25.0 mm under the center of the transducer surface. The first heterogeneous phantom comprised of a background with a 10 kPa shear modulus and an inclusion with a 5 kPa shear modulus; the second phantom had an inverted contrast with a 12 kPa inclusion surrounded by an 8 kPa background. Separate ARF excitations were emitted up to 5.0 mm to the left and right of the center of each inclusion in 0.5 mm increments. Displacement responses for each push was tracked using NCC as well as a multidimensional blind-source separation (BSS)-based tracking algorithm [20]. The 3D-BSS displacement tracker also used an 80 μm axial kernel, but also sampled displacements from one adjacent lateral line on each side and five adjacent tracking pulses.

For comparison, MTL-SWEI was also performed using the NCC-based displacements. Using a 3.0 mm lateral kernel and a least-squares-based linear fit for determining the time of flight of a shear wave front, shear wave velocities were sampled and squared to create a comparative map of estimated shear moduli. Once maps of estimated moduli were generated for all positions within all imaging fields, a map of average modulus estimates for the 10 scatterer realizations generated in each scenario were recorded for all postprocessing methods. Following the application of a median filter with a 0.5 mm kernel, the positions of the inclusion and background were determined using 500 iterations of the Chan-Vese algorithm seeded from the expected center of the inclusion [21].

The estimated shear modulus inside and outside of the inclusion was then recorded for each image. To measure DoPlo's performance in modulus differentiation, the contrast-to-noise ratio (CNR) was measured as $$CNR = \frac{|\sigma_{in} - \sigma_{out}|}{\sqrt{\sigma_{in}^2 + \sigma_{out}^2}} \quad (7)$$

where $\sigma_{in}$ is the standard deviation of the estimated shear moduli in regions segmented as the "inside" of the inclusion. Likewise, $\sigma_{out}$ denotes the same but outside of the inclusion. As a rule of thumb, a higher CNR implies lower variance in modulus estimates.

The contrast transfer efficiency [22] (CTE) was also calculated in DoPlo modulus images, defined as $$CTE = \frac{\widetilde{\mu_{in}}/\widetilde{\mu_{out}}}{\mu_{in}/\mu_{out}} \quad (8)$$

$\widetilde{\mu_{in}}$ denotes the average estimated (denoted with the tilde) modulus inside the inclusion whereas $\mu_{out}$, which does not include glyphs above the $\mu$, denotes the true modulus outside of the inclusion. A CTE of 1.0 means shear moduli are resolved with the intended resolution.

Finally, the axial and lateral sizes of the largest square that could be circumscribed within the segmented inclusion. Since the simulated inclusion is defined to have a square cross-section, this metric was used to assess the spatial accuracy of DoPlo measurements.

D. Phantom Evaluation

Finally, shear moduli for a commercially marketed, calibrated elasticity imaging phantom were measured using DoPlo in a clinical scanner. The CIRS Type 049A spherical phantom (CIRS, Norfolk, Va., USA), a phantom with a spherical inclusion centered at a depth of 15 mm with a Young's modulus of 3 kPa embedded inside a background material with a Young's modulus of 25 kPa, was imaged using a VF7-3 transducer attached to a Siemens Acuson Antares (Siemens Healthineers, Issaquah, Wash., USA) commercial ultrasound scanner on top of a motion isolation table. ARF pushes focused at a depth of 25.00 mm with an F-number of 1.5 were emitted at 40 different lateral positions; for each set of 40 pushes, and the resulting displacements were tracked on-axis to the push beam at a PRF of 10 kHz and focal depth of 25.00 mm until 3.5 ms after the ARF excitation. This ensemble was emitted and recorded twice, with the first iteration using a tracking F-number of 1.5 and the second set of 40 pushes' displacements being tracked with an F-number of 3.0. This ARF push-track sequence was repeated five times in the phantom where, for each iteration, the magnitude of ARF excitations were modified by scaling the maximum voltage across the VF7-3 transducer elements to some percentage of the maximum voltage allowed by the Antares scanner. Push power magnitudes of 10%, 20%, 40%, 60%, and 80% of the maximum voltage were used. All beamformed RF lines collected from the scanners for all push powers were converted into displacement profiles via NCC similarly to the LS-DYNA-based simulations, then converted into shear moduli.

IV—Results

Figure 20A:
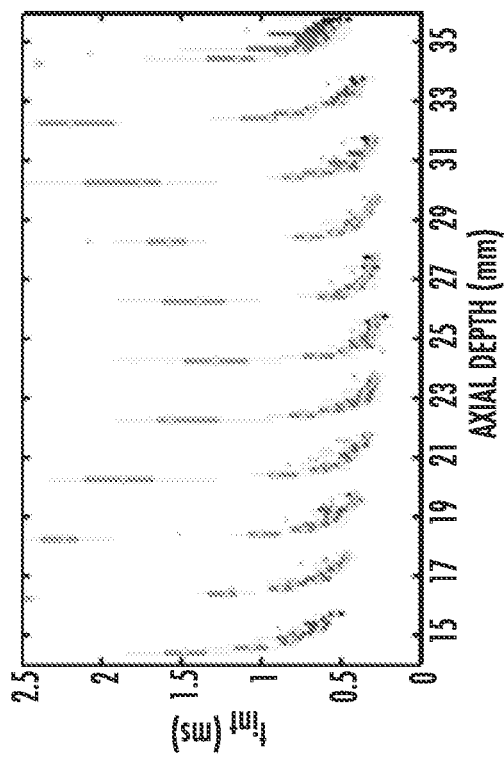
FIGS. 20A-20D illustrate times-intersect at the focal depth for various push-track beam separations.
Figure 20B:
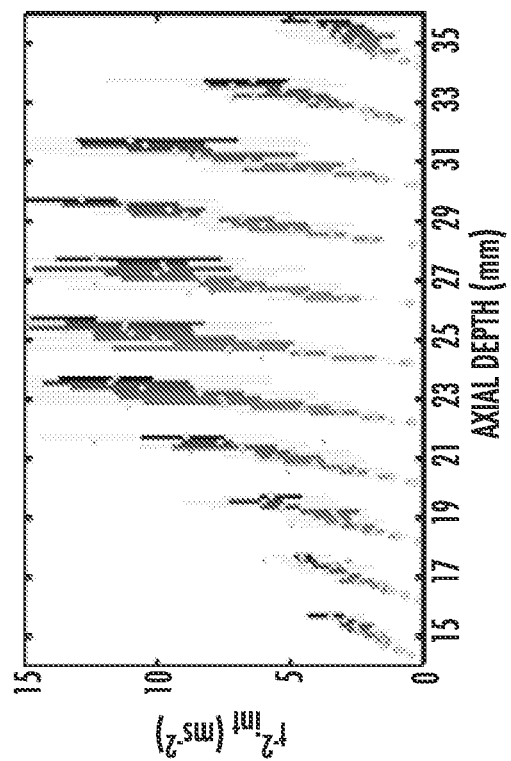

FIGS. 20A-20D show a distribution of times-intersect measured at different positions in space and different shear elastic moduli for an ARF excitation and tracking pulse focused at 25.00 mm. For FIGS. 20A and 20D, times-intersect of different shear moduli are color-coded, starting with 1 kPa in magenta (gray in print versions), and progressively getting darker in 4 kPa increments up to 37 kPa. FIG. 20A depicts times-intersect for various shear moduli across different push-track separations at the focal depth. Likewise, FIG. 20B shows times-intersect on-axis to the RoE at various axial depths. In both cases, for a given spatial position, a nonlinear correlation between times-intersect and shear moduli can be observed. It should be noted that time-intersect values increase for all modulus values as the position of displacement tracking moves away from the RoE. It should be noted that the linear increases in times-intersect over distance are more pronounced for softer materials, implying that times-intersect for displacements tracked away from the RoE is impacted by the time-of-flight for a shear wave front to be registered by the tracking PSF. However, it should be noticed that time-intersect differences across moduli can be observed across all push-track separations and axial depths with variances for all cases aside for the 1 kPa material.

Figure 20C:
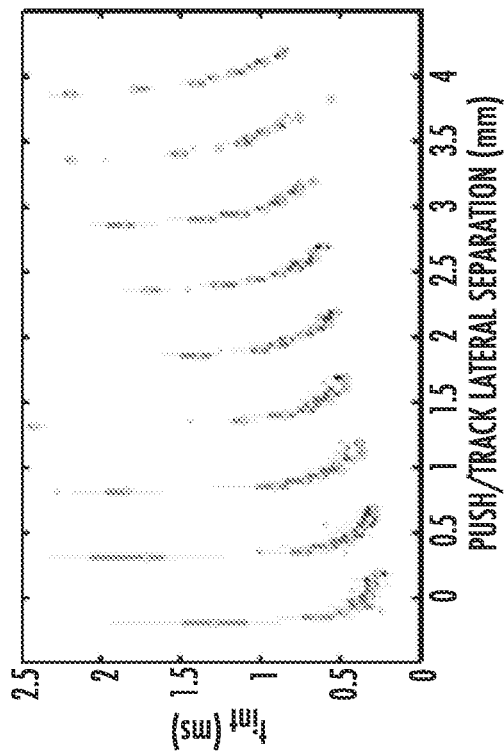
Figure 20D:
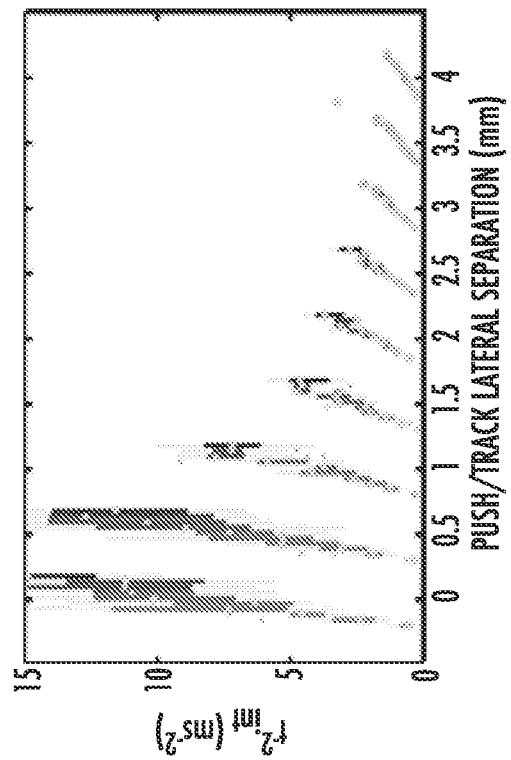

FIGS. 20C and 20D depict the inverse-squared values of FIGS. 20A and 20B. Similarly to the previous panels, time-intersect distributions are color-coded for each position based on the stiffness of the material being interrogated by the ARF excitation. It should be noted that the inverse-squaring operation exaggerates small differences in times-intersect, especially at smaller magnitudes. This has the impact of skewing inverse-squared time-intersect values to higher magnitudes and increasing the variance of times-intersect in stiffer materials. It should be noted, however, that linear conversion factor between times-intersect and shear elastic modulus was identified using a MLESAC-based polynomial fit rather than a least-squares regressor. As a member of the random sample consensus (RANSAC) family of iterative estimators, MLESAC evaluates goodness-of-fit through distance metrics so that distant points are automatically rejected as outliers. Thus, the robust linear regressor can be interpreted to also standardize the distributions of times-intersect across different moduli, nullifying the heteroskedasticity that is especially prominent with on-axis times-intersect in FIG. 20C.

FIGS. 21A and 21B show shear modulus estimates for homogeneous materials not previously encountered by the model created from FIGS. 20A-20D. FIG. 21A depicts the distribution of estimated moduli for on-axis measurements at the focal depth, while FIG. 21B shows those for displacements tracked 3.0 mm away from the RoE. While the average of estimated modulus values largely overlap with expected values, the standard deviation progressively increases as a function of modulus. This tendency appears to reflect the heteroskedasticity seen in FIGS. 20C and 20D. Modulus estimates for off-axis measurements, however, largely remained within 10% of ground truth, even for materials that were stiffer than those represented in the model-creating process. These estimates appear to be slightly underestimated, which becomes more pronounced in materials with shear moduli above those used for model creation (i.e. stiffer than 37 kPa). As mentioned in the previous paragraph, this may be attributed to how inverse-squaring times-intersect can skew inputs to the empirical model in favor of lower magnitudes.

Figure 22B:
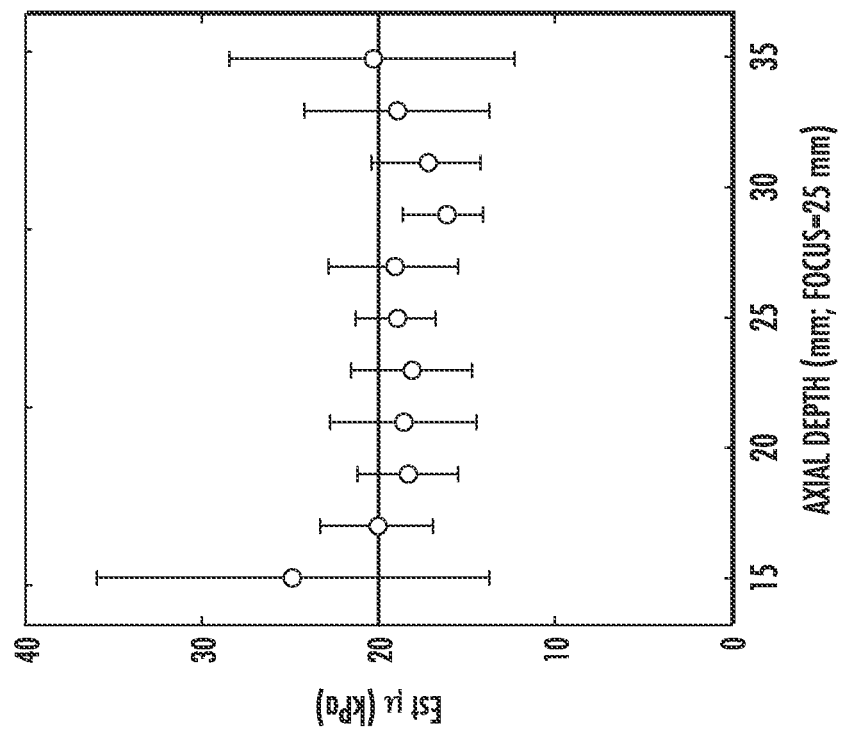
FIGS. 22A and 22B illustrate shear modulus estimates across axial depth and push-track separations.
Figure 22A:
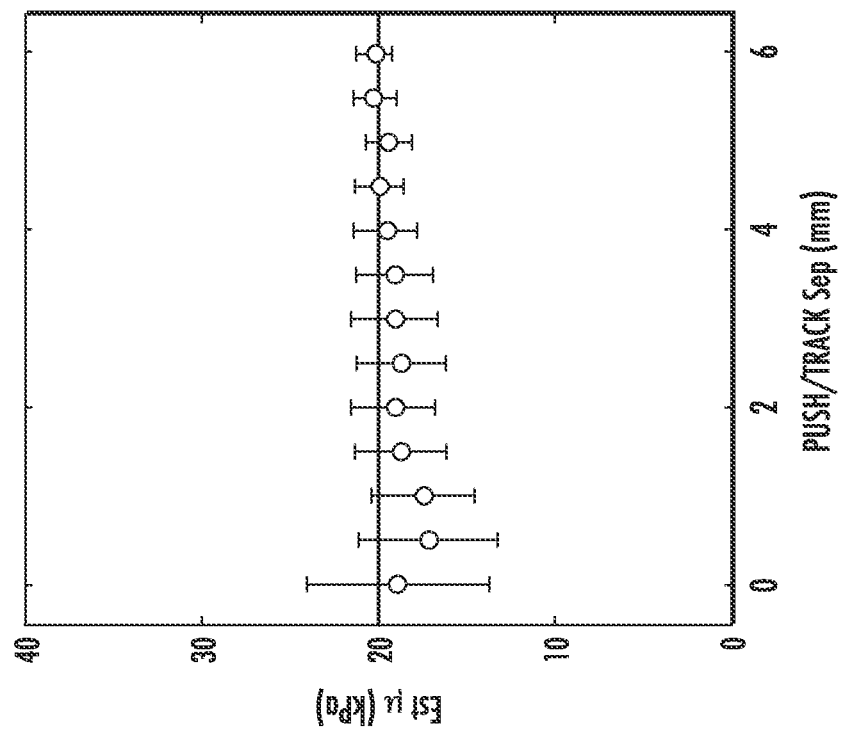

FIGS. 22A and 22B show the distribution of modulus estimates for 10 different measurements of a digital phantom with 20 kPa shear modulus across two different dimensions. FIG. 22A illustrates changes in modulus estimates for different push-track separations for displacements measured at the focal depth. Likewise, FIG. 22B depicts modulus estimates in the same material over different axial depths based on displacements tracked at a push-track separation of 2.0 mm. As in the previous figures, modulus estimates are roughly consistent between true and estimated values. Decreasing standard deviations over an increasing push-track separation can also be observed in FIG. 22A which, as in FIG. 22B, can be attributed to globally increased times-intersect artificially decreasing variance in its inverse-square. FIG. 22B, on the other hand, maintains roughly similar variances for roughly 5 mm from the focal depth.

Figure 23A:
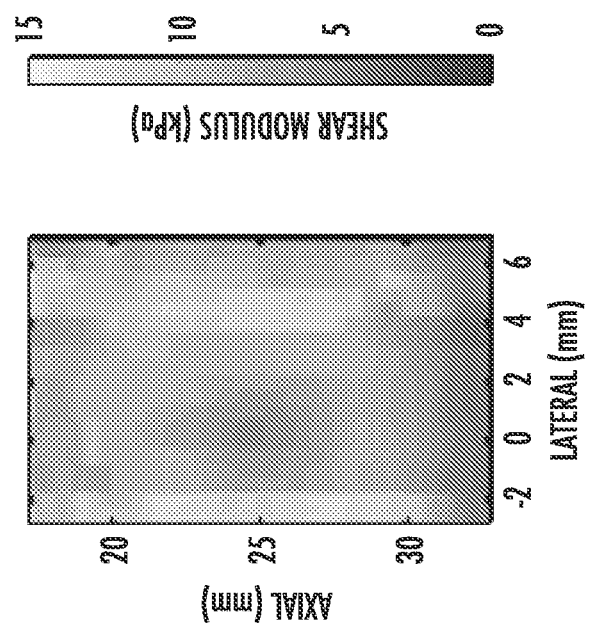
FIGS. 23A-23C illustrate average shear modulus estimates for heterogeneous simulation with small, soft, square-shaped inclusion embedded inside stiffer background.
Figure 23B:
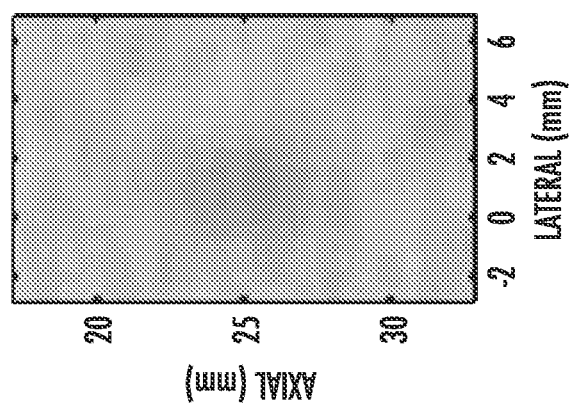
Figure 23C:
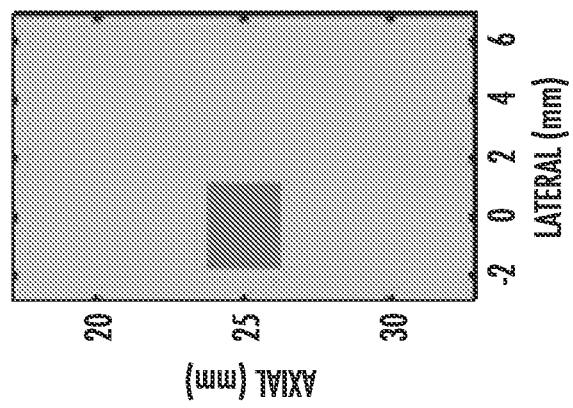

FIGS. 23A-23C compare DoPlo and SWEI images for a heterogeneous digital phantom with a stiffer background elasticity, as well as a very long bar with a 2.50 mm square cross-section inclusion with a softer shear modulus; all panels are depicted using the same scale and colormap displayed on the far right side. FIG. 23A depicts the true shear elastic modulus distribution in the digital phantom. The lateral borders of the inclusion, a square with a side length of 2.50 mm, are located halfway between two A-lines on either side. FIG. 23B depicts the average DoPlo modulus estimate out of 10 scatterer realizations based on displacements tracked 2.0 mm from the RoE. FIG. 23C is also the average modulus estimate, but for MTL-SWEI based on a 2 mm lateral kernel.

Table 1 outlines the performance metrics used to assess the ability to resolve features of different shear elasticities using DoPlo. This table lists the estimated shear moduli, CNR, CTE, and dimensions of a square inclusion with varying elasticity from the background. Materials with two distributions of elasticities were considered in this analysis. The first situation is the same as that which is depicted in FIGS. 23A-23C, where a soft inclusion is embedded within a stiff background. Below those rows, modulus estimates and image quality metrics for an additional scenario are tabulated. Here, a stiffer inclusion is embedded in a soft background. As in FIGS. 23A-23C, performance metrics for delineating inclusions are for taken using the average image out of DoPlo estimates based on displacement pairs from 10 different scatterer distributions. Note that inclusion sizes are equal in all image scenarios, but the contrast between the background and inclusion are inverted between the two scenarios.

TABLE 1

COMPARISON OF DoPlo AND SWEI ELASTICITY ESTIMATES

| Layout | Shear Modulus (kPa) | | CNR | CTE | Incl. Size (mm) | |
|---|---|---|---|---|---|---|
| | Inclusion | Background | | | Axial | Lateral |
| Truth | 5.0 | 10.0 | ∞ | 1.00 | 2.50 | 2.5 |
| MTL-SWEI | 6.7 ± 0.6 | 12.0 ± 1.2 | 3.95 | 1.12 | 3.71 | 3.0 |
| DoPlo[a] | 7.1 ± 0.5 | 10.7 ± 0.5 | 5.09 | 1.33 | 2.60 | 2.5 |
| DoPlo[b] | 7.9 ± 1.5 | 9.4 ± 1.2 | 1.68 | 0.78 | 4.92 | 4.0 |
| Truth | 12.0 | 8.0 | ∞ | 1.00 | 2.50 | 2.5 |
| MTL-SWEI | 9.7 ± 0.8 | 8.5 ± 0.6 | 1.29 | 0.76 | 3.37 | 2.5 |
| DoPlo[a] | 9.6 ± 0.6 | 8.1 ± 0.4 | 2.90 | 0.78 | 1.61 | 2.5 |
| DoPlo[b] | 10.9 ± 1.0 | 9.5 ± 0.8 | 1.13 | 0.77 | 1.93 | 3.0 |
| DoPlo[c] | 12.3 ± 1.5 | 10.2 ± 1.2 | 1.12 | 0.81 | 2.58 | 4.0 |

[a]Displacements measured at push-track separation of 3.0 mm using NCC.
[b]Displacements measured on-axis (i.e. at the RoE) using NCC.
[c]Displacements measured on-axis (i.e. at the RoE) using BSS.

Figure 24A:
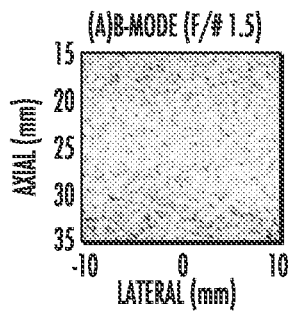
FIGS. 24A-24J illustrate a comparison of DoPlo modulus estimates for calibrated phantom using various ARF push magnitudes.
Figure 24B:
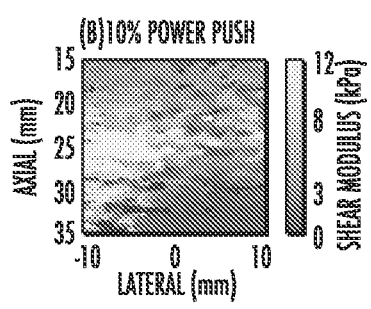
Figure 24C:
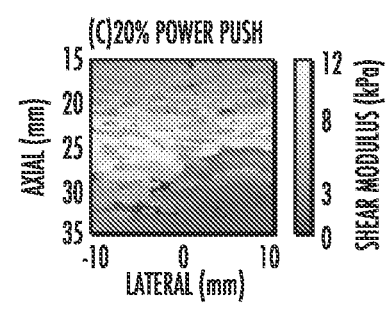
Figure 24D:
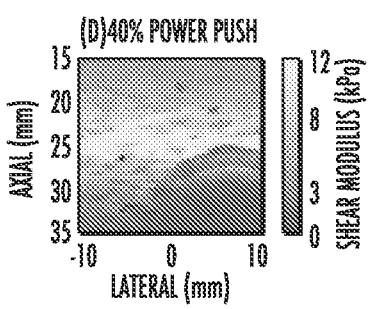
Figure 24E:
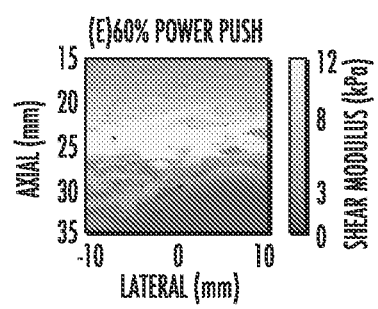
Figure 24F:
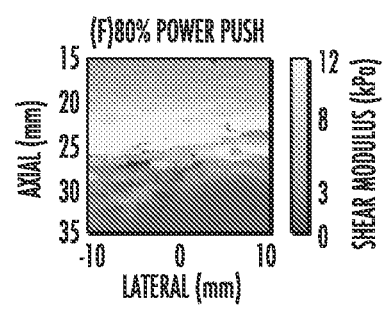
Figure 24G:
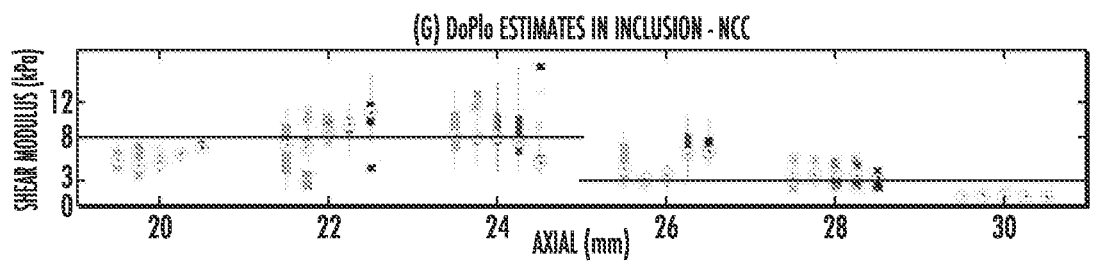
Figure 24H:
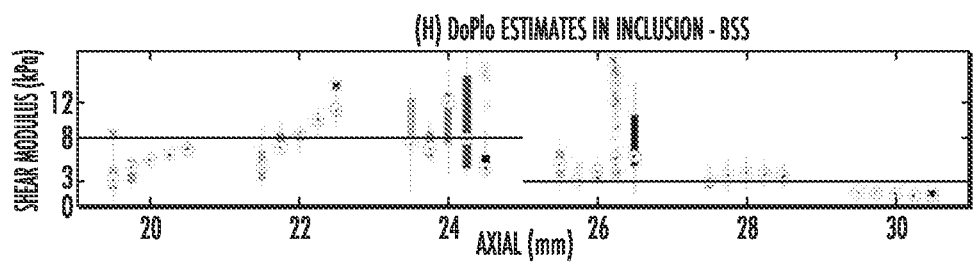
Figure 24I:
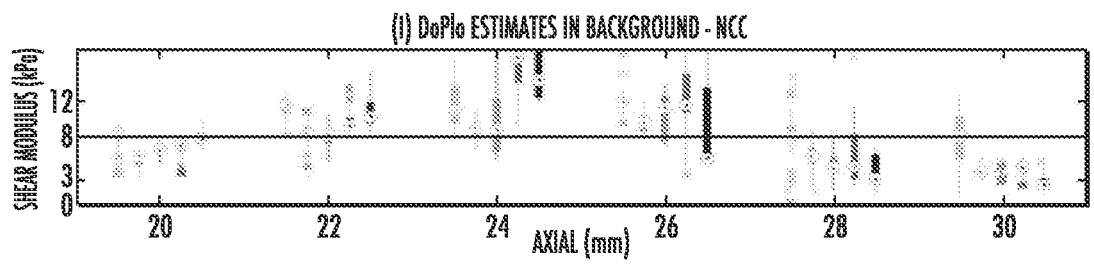
Figure 24J:
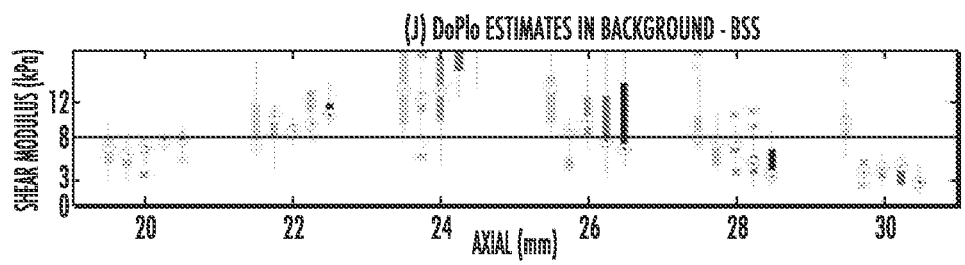

FIGS. 24A-24J illustrate DoPlo estimates for a CIRS phantom imaged following ARF push pulses of varying amplitudes. A B-mode image with an outline for the spherical inclusion is listed in FIG. 24A; FIGS. 24B-24F denote several depiction of DoPlo shear modulus estimates for each ARF excitation magnitude. FIGS. 24G-24J show a box-whisker plot of the average, interquartile range, and 95% confidence interval of estimated shear moduli for various axial depths. Error bars in these four panels are colored from brighter to darker in order of lowest to highest ARF push powers. FIGS. 24G and 24H depict modulus estimates within 0.5 mm of indicated axial depths for a lateral position of 5 mm (i.e. where the inclusion is centered) using NCC and BSS tracking algorithms, respectively. Likewise, FIG. 24I and FIG. 24J illustrate modulus estimates for the same range at a lateral position of −10 mm, a position in FIG. 24A where the inclusion is not present.

V. Discussion

In introducing DoPlo, we demonstrate that scatterer shearing can be exploited to evaluate shear elastic modulus. Shear elastic modulus estimates were generated both in and out of the RoE for homogeneous materials and materials with small inclusions. DoPlo was able to estimate shear moduli with an accuracy comparable to MTL-SWEI, albeit with noisier signals as evident in Table 1. Unlike SWEI-based methods that depend on large-distance shear wave propagation, however, the analysis of DoPlo measurements include those captured on axis with an ARF excitation. With the potential to assess on-axis quantitative metrics of tissue stiffness, DoPlo may allow for mechanical feature detection with improved sampling capabilities compared to existing techniques.

In its current implementation, however, DoPlo requires focused tracking of ARFI displacements using more than one F-number. In commercial scanners approved for human clinical use, many of which are not capable of accessing channel-level RF traces prior to receive beamforming, this requires two sets of independent displacement measurements. If DoPlo is performed using such a device and tissue motion unrelated to ARF-induced displacements occurs, the displacement profiles that should encode two different realizations of the "same" tissue may actually correspond to different positions with respect to the RoE. This may result in profile intersections at unexpected times, if it were to occur at all. However, a more robust solution would involve both displacement profiles originating from a single acquisition. This approach could involve the acquisition of a single set of channel RF data, then beamforming and displacement-tracking the same dataset using multiple F-numbers simultaneously. We intend to demonstrate a proof-of-concept of such a workflow in vitro with both experimental and clinical scanners in the near future.

Underdeveloped speckle, necessitated by practical limitations of the in silico methods used by this study, may also be impacting the precision of DoPlo modulus estimates. Field-II, the simulator used for ultrasonic displacement tracking, operates by convolving scatterers with the PSF of some transducer given some pulse-echo sequence, then repeating the process for an arbitrary number and position of scatterers [14]. Given the Rayleigh model of sub-wavelength scatterers, this requires that a minimum number of scatterers exist within a resolution cell volume for fully-developed speckles to realize in ultrasound backscatter signals [23]-[25]. This value, heuristically treated to be roughly 11 per resolution cell, is typically applied to a single resolution cell. However, DoPlo relies on the existence of some difference between two resolution cells' scatterer motions to identify useful biomechanical information. While the decision to use 25 scatterers per resolution cell for each tracking F-number was motivated to ensure full speckle development, this raises the possibility that an insufficient scatterer density was effectively being tracked through the use of DoPlo.

We surmise that this issue of insufficient scatterer density is also responsible for the large uncertainties in modulus estimates seen in FIG. 21A. Unlike the model creation demonstrated in FIGS. 20A-20D, evaluated models' times-intersect cannot be weighted to the fit function in a robust manner. To test the impact of scatterer density on the reliability of DoPlo modulus estimates, simulations with higher scatterer densities will be required.

Figure 25D:
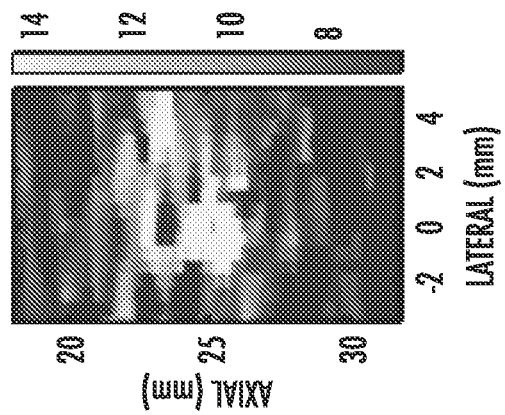
FIGS. 25A-25D illustrate a comparison of DoPlo modulus estimates before and after compounding (i.e. averaging estimates from 10 scatterer realizations).
Figure 25C:
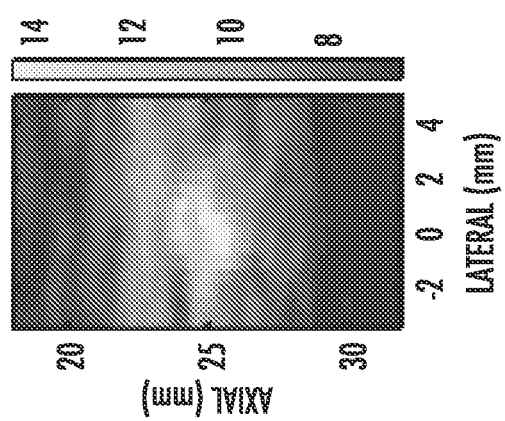
Figure 25B:
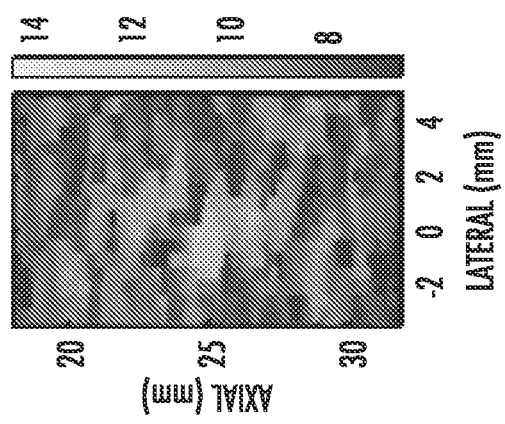
Figure 25A:
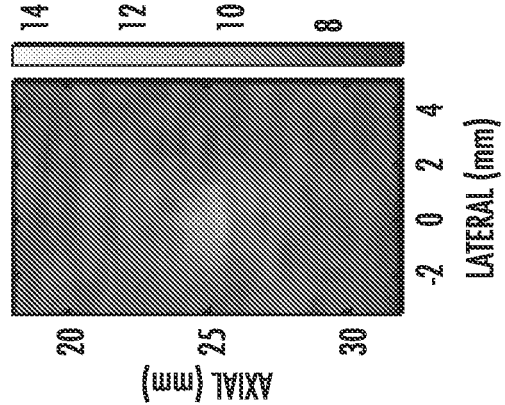

The fundamental spatial resolution of DoPlo, given DoPlo's overestimated inclusion widths in Table 1, may also be attributed to the interaction of each tracking beam's PSFs. Since DoPlo measurements rely on the focused tracking of displacements using beams with two different cross-sectional sizes, the displacement response of a scatterer located inside an elastic heterogeneity may disproportionately impact one of the two profiles that are intersected. For example, in FIGS. 23A-23C, the A-line for a lateral position of 1.0 mm from the inclusion center is inside the inclusion, but is 0.25 mm away from the inclusion boundary. Since the lateral resolution of such a backscatter signal roughly equals the product of the motion-tracking wavelength and F-number, the lateral resolution for a 6.15 MHz transmit pulse tracked using F-numbers 1.5 and 3.0 are 0.38 mm and 0.75 mm, respectively, based on the full-width-half-max of a PSF. This implies that, even in a perfect scenario where interframe or out-of-plane motion is not considered, estimates of tissue elasticity at mechanical boundaries may be impacted by stiffness information on either side. This is perhaps most apparent in FIG. 23B and FIG. 25B. While the vertical sides of the square inclusion in either image are more sharply defined than in the MTL-SWEI image in FIG. 23C, a gradient still persists in place of a sharply-defined border between the background and inclusion. This effect, on top of the semi-manual segmentation method used to programmatically outline inclusion positions for region-of-interest analyses, may account for erroneous inclusion size estimates and modulus estimate deviations in Table 1.

This phenomenon of off-axis mechanical "crosstalk" may have been further exaggerated by using the BSS-based displacement tracker. The BSS tracker is a biased estimator of phase shifts in a time series of beamformed RF lines across adjacent axial depths and adjacent RF lines [20]. In other words, displacements measured using a three-dimensional BSS tracker means that A-lines on the border of phantom regions with different elasticities depend on adjacent lines where displacements are measured purely in materials of either one of the two elasticities; 3D-BSS displacement profiles measured at borders of mechanical features may appear as a part of the inclusion, thereby appearing to stretch it laterally. This phenomenon is most easily observed in FIG. 25C where lateral "tails" appear to extend out of the left side of the inclusion at around 25 mm in depth.

Future work will also investigate the use of matrix array transducers to assess the impact of elevational focusing as a means to fully control PSF shapes for displacement tracking applications. Since previous work has already demonstrated the effects of changing PSFs for assessing tissue mechanical anisotropy (i.e. directional dependence of tissue viscoelasticity) for qualitative metrics of tissue mechanical properties, we hypothesize that DoPlo may augment existing methods of anisotropy imaging with control over elevational beam steering and focusing [26].

While DoPlo's lack of a lateral kernel obviates the need to sample displacements at multiple locations, it does not categorically eliminate spatial averaging. DoPlo measurements taken away from the RoE depend on a time-intersect that includes a time-of-flight component for shear waves traveling from the RoE to the position where displacements are tracked. While this may be counteracted by shifting the definition of displacement profiles' time axes so that features are measured to timepoints other than the ARF excitation, high variance in the inverse-square of times-intersect dominate using the PRF in this study [7]. Additional data-driven models including machine learning approaches may be considered for deriving moduli and seeking alternate features in displacement profiles that encode mechanical properties of tissue.

VI—Conclusion

We herein demonstrate the preliminary capabilities of DoPlo for differentiating the shear modulus of elastic materials. Using an FEM-derived empirical model, given a known axial position and push-track beam separation distance, the time-intersect of displacement profiles were converted into shear modulus estimates. Through this in silico and in vitro study, we showed that an empirical model based on the time-intersect can quantify shear elastic moduli in single points of space. We also quantitatively discriminated between soft and stiff regions in a single image using DoPlo in simulation with a comparable appearance to SWEI. Finally, we demonstrated that DoPlo moduli can be estimated using a clinical ultrasound system, and that modulus estimates remain constant over various ARF excitation magnitudes.

The disclosure of each the following references is incorporated herein by reference in its entirety.

REFERENCES

[1] K. Nightingale, M. S. Soo, R. Nightingale, and G. Trahey, "Acoustic radiation force impulse imaging: in vivo demonstration of clinical feasibility," *Ultrasound Med. Biol.*, vol. 28, no. 2, pp. 227-235, February 2002, doi: 10.1016/s0301-5629(01)00499-9.

[2] A. P. Sarvazyan, O. V Rudenko, S. D. Swanson, J. B. Fowlkes, and S. Y. Emelianov, "Shear wave elasticity imaging: a new ultrasonic technology of medical diagnostics," *Ultrasound Med. Biol.*, vol. 24, no. 9, pp. 1419-35, November 1998.

[3] S. A. McAleavey, K. R. Nightingale, and G. E. Trahey, "Estimates of echo correlation and measurement bias in acoustic radiation force impulse imaging," *IEEE Trans. Ultrason. Ferroelectr. Freq. Control*, vol. 50, no. 6, pp. 631-41, June 2003.
[4] L. Sandrin et al., "Transient elastography: A new non-invasive method for assessment of hepatic fibrosis," *Ultrasound Med. Biol.*, vol. 29, no. 12, pp. 1705-1713, 2003, doi: 10.1016/j.ultrasmedbio.2003.07.001.
[5] K. Nightingale, S. McAleavey, and G. Trahey, "Shear-wave generation using acoustic radiation force: in vivo and ex vivo results," *Ultrasound Med. Biol.*, vol. 29, no. 12, pp. 1715-23, December 2003.
[6] S. Chen, M. Fatemi, and J. F. Greenleaf, "Quantifying elasticity and viscosity from measurement of shear wave speed dispersion," *J. Acoust. Soc. Am.*, vol. 115, no. 6, pp. 2781-5, June 2004, doi: Doi 10.1121/1.1739480.
[7] K. A. Yokoyama, M. M. Hossain, and C. M. Gallippi, "Double-profile intersection (DoPIo) elastography: A new approach to quantifying tissue elasticity," in *IEEE International Ultrasonics Symposium*, 2019, vol. 2019-October, pp. 431-434, doi: 10.1109/ULTSYM.2019.8925667.
[8] L. Ostrovsky, A. Sutin, Y. Il'inskii, O. Rudenko, and A. Sarvazyan, "Radiation force and shear motions in inhomogeneous media," *J. Acoust. Soc. Am.*, vol. 121, no. 3, pp. 1324-1331, March 2007, doi: 10.1121/1.2532113.
[9] T. J. Czernuszewicz, J. E. Streeter, P. A. Dayton, and C. M. Gallippi, "Experimental validation of displacement underestimation in ARFI ultrasound," *Ultrason. Imaging*, vol. 35, no. 3, pp. 196-213, July 2013, doi: 10.1177/0161734613493262.
[10] W. F. Walker and G. E. Trahey, "A Fundamental Limit on Delay Estimation Using Partially Correlated Speckle Signals," *IEEE Trans. Ultrason. Ferroelectr. Freq. Control*, vol. 42, no. 2, pp. 301-308, 1995.
[11] A. H. Dhanaliwala, J. A. Hossack, and F. W. Mauldin, "Assessing and improving acoustic radiation force image quality using a 1.5-D transducer design," *IEEE Trans. Ultrason. Ferroelectr. Freq. Control*, vol. 59, no. 7, pp. 1602-1608, July 2012, doi: 10.1109/TUFFC.2012.2360.
[12] M. L. Palmeri, A. C. Sharma, R. R. Bouchard, R. W. Nightingale, and K. R. Nightingale, "A finite-element method model of soft tissue response to impulsive acoustic radiation force," *IEEE Trans. Ultrason. Ferroelectr. Freq. Control*, vol. 52, no. 10, pp. 1699-712, October 2005, doi: Doi 10.1109/Tuffc.2005.1561624.
[13] M. L. Palmeri, S. A. McAleavey, G. E. Trahey, and K. R. Nightingale, "Ultrasonic tracking of acoustic radiation force-induced displacements in homogeneous media," *IEEE Trans. Ultrason. Ferroelectr. Freq. Control*, vol. 53, no. 7, pp. 1300-1313, July 2006, doi: 10.1109/TUFFC.2006.1665078.
[14] J. A. Jensen, "Simulation of advanced ultrasound systems using field II," 2004 *2nd IEEE Int. Symp. Biomed. Imaging Macro to Nano*, vol. 1, pp. 636-639, 2004, doi: 10.1109/isbi.2004.1398618.
[15] Jφ. A. Jensen and N. B. Svendsen, "Calculation of Pressure Fields from Arbitrarily Shaped, Apodized, and Excited Ultrasound Transducers," *IEEE Trans. Ultrason. Ferroelectr. Freq. Control*, vol. 39, no. 2, pp. 262-267, 1992, doi: 10.1109/58.139123.
[16] G. F. Pinton, J. J. Dahl, and G. E. Trahey, "Rapid tracking of small displacements with ultrasound," *IEEE Trans. Ultrason. Ferroelectr. Freq. Control*, vol. 53, no. 6, pp. 1103-17, June 2006.
[17] F. N. Fritsch and R. E. Carlson, "Monotone Piecewise Cubic Interpolation," *SIAM J. Numer. Anal.*, vol. 17, no. 2, pp. 238-246, 1980, doi: 10.1137/0717021.
[18] W. C. Graustein, "Homogeneous Cartesian Coordinates. Linear Dependence of Points and Lines," in *Introduction to Higher Geometry*, W. C. Graustein, Ed. New York, 1930, pp. 29-49.
[19] P. H. S. Torr and A. Zisserman, "MLESAC: A new robust estimator with application to estimating image geometry," *Comput. Vis. Image Underst.*, vol. 78, no. 1, pp. 138-156, 2000, doi: 10.1006/cviu.1999.0832.
[20] M. M. Hossain, G. Torres, and C. M. Gallippi, "Improvement in Inclusion Contrast-to-Noise Ratio for Low-Displacement Acoustic Radiation Force (ARF) Elasticity Imaging Using a 3D Kernel Blind-Source Separation (BSS) Based Displacement Estimator," in *IEEE International Ultrasonics Symposium, IUS*, 2019, pp. 1395-1398, doi: 10.1109/ULTSYM.2019.8926181.
[21] T. F. Chan and L. A. Vese, "Active contours without edges," *IEEE Trans. Image Process*, vol. 10, no. 2, pp. 266-277, 2001, doi: 10.1109/83.902291.
[22] H. Ponnekanti, J. Ophir, Y. Huang, and I. Céspedes, "Fundamental mechanical limitations on the visualization of elasticity contrast in elastography," *Ultrasound Med. Biol.*, vol. 21, no. 4, pp. 533-543, 1995, doi: 10.1016/0301-5629(94)00136-2.
[23] R. F. Wagner, S. W. Smith, J. M. Sandrik, and H. Lopez, "Statistics of Speckle in Ultrasound B-Scans," *IEEE Trans. Sonics Ultrason.*, vol. 30, no. 3, pp. 156-163, May 1983, doi: 10.1109/T-SU.1983.31404.
[24] G. Trahey, "Properties of acoustical speckle in the presence of phase aberration part I: First order statistics," *Ultrason. Imaging*, vol. 10, no. 1, pp. 12-28, January 1988, doi: 10.1016/0161-7346(88)90063-6.
[25] S. Smith, "Properties of acoustical speckle in the presence of phase aberration part II: Correlation lengths," *Ultrason. Imaging*, vol. 10, no. 1, pp. 29-51, January 1988, doi: 10.1016/0161-7346(88)90064-8.
[26] M. M. Hossain, C. J. Moore, and C. M. Gallippi, "Acoustic Radiation Force Impulse (ARFI)-Induced Peak Displacements Reflect Degree of Anisotropy in Transversely Isotropic Elastic Materials," *IEEE Trans. Ultrason. Ferroelectr. Freq. Control*, vol. 64, no. 6, pp. 989-1001, 2017, doi: 10.1109/TUFFC.2017.2690223.
[1] K. Nightingale, M. S. Soo, R. Nightingale, and G. Trahey, "Acoustic radiation force impulse imaging: in vivo demonstration of clinical feasibility," *Ultrasound Med. Biol.*, vol. 28, no. 2, pp. 227-235, February 2002, doi: 10.1016/s0301-5629(01)00499-9.
[2] A. P. Sarvazyan, O. V Rudenko, S. D. Swanson, J. B. Fowlkes, and S. Y. Emelianov, "Shear wave elasticity imaging: a new ultrasonic technology of medical diagnostics," *Ultrasound Med. Biol.*, vol. 24, no. 9, pp. 1419-35, November 1998.
[3] S. A. McAleavey, K. R. Nightingale, and G. E. Trahey, "Estimates of echo correlation and measurement bias in acoustic radiation force impulse imaging," *IEEE Trans. Ultrason. Ferroelectr. Freq. Control*, vol. 50, no. 6, pp. 631-41, June 2003.
[4] L. Sandrin et al., "Transient elastography: A new non-invasive method for assessment of hepatic fibrosis," *Ultrasound Med. Biol.*, vol. 29, no. 12, pp. 1705-1713, 2003, doi: 10.1016/j.ultrasmedbio.2003.07.001.
[5] K. Nightingale, S. McAleavey, and G. Trahey, "Shear-wave generation using acoustic radiation force: in vivo and ex vivo results," *Ultrasound Med. Biol.*, vol. 29, no. 12, pp. 1715-23, December 2003.
[6] S. Chen, M. Fatemi, and J. F. Greenleaf, "Quantifying elasticity and viscosity from measurement of shear wave speed dispersion," *J. Acoust. Soc. Am.*, vol. 115, no. 6, pp. 2781-5, June 2004, doi: Doi 10.1121/1.1739480.
[7] K. A. Yokoyama, M. M. Hossain, and C. M. Gallippi, "Double-profile intersection (DoPlo) elastography: A new approach to quantifying tissue elasticity," in *IEEE International Ultrasonics Symposium*, 2019, vol. 2019-October, pp. 431-434, doi: 10.1109/ULTSYM.2019.8925667.
[8] L. Ostrovsky, A. Sutin, Y. Il'inskii, O. Rudenko, and A. Sarvazyan, "Radiation force and shear motions in inhomogeneous media," *J. Acoust. Soc. Am.*, vol. 121, no. 3, pp. 1324-1331, March 2007, doi: 10.1121/1.2532113.
[9] T. J. Czernuszewicz, J. E. Streeter, P. A. Dayton, and C. M. Gallippi, "Experimental validation of displacement underestimation in ARFI ultrasound," *Ultrason. Imaging*, vol. 35, no. 3, pp. 196-213, July 2013, doi: 10.1177/0161734613493262.
[10] W. F. Walker and G. E. Trahey, "A Fundamental Limit on Delay Estimation Using Partially Correlated Speckle Signals," *IEEE Trans. Ultrason. Ferroelectr. Freq. Control*, vol. 42, no. 2, pp. 301-308, 1995.
[11] A. H. Dhanaliwala, J. A. Hossack, and F. W. Mauldin, "Assessing and improving acoustic radiation force image quality using a 1.5-D transducer design," *IEEE Trans. Ultrason. Ferroelectr. Freq. Control*, vol. 59, no. 7, pp. 1602-1608, July 2012, doi: 10.1109/TUFFC.2012.2360.
[12] M. L. Palmeri, A. C. Sharma, R. R. Bouchard, R. W. Nightingale, and K. R. Nightingale, "A finite-element method model of soft tissue response to impulsive acoustic radiation force," *IEEE Trans. Ultrason. Ferroelectr. Freq. Control*, vol. 52, no. 10, pp. 1699-712, October 2005, doi: Doi 10.1109/Tuffc.2005.1561624.
[13] M. L. Palmeri, S. A. McAleavey, G. E. Trahey, and K. R. Nightingale, "Ultrasonic tracking of acoustic radiation force-induced displacements in homogeneous media," *IEEE Trans. Ultrason. Ferroelectr. Freq. Control*, vol. 53, no. 7, pp. 1300-1313, July 2006, doi: 10.1109/TUFFC.2006.1665078.
[14] J. A. Jensen, "Simulation of advanced ultrasound systems using field II," 2004 *2nd IEEE Int. Symp. Biomed. Imaging Macro to Nano*, vol. 1, pp. 636-639, 2004, doi: 10.1109/isbi.2004.1398618.
[15] Jφ. A. Jensen and N. B. Svendsen, "Calculation of Pressure Fields from Arbitrarily Shaped, Apodized, and Excited Ultrasound Transducers," *IEEE Trans. Ultrason. Ferroelectr. Freq. Control*, vol. 39, no. 2, pp. 262-267, 1992, doi: 10.1109/58.139123.
[16] G. F. Pinton, J. J. Dahl, and G. E. Trahey, "Rapid tracking of small displacements with ultrasound," *IEEE Trans. Ultrason. Ferroelectr. Freq. Control*, vol. 53, no. 6, pp. 1103-17, June 2006.
[17] F. N. Fritsch and R. E. Carlson, "Monotone Piecewise Cubic Interpolation," *SIAM J. Numer. Anal.*, vol. 17, no. 2, pp. 238-246, 1980, doi: 10.1137/0717021.
[18] W. C. Graustein, "Homogeneous Cartesian Coordinates. Linear Dependence of Points and Lines," in *Introduction to Higher Geometry*, W. C. Graustein, Ed. New York, 1930, pp. 29-49.
[19] P. H. S. Torr and A. Zisserman, "MLESAC: A new robust estimator with application to estimating image geometry," *Comput. Vis. Image Underst.*, vol. 78, no. 1, pp. 138-156, 2000, doi: 10.1006/cviu.1999.0832.
[20] M. M. Hossain, G. Torres, and C. M. Gallippi, "Improvement in Inclusion Contrast-to-Noise Ratio for Low-Displacement Acoustic Radiation Force (ARF) Elasticity Imaging Using a 3D Kernel Blind-Source Separation (BSS) Based Displacement Estimator," in *IEEE International Ultrasonics Symposium, IUS*, 2019, pp. 1395-1398, doi: 10.1109/ULTSYM.2019.8926181.
[21] T. F. Chan and L. A. Vese, "Active contours without edges," *IEEE Trans. Image Process*, vol. 10, no. 2, pp. 266-277, 2001, doi: 10.1109/83.902291.
[22] H. Ponnekanti, J. Ophir, Y. Huang, and I. Céspedes, "Fundamental mechanical limitations on the visualization of elasticity contrast in elastography," *Ultrasound Med. Biol.*, vol. 21, no. 4, pp. 533-543, 1995, doi: 10.1016/0301-5629(94)00136-2.
[23] R. F. Wagner, S. W. Smith, J. M. Sandrik, and H. Lopez, "Statistics of Speckle in Ultrasound B-Scans," *IEEE Trans. Sonics Ultrason.*, vol. 30, no. 3, pp. 156-163, May 1983, doi: 10.1109/T-SU.1983.31404.
[24] G. Trahey, "Properties of acoustical speckle in the presence of phase aberration part I: First order statistics," *Ultrason. Imaging*, vol. 10, no. 1, pp. 12-28, January 1988, doi: 10.1016/0161-7346(88)90063-6.
[25] S. Smith, "Properties of acoustical speckle in the presence of phase aberration part II: Correlation lengths," *Ultrason. Imaging*, vol. 10, no. 1, pp. 29-51, January 1988, doi: 10.1016/0161-7346(88)90064-8.
[26] M. M. Hossain, C. J. Moore, and C. M. Gallippi, "Acoustic Radiation Force Impulse (ARFI)-Induced Peak Displacements Reflect Degree of Anisotropy in Transversely Isotropic Elastic Materials," *IEEE Trans. Ultrason. Ferroelectr. Freq. Control*, vol. 64, no. 6, pp. 989-1001, 2017, doi: 10.1109/TUFFC.2017.2690223.

Those skilled in the art will recognize improvements and modifications to the preferred embodiments of the present subject matter. All such improvements and modifications are considered within the scope of the concepts disclosed herein and the embodiments that follow.

Abbreviations

At least some of the following abbreviations may be used in this disclosure.
ARF Acoustic Radiation Force
ARFI Acoustic Radiation Force Impulse
ASIC Application-Specific Integrated Circuit
CPU Central Processing Unit
DoPlo Double-Profile Intersection
DP Displacement Profile
DSP Digital Signal Processor
FEM Finite-Element Modeling
FPGA Field Programmable Gate Array
HIE Homogeneous, Isotropic, and Elastic
LUT Look-Up Table
ML Machine Learning
MRI Magnetic Resonance Imaging
OCT Optical Coherence Tomography
pF # push F-number
PRF Pulse-Repetition Frequency
PSF Point-Spread Function
RF Radio-Frequency
RoE Region of Excitation
SOC System On Chip
SWEI Shear-Wave Elasticity Imaging
tF # tracking F-number
TI Time of Intersection

What is claimed is:
1. A method for nondestructively measuring a physical characteristic of a material, the method comprising:
performing one or more interrogations of a material sample, each interrogation using a push focal configuration;

taking a plurality of measurements of displacement over time of a material sample caused by the one or more interrogations, each measurement using an interrogation focal configuration; and quantitatively or qualitatively assessing a physical characteristic of the material sample based on the plurality of measurements of displacement over time of the material sample, wherein at least one of:

a tracking focal configuration used for one of the plurality of measurements is different from a tracking focal configuration used for another of the plurality of measurements; and a plurality of interrogations is performed, wherein a push focal configuration used for one of the plurality of interrogations is different from a push focal configuration used for another of the plurality of interrogations.

2. The method of claim 1, wherein:

performing one or more interrogations of a material sample comprises:

applying, to a spatial position of a material sample, an interrogation having a push focal configuration and causing a displacement over time of the material sample; and wherein taking a plurality of measurements of displacement over time of a material sample caused by the one or more interrogations comprises:

taking, using a first tracking focal configuration, a first measurement of displacement over time of the material sample; and taking, using a second tracking focal configuration different from the first tracking focal configuration, a second measurement of displacement over time of the material sample.

3. The method of claim 2 wherein the first and second measurements of displacement over time are taken contemporaneously.

4. The method of claim 2 wherein the first and second measurements of displacement over time are taken sequentially.

5. The method of claim 2 wherein determining the physical characteristic of the material sample based on the first and second measurements of displacement over time of the material sample comprises calculating the physical characteristic according to an algorithm that uses the first and second measurements of displacement over time of the material sample as inputs to calculate a value of the physical characteristic.

6. The method of claim 5 wherein the algorithm also uses the first tracking focal configuration and the second tracking focal configuration to calculate the physical characteristics.

7. The method of claim 5 wherein the algorithm also uses at least one of a focal depth and a lateral offset from a region of excitation to calculate the physical characteristics.

8. The method of any one of claim 5 wherein the algorithm comprises the steps of:

superimposing the first measurement of displacement over time of the material sample and the second measurement of displacement over time of the material sample;

identifying or inferring features that are common to both displacements over time of the material sample; and determining the physical characteristic based on the identified or inferred common features.

9. The method of claim 8 wherein the common features comprise at least one of:

a first time at which a graph of the first measurement of displacement over time of the material sample intersects with a graph of the second measurement of displacement over time of the material sample;

a second time at which the graph of the first measurement of displacement over time of the material sample intersects with the graph of the second measurement of displacement over time of the material sample; and a time at which the graph of the first or second measurements of displacement over time of the material sample indicates a particular rate of recovery.

10. The method of claim 5 wherein the algorithm comprises a machine learning algorithm.

11. The method of claim 10 wherein the machine learning algorithm comprises a bagged tree model.

12. The method of claim 10 wherein the machine learning algorithm comprises a Gaussian process regression model.

13. The method of claim 1, wherein performing one or more interrogations of a material sample and taking a plurality of measurements of displacement over time of a material sample caused by the one or more interrogations comprises:

applying, to a spatial position of a material sample, an interrogation having a first push focal configuration and causing a first displacement over time of the material sample;

taking, using a first tracking focal configuration, a measurement of the first displacement over time of the material sample;

applying, to a spatial position of a material sample, an interrogation having the first push focal configuration and causing a second displacement over time of the material sample; and taking, using a second tracking focal configuration different from the first tracking focal configuration, a measurement of a second displacement over time of the material sample.

14. The method of claim 1, wherein performing one or more interrogations of a material sample and taking a plurality of measurements of displacement over time of a material sample caused by the one or more interrogations comprises:

applying, to a spatial position of a material sample, an interrogation having a first push focal configuration and causing a first displacement over time of the material sample;

taking, using a first tracking focal configuration, a measurement of the first displacement over time of the material sample;

applying, to a spatial position of a material sample, an interrogation having a second push focal configuration different from the first push focal configuration and causing a second displacement over time of the material sample; and taking, using the first tracking focal configuration, a measurement of a second displacement over time of the material sample.

15. The method of claim 1, wherein performing (300) one or more interrogations of a material sample and taking (302) a plurality of measurements of displacement over time of a material sample caused by the one or more interrogations comprises:

applying, to a spatial position of a material sample, an interrogation having a first push focal configuration and causing a first displacement over time of the material sample;

taking, using a first tracking focal configuration, a measurement of the first displacement over time of the material sample;

applying, to a spatial position of a material sample, an interrogation having a second push focal configuration different from the first push focal configuration and causing a second displacement over time of the material sample; and taking, using a second tracking focal configuration different from the first tracking focal configuration, a measurement of a second displacement over time of the material sample.

16. The method of claim 1 wherein the physical characteristic of the material sample comprises an elasticity of the material sample, a viscosity of the material sample, or an anisotropy of the material sample.

17. The method of claim 1 wherein the material sample comprises a tissue sample.

18. The method claim 1 wherein a tracking focal configuration used for one of the plurality of measurements is narrower than a tracking focal configuration used for another of the plurality of measurements.

19. The method of claim 1 wherein a push focal configuration used for one of the plurality of interrogations is narrower than a push focal configuration used for another of the plurality of interrogations.

20. The method of claim 1 wherein performing at least one interrogation comprises applying an Acoustic Radiation Force (ARF) to the material sample.

21. The method of claim 1 wherein at least one of the displacements over time of the material sample is measured using ultrasound.

22. The method of claim 1 wherein at least one of the displacements over time of the material sample is measured using an optical method.

23. The method of claim 22 wherein at least one of the displacements over time of the material sample is measured using an optical microscope.

24. The method of claim 23 wherein the optical method comprises Optical Coherence Tomography (OCT).

25. The method of claim 1 wherein at least one of the displacements over time of the material sample is measured using Magnetic Resonance Imaging (MRI).

26. The method of claim 1 wherein quantitatively or qualitatively assessing the physical characteristic includes quantitatively assessing the physical characteristic by relating the measurements to a corresponding quantity of the physical characteristic using a model that relates quantities of the physical characteristic to displacements over time.

27. The method of claim 1 wherein quantitatively or qualitatively assessing the physical characteristic includes qualitatively assessing the physical characteristic by using the measurements to assess a relative quality or amount of the physical characteristic in the material sample when compared to other material samples or to results from interrogations of the same material sample at different times.

28. A system for measuring a physical characteristic of a material, the system comprising:

one or more processors; and memory storing instructions executable by the one or more processors, whereby the system is operable to:

perform one or more interrogations of a material sample, each interrogation using a push focal configuration;

take a plurality of measurements of displacement over time of a material sample caused by the one or more interrogations, each measurement using an interrogation focal configuration; and determine a physical characteristic of the material sample based on the plurality of measurements of displacement over time of the material sample, wherein at least one of:

a tracking focal configuration used for one of the plurality of measurements is different from a tracking focal configuration used for another of the plurality of measurements; and a plurality of interrogations is performed, wherein a push focal configuration used for one of the plurality of interrogations is different from a push focal configuration used for another of the plurality of interrogations.

29. A non-transitory computer readable medium storing software instructions that when executed by one or more processors of a system for quantitatively measuring a physical characteristic of a material, cause the system to:

perform one or more interrogations of a material sample, each interrogation using a push focal configuration;

take a plurality of measurements of displacement over time of a material sample caused by the one or more interrogations, each measurement using an interrogation focal configuration; and determine a physical characteristic of the material sample based on the plurality of measurements of displacement over time of the material sample, wherein at least one of:

a tracking focal configuration used for one of the plurality of measurements is different from a tracking focal configuration used for another of the plurality of measurements; and a plurality of interrogations is performed, wherein a push focal configuration used for one of the plurality of interrogations is different from a push focal configuration used for another of the plurality of interrogations.

* * * * *